United States Patent
Caux et al.

(10) Patent No.: US 11,130,817 B2
(45) Date of Patent: Sep. 28, 2021

(54) CD73 BLOCKING AGENTS

(71) Applicants: INNATE PHARMA, Marseilles (FR); CENTRE LEON BERARD, Lyons (FR)

(72) Inventors: Christophe Caux, Bressolles (FR); Laurent Gauthier, Marseilles (FR); Nicolas Gourdin, Marseilles (FR); Christine Menetrier-Caux, Bressolles (FR); Carine Paturel, Marcy l'Etoile (FR); Ivan Perrot, Cassis (FR)

(73) Assignees: INNATE PHARMA, Marseilles (FR); CENTRE LÉON BÉRARD, Lyons (FR)

( * ) Notice: Subject to any disclaimer, the term of this patent is extended or adjusted under 35 U.S.C. 154(b) by 442 days.

(21) Appl. No.: 15/767,661

(22) PCT Filed: Oct. 11, 2016

(86) PCT No.: PCT/EP2016/074306
§ 371 (c)(1),
(2) Date: Apr. 12, 2018

(87) PCT Pub. No.: WO2017/064043
PCT Pub. Date: Apr. 20, 2017

(65) Prior Publication Data
US 2019/0225703 A1  Jul. 25, 2019

Related U.S. Application Data

(60) Provisional application No. 62/240,101, filed on Oct. 12, 2015, provisional application No. 62/240,112, filed on Oct. 12, 2015.

(51) Int. Cl.
*C07K 16/28* (2006.01)
*C07K 16/40* (2006.01)
*A61P 35/00* (2006.01)

(52) U.S. Cl.
CPC .......... *C07K 16/2896* (2013.01); *A61P 35/00* (2018.01); *C07K 16/40* (2013.01); *C07K 2317/33* (2013.01); *C07K 2317/34* (2013.01); *C07K 2317/74* (2013.01); *C07K 2317/92* (2013.01)

(58) Field of Classification Search
None
See application file for complete search history.

(56) References Cited

U.S. PATENT DOCUMENTS

2018/0030144 A1  2/2018  Chanteux et al.
2018/0237536 A1  8/2018  Perrot et al.

FOREIGN PATENT DOCUMENTS

| WO | WO 2016/055609 | 4/2016 |
|---|---|---|
| WO | WO 2016/075099 | 5/2016 |
| WO | WO 2016/081746 | 5/2016 |
| WO | WO 2016/081748 | 5/2016 |
| WO | WO 2016/131950 | 8/2016 |

OTHER PUBLICATIONS

Barry, F. et al. "The SH-3 and SH-4 Antibodies Recognize Distinct Epitopes on CD73 from Human Mesenchymal Stem Cells" *Biochemical and Biophysical Research Communications*, Nov. 1, 2001, pp. 519-524, vol. 289, No. 2.

Flocke, K. et al. "Monoclonal antibodies against 5'-nucleotidase from a human pancreatic tumor cell line: their characterization and inhibitory capacity on tumor cell adhesion to fibronectin substratum" *European Journal of Cell Biology*, Jun. 1, 1992, pp. 62-70, vol. 58, No. 1.

Häusler, S. Fm. et al. "Anti-CD39 and anti-CD73 antibodies A1 and 7G2 improve targeted therapy in ovarian cancer by blocking adenosine-dependent immune evasion" *American Journal of Translational Research*, Jan. 1, 2014, pp. 129-139, vol. 6, No. 2.

Hay, C. et al. "Abstract 285: MEDI9447: enhancing anti-tumor immunity by targeting CD73 in the tumor microenvironment" *Cancer Research*, AACR 106th Annual Meeting, Aug. 1, 2015, pp. 1-3, vol. 75, Suppl. 15.

Stagg, J. et al. "Anti-CD73 antibody therapy inhibits breast tumor growth and metastasis" *Proceedings of the National Academy of Sciences*, Jan. 26, 2010, pp. 1547-1552, vol. 107, No. 4.

Terp, M. G. et al. "Anti-Human CD73 Monoclonal Antibody Inhibits Metastasis Formation in Human Breast Cancer by Inducing Clustering and Internalization of CD73 Expressed on the Surface of Cancer Cells" *The Journal of Immunology*, Sep. 16, 2013, pp. 4165-4173, vol. 191, No. 8.

Thomson, L. F. et al. "Production and characterization of monoclonal antibodies to the glycosyl phosphatidylinositol-anchored lymphocyte differentiation antigen ecto-5'-nucleotidase (CD73)" *Tissue Antigens*, Jan. 1, 1990, pp. 9-19, vol. 35, No. 1.

Written Opinion in International Application No. PCT/EP2016/074306, dated Jan. 4, 2017, pp. 1-8.

*Primary Examiner* — Meera Natarajan
(74) *Attorney, Agent, or Firm* — Saliwanchik, Lloyd & Eisenschenk

(57) ABSTRACT

Provided are antibodies that bind and inhibit CD73, are capable of increasing the proliferation of T cells in the presence of CD39-expressing B cells and ATP. The invention also relates to cells producing such compounds; methods of making such compounds, and antibodies, fragments, variants, and derivatives thereof; pharmaceutical compositions comprising the same; methods of using the compounds to diagnose, treat or prevent cancer.

5 Claims, 14 Drawing Sheets
Specification includes a Sequence Listing.

SEQUENCE LISTING

<160> NUMBER OF SEQ ID NOS: 107

<210> SEQ ID NO 1
<211> LENGTH: 574
<212> TYPE: PRT
<213> ORGANISM: homo sapiens

<400> SEQUENCE: 1

```
Met Cys Pro Arg Ala Ala Arg Ala Pro Ala Thr Leu Leu Ala Leu
1               5                   10                  15

Gly Ala Val Leu Trp Pro Ala Ala Gly Ala Trp Glu Leu Thr Ile Leu
                20                  25                  30

His Thr Asn Asp Val His Ser Arg Leu Glu Gln Thr Ser Glu Asp Ser
            35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
                100                 105                 110

Met Ala Leu Gly Asn His Glu Phe Asp Asn Gly Val Glu Gly Leu Ile
            115                 120                 125

Glu Pro Leu Leu Lys Glu Ala Lys Phe Pro Ile Leu Ser Ala Asn Ile
        130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320
```

```
Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Thr Asp Glu Met Phe Trp Asn His Val
370                 375                 380

Ser Met Cys Ile Leu Asn Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
    450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
    530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570

<210> SEQ ID NO 2
<211> LENGTH: 553
<212> TYPE: PRT
<213> ORGANISM: homo sapiens

<400> SEQUENCE: 2

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125
```

```
Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Thr Asp Glu Met Phe Trp Asn His Val
    370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
    450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
    530                 535                 540
```

Arg Ile Lys His His His His His His
545                 550

<210> SEQ ID NO 3
<211> LENGTH: 117
<212> TYPE: PRT
<213> ORGANISM: mus musculus

<400> SEQUENCE: 3

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ile Tyr Ser Gly Ser Thr Ser Tyr Asn Pro Ser Leu
    50                  55                  60

Asn Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Glu Ala Tyr Leu Tyr Phe Asp Tyr Trp Gly Gln Gly Thr Thr
            100                 105                 110

Leu Thr Val Ser Ser
        115

<210> SEQ ID NO 4
<211> LENGTH: 107
<212> TYPE: PRT
<213> ORGANISM: mus musculus

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Arg
65                  70                  75                  80

Glu Asp Val Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 5
<211> LENGTH: 6
<212> TYPE: PRT
<213> ORGANISM: mus musculus

<400> SEQUENCE: 5

Ser Asp Tyr Ala Trp Asn
1               5

<210> SEQ ID NO 6
<211> LENGTH: 8
<212> TYPE: PRT

```
<213> ORGANISM: mus musculus

<400> SEQUENCE: 6

Gly Tyr Ser Ile Thr Ser Asp Tyr
1               5

<210> SEQ ID NO 7
<211> LENGTH: 9
<212> TYPE: PRT
<213> ORGANISM: mus musculus

<400> SEQUENCE: 7

Gly Tyr Ser Ile Thr Ser Asp Tyr Ala
1               5

<210> SEQ ID NO 8
<211> LENGTH: 16
<212> TYPE: PRT
<213> ORGANISM: mus musculus

<400> SEQUENCE: 8

Tyr Ile Ile Tyr Ser Gly Ser Thr Ser Tyr Asn Pro Ser Leu Asn Ser
1               5                   10                  15

<210> SEQ ID NO 9
<211> LENGTH: 3
<212> TYPE: PRT
<213> ORGANISM: mus musculus

<400> SEQUENCE: 9

Tyr Ser Gly
1

<210> SEQ ID NO 10
<211> LENGTH: 7
<212> TYPE: PRT
<213> ORGANISM: mus musculus

<400> SEQUENCE: 10

Ile Ile Tyr Ser Gly Ser Thr
1               5

<210> SEQ ID NO 11
<211> LENGTH: 8
<212> TYPE: PRT
<213> ORGANISM: mus musculus

<400> SEQUENCE: 11

Glu Ala Tyr Leu Tyr Phe Asp Tyr
1               5

<210> SEQ ID NO 12
<211> LENGTH: 6
<212> TYPE: PRT
<213> ORGANISM: mus musculus

<400> SEQUENCE: 12

Ala Tyr Leu Tyr Phe Asp
1               5

<210> SEQ ID NO 13
<211> LENGTH: 10
<212> TYPE: PRT
<213> ORGANISM: mus musculus
```

```
<400> SEQUENCE: 13

Ala Arg Glu Ala Tyr Leu Tyr Phe Asp Tyr
1               5                   10

<210> SEQ ID NO 14
<211> LENGTH: 11
<212> TYPE: PRT
<213> ORGANISM: mus musculus

<400> SEQUENCE: 14

Arg Ala Ser Gln Asp Ile Asn Asn Tyr Leu Asn
1               5                   10

<210> SEQ ID NO 15
<211> LENGTH: 7
<212> TYPE: PRT
<213> ORGANISM: mus musculus

<400> SEQUENCE: 15

Ser Gln Asp Ile Asn Asn Tyr
1               5

<210> SEQ ID NO 16
<211> LENGTH: 6
<212> TYPE: PRT
<213> ORGANISM: mus musculus

<400> SEQUENCE: 16

Gln Asp Ile Asn Asn Tyr
1               5

<210> SEQ ID NO 17
<211> LENGTH: 7
<212> TYPE: PRT
<213> ORGANISM: mus musculus

<400> SEQUENCE: 17

Tyr Thr Ser Arg Leu His Ser
1               5

<210> SEQ ID NO 18
<211> LENGTH: 3
<212> TYPE: PRT
<213> ORGANISM: mus musculus

<400> SEQUENCE: 18

Tyr Thr Ser
1

<210> SEQ ID NO 19
<211> LENGTH: 9
<212> TYPE: PRT
<213> ORGANISM: mus musculus

<400> SEQUENCE: 19

Gln Gln Gly Asn Thr Leu Pro Trp Thr
1               5

<210> SEQ ID NO 20
<211> LENGTH: 6
<212> TYPE: PRT
<213> ORGANISM: mus musculus

<400> SEQUENCE: 20
```

Gly Asn Thr Leu Pro Trp
1               5

<210> SEQ ID NO 21
<211> LENGTH: 120
<212> TYPE: PRT
<213> ORGANISM: mus musculus

<400> SEQUENCE: 21

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Asn Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Glu Gly Gly Tyr Asp Arg Tyr Ala Leu Asp Tyr Trp Gly Gln
            100                 105                 110

Gly Thr Ser Val Thr Val Ser Ser
        115                 120

<210> SEQ ID NO 22
<211> LENGTH: 106
<212> TYPE: PRT
<213> ORGANISM: mus musculus

<400> SEQUENCE: 22

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 23
<211> LENGTH: 5
<212> TYPE: PRT
<213> ORGANISM: mus musculus

<400> SEQUENCE: 23

Asn Tyr Tyr Ile His
1               5

<210> SEQ ID NO 24
<211> LENGTH: 7
<212> TYPE: PRT

-continued

<213> ORGANISM: mus musculus

<400> SEQUENCE: 24

Gly Tyr Thr Phe Thr Asn Tyr
1               5

<210> SEQ ID NO 25
<211> LENGTH: 8
<212> TYPE: PRT
<213> ORGANISM: mus musculus

<400> SEQUENCE: 25

Gly Tyr Thr Phe Thr Asn Tyr Tyr
1               5

<210> SEQ ID NO 26
<211> LENGTH: 17
<212> TYPE: PRT
<213> ORGANISM: mus musculus

<400> SEQUENCE: 26

Trp Ile Tyr Pro Gly Asn Val Asn Thr Lys Tyr Asn Glu Lys Phe Lys
1               5                   10                  15

Gly

<210> SEQ ID NO 27
<211> LENGTH: 4
<212> TYPE: PRT
<213> ORGANISM: mus musculus

<400> SEQUENCE: 27

Pro Gly Asn Val
1

<210> SEQ ID NO 28
<211> LENGTH: 8
<212> TYPE: PRT
<213> ORGANISM: mus musculus

<400> SEQUENCE: 28

Ile Tyr Pro Gly Asn Val Asn Thr
1               5

<210> SEQ ID NO 29
<211> LENGTH: 11
<212> TYPE: PRT
<213> ORGANISM: mus musculus

<400> SEQUENCE: 29

Glu Gly Gly Tyr Asp Arg Tyr Ala Leu Asp Tyr
1               5                   10

<210> SEQ ID NO 30
<211> LENGTH: 9
<212> TYPE: PRT
<213> ORGANISM: mus musculus

<400> SEQUENCE: 30

Gly Gly Tyr Asp Arg Tyr Ala Leu Asp
1               5

<210> SEQ ID NO 31
<211> LENGTH: 13
<212> TYPE: PRT

<213> ORGANISM: mus musculus

<400> SEQUENCE: 31

Ala Arg Glu Gly Gly Tyr Asp Arg Tyr Ala Leu Asp Tyr
1               5                   10

<210> SEQ ID NO 32
<211> LENGTH: 10
<212> TYPE: PRT
<213> ORGANISM: mus musculus

<400> SEQUENCE: 32

Ser Ala Ser Ser Val Ser Tyr Met Tyr
1               5                   10

<210> SEQ ID NO 33
<211> LENGTH: 6
<212> TYPE: PRT
<213> ORGANISM: mus musculus

<400> SEQUENCE: 33

Ser Ser Ser Val Ser Tyr
1               5

<210> SEQ ID NO 34
<211> LENGTH: 5
<212> TYPE: PRT
<213> ORGANISM: mus musculus

<400> SEQUENCE: 34

Ser Ser Val Ser Tyr
1               5

<210> SEQ ID NO 35
<211> LENGTH: 7
<212> TYPE: PRT
<213> ORGANISM: mus musculus

<400> SEQUENCE: 35

Leu Thr Ser Asn Leu Ala Ser
1               5

<210> SEQ ID NO 36
<211> LENGTH: 3
<212> TYPE: PRT
<213> ORGANISM: mus musculus

<400> SEQUENCE: 36

Leu Thr Ser
1

<210> SEQ ID NO 37
<211> LENGTH: 9
<212> TYPE: PRT
<213> ORGANISM: mus musculus

<400> SEQUENCE: 37

Gln Gln Trp Ser Ser Asn Pro Leu Thr
1               5

<210> SEQ ID NO 38
<211> LENGTH: 9
<212> TYPE: PRT
<213> ORGANISM: mus musculus

<400> SEQUENCE: 38

Leu Thr Ser Trp Ser Ser Asn Pro Leu
1               5

<210> SEQ ID NO 39
<211> LENGTH: 9
<212> TYPE: PRT
<213> ORGANISM: mus musculus

<400> SEQUENCE: 39

Gln Gln Trp Ser Ser Asn Pro Leu Thr
1               5

<210> SEQ ID NO 40
<211> LENGTH: 119
<212> TYPE: PRT
<213> ORGANISM: mus musculus

<400> SEQUENCE: 40

Gln Val Gln Leu Gln Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Asn Leu Thr Ser Glu Asp Ser Ala Val Tyr Tyr Cys
                85                  90                  95

Ala Arg Arg Gly Gly Tyr Gly Asn Trp Phe Ala Tyr Trp Gly Gln Gly
            100                 105                 110

Thr Leu Val Thr Val Ser Ala
        115

<210> SEQ ID NO 41
<211> LENGTH: 107
<212> TYPE: PRT
<213> ORGANISM: mus musculus

<400> SEQUENCE: 41

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Thr Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 42

```
<211> LENGTH: 120
<212> TYPE: PRT
<213> ORGANISM: mus musculus

<400> SEQUENCE: 42

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Asn Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Glu Gly Gly Tyr Asp Arg Tyr Ala Leu Asp Tyr Trp Gly Gln
            100                 105                 110

Gly Thr Ser Val Thr Val Ser Ser
        115                 120

<210> SEQ ID NO 43
<211> LENGTH: 106
<212> TYPE: PRT
<213> ORGANISM: mus musculus

<400> SEQUENCE: 43

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 44
<211> LENGTH: 122
<212> TYPE: PRT
<213> ORGANISM: mus musculus

<400> SEQUENCE: 44

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60
```

```
Lys Gly Lys Ala Thr Leu Thr Ser Asp Lys Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Trp Gly Tyr Asp Glu Gly Tyr Tyr Tyr Ala Met Asp Tyr Trp
            100                 105                 110

Gly Gln Gly Thr Ser Val Thr Val Ser Ser
        115                 120
```

<210> SEQ ID NO 45
<211> LENGTH: 107
<212> TYPE: PRT
<213> ORGANISM: mus musculus

<400> SEQUENCE: 45

```
Asp Ile Val Met Thr Gln Ser Pro Ser Ser Met Tyr Ala Ser Leu Gly
  1               5                  10                  15

Glu Arg Val Thr Ile Thr Cys Lys Ala Ser Gln Asp Ile Asn Ser Tyr
                 20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
         50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Glu Phe Pro Leu
                 85                  90                  95

Thr Phe Gly Ala Gly Thr Lys Leu Glu Leu Lys
            100                 105
```

<210> SEQ ID NO 46
<211> LENGTH: 118
<212> TYPE: PRT
<213> ORGANISM: mus musculus

<400> SEQUENCE: 46

```
Gln Ile Gln Leu Gln Gln Ser Gly Ala Glu Leu Val Lys Pro Gly Ala
  1               5                  10                  15

Ser Val Asn Leu Ser Cys Lys Thr Ser Gly Phe Thr Phe Ser Ser Ser
                 20                  25                  30

Tyr Ile Ser Trp Leu Lys Gln Lys Pro Gly Gln Ser Leu Glu Trp Ile
            35                  40                  45

Ala Trp Ile Tyr Ala Gly Thr Gly Thr Thr Arg Tyr Asn Gln Lys Phe
         50                  55                  60

Thr Gly Lys Ala Gln Leu Thr Val Asp Thr Ser Ser Arg Thr Ala Tyr
 65                  70                  75                  80

Met Gln Phe Ser Ser Leu Thr Thr Glu Asp Ser Ala Ile Tyr Tyr Cys
                 85                  90                  95

Ala Arg His Val Asn Trp Asp His Phe Glu Tyr Trp Gly Gln Gly Thr
            100                 105                 110

Thr Leu Thr Val Ser Ser
        115
```

<210> SEQ ID NO 47
<211> LENGTH: 107
<212> TYPE: PRT
<213> ORGANISM: mus musculus

```
<400> SEQUENCE: 47

Asp Ile Val Met Thr Gln Ser His Lys Phe Met Ala Thr Ser Val Gly
1               5                   10                  15

Asp Arg Val Asn Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Leu
        35                  40                  45

Tyr Trp Ala Ser Thr Arg Gln Thr Gly Val Pro Asp His Phe Thr Gly
50                  55                  60

Ser Gly Ser Gly Thr Asp Tyr Thr Leu Thr Ile Asn Ser Val Gln Ala
65                  70                  75                  80

Asp Asp Leu Ala Leu Tyr Tyr Cys Gln Gln Tyr Tyr Arg Thr Pro Trp
                85                  90                  95

Thr Phe Gly Gly Gly Thr Lys Leu Glu Ile Lys
            100                 105

<210> SEQ ID NO 48
<211> LENGTH: 5
<212> TYPE: PRT
<213> ORGANISM: mus musculus

<400> SEQUENCE: 48

Ser Tyr Trp Met His
1               5

<210> SEQ ID NO 49
<211> LENGTH: 7
<212> TYPE: PRT
<213> ORGANISM: mus musculus

<400> SEQUENCE: 49

Gly Tyr Thr Phe Thr Ser Tyr
1               5

<210> SEQ ID NO 50
<211> LENGTH: 8
<212> TYPE: PRT
<213> ORGANISM: mus musculus

<400> SEQUENCE: 50

Gly Tyr Thr Phe Thr Ser Tyr Trp
1               5

<210> SEQ ID NO 51
<211> LENGTH: 17
<212> TYPE: PRT
<213> ORGANISM: mus musculus

<400> SEQUENCE: 51

Glu Ile Asn Pro Ser Asn Gly Arg Thr Asn Tyr Asn Glu Lys Phe Lys
1               5                   10                  15

Ser

<210> SEQ ID NO 52
<211> LENGTH: 10
<212> TYPE: PRT
<213> ORGANISM: mus musculus

<400> SEQUENCE: 52

Arg Gly Gly Tyr Gly Asn Trp Phe Ala Tyr
1               5                   10
```

<210> SEQ ID NO 53
<211> LENGTH: 8
<212> TYPE: PRT
<213> ORGANISM: mus musculus

<400> SEQUENCE: 53

Gly Gly Tyr Gly Asn Trp Phe Ala
1               5

<210> SEQ ID NO 54
<211> LENGTH: 12
<212> TYPE: PRT
<213> ORGANISM: mus musculus

<400> SEQUENCE: 54

Ala Arg Arg Gly Gly Tyr Gly Asn Trp Phe Ala Tyr
1               5                   10

<210> SEQ ID NO 55
<211> LENGTH: 5
<212> TYPE: PRT
<213> ORGANISM: mus musculus

<400> SEQUENCE: 55

Ser Tyr Val Met His
1               5

<210> SEQ ID NO 56
<211> LENGTH: 4
<212> TYPE: PRT
<213> ORGANISM: mus musculus

<400> SEQUENCE: 56

Pro Ser Asn Gly
1

<210> SEQ ID NO 57
<211> LENGTH: 8
<212> TYPE: PRT
<213> ORGANISM: mus musculus

<400> SEQUENCE: 57

Gly Tyr Thr Phe Thr Ser Tyr Val
1               5

<210> SEQ ID NO 58
<211> LENGTH: 17
<212> TYPE: PRT
<213> ORGANISM: mus musculus

<400> SEQUENCE: 58

Tyr Ile Asn Pro Tyr Asn Asp Gly Thr Lys Tyr Asn Glu Lys Phe Lys
1               5                   10                  15

Gly

<210> SEQ ID NO 59
<211> LENGTH: 4
<212> TYPE: PRT
<213> ORGANISM: mus musculus

<400> SEQUENCE: 59

Pro Tyr Asn Asp
1

```
<210> SEQ ID NO 60
<211> LENGTH: 8
<212> TYPE: PRT
<213> ORGANISM: mus musculus

<400> SEQUENCE: 60

Ile Asn Pro Tyr Asn Asp Gly Thr
1               5

<210> SEQ ID NO 61
<211> LENGTH: 13
<212> TYPE: PRT
<213> ORGANISM: mus musculus

<400> SEQUENCE: 61

Trp Gly Tyr Asp Glu Gly Tyr Tyr Tyr Ala Met Asp Tyr
1               5                   10

<210> SEQ ID NO 62
<211> LENGTH: 11
<212> TYPE: PRT
<213> ORGANISM: mus musculus

<400> SEQUENCE: 62

Gly Tyr Asp Glu Gly Tyr Tyr Tyr Ala Met Asp
1               5                   10

<210> SEQ ID NO 63
<211> LENGTH: 15
<212> TYPE: PRT
<213> ORGANISM: mus musculus

<400> SEQUENCE: 63

Ala Arg Trp Gly Tyr Asp Glu Gly Tyr Tyr Tyr Ala Met Asp Tyr
1               5                   10                  15

<210> SEQ ID NO 64
<211> LENGTH: 5
<212> TYPE: PRT
<213> ORGANISM: mus musculus

<400> SEQUENCE: 64

Ser Ser Tyr Ile Ser
1               5

<210> SEQ ID NO 65
<211> LENGTH: 7
<212> TYPE: PRT
<213> ORGANISM: mus musculus

<400> SEQUENCE: 65

Gly Phe Thr Phe Ser Ser Ser
1               5

<210> SEQ ID NO 66
<211> LENGTH: 8
<212> TYPE: PRT
<213> ORGANISM: mus musculus

<400> SEQUENCE: 66

Gly Phe Thr Phe Ser Ser Ser Tyr
1               5
```

```
<210> SEQ ID NO 67
<211> LENGTH: 17
<212> TYPE: PRT
<213> ORGANISM: mus musculus

<400> SEQUENCE: 67

Trp Ile Tyr Ala Gly Thr Gly Thr Thr Arg Tyr Asn Gln Lys Phe Thr
1               5                   10                  15
Gly

<210> SEQ ID NO 68
<211> LENGTH: 4
<212> TYPE: PRT
<213> ORGANISM: mus musculus

<400> SEQUENCE: 68

Ala Gly Thr Gly
1

<210> SEQ ID NO 69
<211> LENGTH: 8
<212> TYPE: PRT
<213> ORGANISM: mus musculus

<400> SEQUENCE: 69

Ile Tyr Ala Gly Thr Gly Thr Thr
1               5

<210> SEQ ID NO 70
<211> LENGTH: 9
<212> TYPE: PRT
<213> ORGANISM: mus musculus

<400> SEQUENCE: 70

His Val Asn Trp Asp His Phe Glu Tyr
1               5

<210> SEQ ID NO 71
<211> LENGTH: 7
<212> TYPE: PRT
<213> ORGANISM: mus musculus

<400> SEQUENCE: 71

Val Asn Trp Asp His Phe Glu
1               5

<210> SEQ ID NO 72
<211> LENGTH: 11
<212> TYPE: PRT
<213> ORGANISM: mus musculus

<400> SEQUENCE: 72

Ala Arg His Val Asn Trp Asp His Phe Glu Tyr
1               5                   10

<210> SEQ ID NO 73
<211> LENGTH: 11
<212> TYPE: PRT
<213> ORGANISM: mus musculus

<400> SEQUENCE: 73

Lys Ala Ser Gln Asp Ile Asn Thr Tyr Leu Ser
1               5                   10
```

```
<210> SEQ ID NO 74
<211> LENGTH: 7
<212> TYPE: PRT
<213> ORGANISM: mus musculus

<400> SEQUENCE: 74

Ser Gln Asp Ile Asn Thr Tyr
1               5

<210> SEQ ID NO 75
<211> LENGTH: 6
<212> TYPE: PRT
<213> ORGANISM: mus musculus

<400> SEQUENCE: 75

Gln Asp Ile Asn Thr Tyr
1               5

<210> SEQ ID NO 76
<211> LENGTH: 7
<212> TYPE: PRT
<213> ORGANISM: mus musculus

<400> SEQUENCE: 76

Arg Ala Asn Arg Leu Val Asp
1               5

<210> SEQ ID NO 77
<211> LENGTH: 3
<212> TYPE: PRT
<213> ORGANISM: mus musculus

<400> SEQUENCE: 77

Arg Ala Asn
1

<210> SEQ ID NO 78
<211> LENGTH: 9
<212> TYPE: PRT
<213> ORGANISM: mus musculus

<400> SEQUENCE: 78

Leu Gln Tyr Asp Glu Phe Pro Tyr Thr
1               5

<210> SEQ ID NO 79
<211> LENGTH: 6
<212> TYPE: PRT
<213> ORGANISM: mus musculus

<400> SEQUENCE: 79

Tyr Asp Glu Phe Pro Tyr
1               5

<210> SEQ ID NO 80
<211> LENGTH: 11
<212> TYPE: PRT
<213> ORGANISM: mus musculus

<400> SEQUENCE: 80

Lys Ala Ser Gln Asp Ile Asn Ser Tyr Leu Ser
1               5                   10

<210> SEQ ID NO 81
<211> LENGTH: 7
```

```
<212> TYPE: PRT
<213> ORGANISM: mus musculus

<400> SEQUENCE: 81

Ser Gln Asp Ile Asn Ser Tyr
1               5

<210> SEQ ID NO 82
<211> LENGTH: 6
<212> TYPE: PRT
<213> ORGANISM: mus musculus

<400> SEQUENCE: 82

Gln Asp Ile Asn Ser Tyr
1               5

<210> SEQ ID NO 83
<211> LENGTH: 9
<212> TYPE: PRT
<213> ORGANISM: mus musculus

<400> SEQUENCE: 83

Leu Gln Tyr Asp Glu Phe Pro Leu Thr
1               5

<210> SEQ ID NO 84
<211> LENGTH: 6
<212> TYPE: PRT
<213> ORGANISM: mus musculus

<400> SEQUENCE: 84

Tyr Asp Glu Phe Pro Leu
1               5

<210> SEQ ID NO 85
<211> LENGTH: 11
<212> TYPE: PRT
<213> ORGANISM: mus musculus

<400> SEQUENCE: 85

Lys Ala Ser Gln Asp Val Ser Thr Ala Val Ala
1               5                   10

<210> SEQ ID NO 86
<211> LENGTH: 7
<212> TYPE: PRT
<213> ORGANISM: mus musculus

<400> SEQUENCE: 86

Ser Gln Asp Val Ser Thr Ala
1               5

<210> SEQ ID NO 87
<211> LENGTH: 6
<212> TYPE: PRT
<213> ORGANISM: mus musculus

<400> SEQUENCE: 87

Gln Asp Val Ser Thr Ala
1               5

<210> SEQ ID NO 88
<211> LENGTH: 7
<212> TYPE: PRT
<213> ORGANISM: mus musculus
```

```
<400> SEQUENCE: 88

Trp Ala Ser Thr Arg Gln Thr
1               5

<210> SEQ ID NO 89
<211> LENGTH: 3
<212> TYPE: PRT
<213> ORGANISM: mus musculus

<400> SEQUENCE: 89

Trp Ala Ser
1

<210> SEQ ID NO 90
<211> LENGTH: 9
<212> TYPE: PRT
<213> ORGANISM: mus musculus

<400> SEQUENCE: 90

Gln Gln Tyr Tyr Arg Thr Pro Trp Thr
1               5

<210> SEQ ID NO 91
<211> LENGTH: 6
<212> TYPE: PRT
<213> ORGANISM: mus musculus

<400> SEQUENCE: 91

Tyr Tyr Arg Thr Pro Trp
1               5

<210> SEQ ID NO 92
<211> LENGTH: 8
<212> TYPE: PRT
<213> ORGANISM: mus musculus

<400> SEQUENCE: 92

Ile Asn Pro Ser Asn Gly Arg Thr
1               5

<210> SEQ ID NO 93
<211> LENGTH: 5
<212> TYPE: PRT
<213> ORGANISM: Mus musculus

<400> SEQUENCE: 93

Ser Tyr Asn Met Tyr
1               5

<210> SEQ ID NO 94
<211> LENGTH: 5
<212> TYPE: DNA
<213> ORGANISM: Mus musculus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 94 synmn                                                                    5
```

<210> SEQ ID NO 95
<211> LENGTH: 17
<212> TYPE: PRT
<213> ORGANISM: Mus musculus

<400> SEQUENCE: 95

Tyr Ile Asp Pro Tyr Asn Gly Gly Thr Ser Tyr Asn Gln Lys Phe Lys
1               5                   10                  15
Gly

<210> SEQ ID NO 96
<211> LENGTH: 17
<212> TYPE: PRT
<213> ORGANISM: Mus musculus

<400> SEQUENCE: 96

Tyr Ile Asp Pro Tyr Asn Gly Gly Ser Ser Tyr Asn Gln Lys Phe Lys
1               5                   10                  15
Gly

<210> SEQ ID NO 97
<211> LENGTH: 17
<212> TYPE: PRT
<213> ORGANISM: Mus musculus

<400> SEQUENCE: 97

Tyr Ile Asp Pro Tyr Asn Gly Gly Ser Ser Tyr Asn Leu Thr Phe Lys
1               5                   10                  15
Gly

<210> SEQ ID NO 98
<211> LENGTH: 11
<212> TYPE: PRT
<213> ORGANISM: Mus musculus

<400> SEQUENCE: 98

Gly Tyr Gly Asn Tyr Lys Ala Trp Phe Ala Tyr
1               5                   10

<210> SEQ ID NO 99
<211> LENGTH: 11
<212> TYPE: PRT
<213> ORGANISM: Mus musculus

<400> SEQUENCE: 99

Gly Tyr Asn Asn Tyr Lys Ala Trp Phe Ala Tyr
1               5                   10

<210> SEQ ID NO 100
<211> LENGTH: 11
<212> TYPE: PRT
<213> ORGANISM: Mus musculus

<400> SEQUENCE: 100

Lys Ala Ser Gln Ser Val Thr Asn Asp Val Ala
1               5                   10

<210> SEQ ID NO 101
<211> LENGTH: 11
<212> TYPE: PRT
<213> ORGANISM: Mus musculus

<400> SEQUENCE: 101

Lys Ala Ser Gln Ser Val Ser Asn Asp Val Ala
1               5                   10

<210> SEQ ID NO 102
<211> LENGTH: 7
<212> TYPE: PRT
<213> ORGANISM: Mus musculus

<400> SEQUENCE: 102

Tyr Ala Ser Asn Arg Tyr Thr
1               5

<210> SEQ ID NO 103
<211> LENGTH: 8
<212> TYPE: PRT
<213> ORGANISM: Mus musculus

<400> SEQUENCE: 103

Gln Gln Asp Tyr Ser Ser Leu Thr
1               5

<210> SEQ ID NO 104
<211> LENGTH: 330
<212> TYPE: PRT
<213> ORGANISM: homo sapiens

<400> SEQUENCE: 104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Ala Glu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 105
<211> LENGTH: 330
<212> TYPE: PRT
<213> ORGANISM: homo sapiens

<400> SEQUENCE: 105

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 106
<211> LENGTH: 330
<212> TYPE: PRT
<213> ORGANISM: homo sapiens

<400> SEQUENCE: 106

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ser Ser Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

```
                       325                 330

<210> SEQ ID NO 107
<211> LENGTH: 330
<212> TYPE: PRT
<213> ORGANISM: Homo sapiens

<400> SEQUENCE: 107

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

CD73 BLOCKING AGENTS

CROSS-REFERENCE TO RELATED APPLICATIONS

This application is the U.S. national stage application of International Patent Application No. PCT/EP2016/074306, filed Oct. 11, 2016, which claims the benefit of U.S. Provisional Application Ser. No. 62/240,101 filed 12 Oct. 2015 and U.S. 62/240,112 filed 12 Oct. 2015, the disclosures of which are incorporated herein by reference in their entireties, including any drawings.

REFERENCE TO SEQUENCE LISTING

The present application is being filed along with a Sequence Listing in electronic format. The Sequence Listing is provided as a file entitled "CD73-2_ST25", created 11 Oct. 2016, which is 46 KB in size. The information in the electronic format of the Sequence Listing is incorporated herein by reference in its entirety.

FIELD OF THE INVENTION

The present invention relates to antigen-binding compounds (e.g. antibodies) that inhibit CD73. The invention also relates to cells producing such compounds; methods of making such compounds, and antibodies, fragments, variants, and derivatives thereof;

pharmaceutical compositions comprising the same; methods of using the compounds to diagnose, treat or prevent diseases, e.g. cancer.

BACKGROUND

CD73 (ecto-5'-nucleotidase) is a 70-kDa glycosylphosphatidylinositol (GPI)-anchored protein normally expressed on endothelial cells and subsets of hematopoietic cells. CD73, together with CD39, regulates adenosine triphosphate (ATP) metabolism. CD39 (NTPDase-1) converts ATP into AMP, with only trace amounts of ADP being released, while CD73 catalyzes the conversion of AMP to adenosine.

Adenosine triphosphate (ATP) and its metabolites AMP and adenosine, have important roles in cellular metabolism, signaling and immune homeostasis. The release of extracellular adenosine triphosphates (ATP) in response to cell death or cellular stress acts to activate immune responses. However, its metabolite adenosine has immunosuppressive activity. Extracellular adenosine accumulates in cancerous tissues and constitutes an important mechanism of tumor immune escape. Among other effects, tumor-derived adenosine profoundly inhibits infiltrating effector T cells through adenylyl cyclase-activating A2A receptors.

CD73 expression has been reported in a range of tumor cells, including leukemia, bladder cancer, glioma, glioblastoma, ovarian cancer, melanoma, prostate cancer, thyroid cancer, esophageal cancer and breast cancer. CD73 expression has also been associated with a prometastatic phenotype in melanoma and breast cancer. It has been shown that therapy with an antibody that binds murine CD73 can inhibit breast tumor growth and metastasis in mice (Stagg, et al. (2010) Proc. Natl. Acad. Sci. USA 104:1547-1552). Antibodies however generally do not cross react with human and mouse CD73, complicating the study of the antibodies and the biological functions of CD73. It has been shown that genetic deletion of A2A receptors can induce T cell-dependent tumor rejection (Ohta, et al., (2006) Proc Natl Acad Sci USA 103:13132-13137). Knock-down using siRNA or overexpression of CD73 on tumor cells can modulate tumor growth and metastasis (Beavis et al (2013 Proc. Natl. Acad. Sci. USA 110:14711-716; Stagg et al. (2010); Jin et al. (2010) Cancer Res. 70: 2245-55). CD73−/− mice are protected from transplanted and spontaneous tumors (Stagg et al. (2010) Cancer Res. 71: 2892-2900). In humans, high CD73 expression had been shown to be a negative prognostic for triple negative breast cancer (Loi et al (2013 Proc. Natl. Acad. Sci. USA 110: 11091-11096).

Despite the long-standing interest in CD73 as a therapeutic target, the activity required of an agent to target CD73 in vivo has not been fully elucidated. While CD73 is expressed on tumor cells, it is also expressed on different cells of the immune system, notably CD4 and CD8 T cells, as well as dendritic cells and B cells. While some antibodies have been reported to bind human CD73 and increase the activity or proliferation of T cells or modify the migration of tumor cells, it remains to be clarified how such antibodies function since such T cell modulation and CD73-mediated transmission of co-stimulatory signals have been reported to be possible without dependence on the ecto-5' nucleotidase activity of CD73 (Gutensohn et al. 1995 Cell Immunol. 161:213-217). Consequently, antibodies generically referred to as CD73 inhibitors may not act by modulating the ecto-5' nucleotidase activity of CD73. One antibody, 7G2 (Life Technologies), has been reported to inhibit CD73, however this antibody does not bind cell surface CD73 in flow cytometry, or at best only with very low affinity. Another antibody that binds CD73, clone AD2, has been reported to cause receptor clustering and internalization but have minimal effect on enzymatic activity. Yet another agent, 1E9, is reported to promote T cell signaling independently of enzymatic inhibition. A further mAb, 4G4, is reported to induce CD73 shedding from the T cell surface. Only one agent, although not further characterized, was reported to have partial ability to block enzymatic in an assay using recombinant CD73 (Sachsenmeier et al. (2012) J. Biomed. Screening 17:993-998), however this agent was a monovalent binding agent that provided partial inhibition and was later described as an antibody that induces intracellular internalization (Rust et al. (2013) Mol. Cancer 12:11). Additionally, one further complicating factor is that the antibodies described in the literature have generally been of murine isotypes that are capable of being bound by mouse and human Fcγ receptors, making it difficult to separate any potential blocking effect from Fc-expressing cell mediated effects. Anti-CD73 antibodies that are bound by mouse and human Fcγ receptors can mediate depletion (e.g. by ADCC) of CD73-expressing tumor cells (and possibly CD73-expressing immune suppressor cells), and/or may elicit the production of pro-inflammatory cytokines. While such antibodies can be effective to target tumors (CD73 is a tumor antigen), their effect may be mediated by mechanism other than true blockade of enzymatic activity. Consequently, the mode of action of antibodies remains elusive.

Thus, despite the interest in targeting CD73, the characteristics needed for effective anti-CD73 antibodies remain to be determined. CD73 expression on different cell types, including immune cells and tumor cells, combined with use of antibodies that either do not actually block CD73 or are not pure blockers, create a complex setting for evaluation of the underlying activity of antibodies. New assays and antibodies are needed.

SUMMARY OF THE INVENTION

The present invention arises, inter alia, from the discovery of CD73 antibodies provide potent enhancement of T cell proliferation when T cells are stimulated in an environment where AMP is being generated (e.g. a tumor microenvironment). These antibodies are capable of inhibiting the activity of the human CD73 polypeptide without binding to the enzymatic active site of the CD73 polypeptide. They can be produced in a format that provides bivalent binding to CD73. The antibodies can be effective to neutralize the enzymatic activity of CD73 without effector function, thereby reducing toxicity arising from expression of CD73 on healthy tissues. The antibodies disclosed herein include examples that induce intracellular internalization of CD73 as well as others that do not induce and/or increase intracellular internalization of CD73.

The present invention also arises from the discovery of screening assays for anti-CD73 antibodies that permit the elimination of false positive and negatives in functional assays. Based on the study of the expression of CD39 and CD73 in human immune cells (in particular high CD39 expression on TReg and monocytes and CD73 expressed on minor CD4 T cell subset but high on B cell population) an assay was developed associating different immune cells (not only T cells). The assay was performed with either exogenous ATP or AMP, which led to observation of a window for visualizing CD73 activity that is much more robust in presence of ATP than AMP when the CD39/CD73 cooperation is needed. T and B cell interactions on which the assay is based in depicted in FIG. 6. In one aspect, T cell proliferation assays are based on co-culture of T cells with CD39-expressing B cells in presence of ATP (a CD39 substrate), where the T cells are activated via co-stimulation of their TCR, notably by induction of CD3 and CD28 signalling. In contrast to evaluation of anti-CD73 antibodies by assessing T cell proliferation in presence of the CD73 substrate AMP, in which the rapid processing of AMP by CD73 does not permit functional blockade to be readily observed, the ATP-based co-culture assays permit the discovery of antibodies that have functional activity in a physiologically relevant setting. In other aspects, improved assays for blockade of enzymatic activity using soluble dimeric CD73 are provided that eliminate false-positive that block enzymatic activity by causing antibody:CD73 oligomerization.

In one aspect, the inventors have discovered antibodies that bind an epitope present on CD73 expressed at the surface of cells with high affinity and enhance T cell proliferation by causing down-modulation of cell surface CD73 polypeptide (by internalization of the CD73-antibody complex). Unlike previous antibodies that cause at least partial CD73 down-modulation but do not enhance T cell proliferation, the present antibodies have high efficiency in neutralization of CD73 activity in CD73-expressing cells (e.g. CD73-expressing T cells), and in particular have the ability to potently enhance T cell proliferation when T cell proliferation is stimulated in the presence of CD39-expressing cells and exogenously added CD39 substrate ATP.

The epitope on CD73 bound by these antibodies can be characterized as being present on CD73 polypeptides as expressed by a range of cells, e.g. CD73-expressing B cells, CD4 T cells, CD8 T cells, cancer cells, and the antibody binds such cellular CD73 with high affinity as determined by flow cytometry. For example, an antibody can be characterized by an $EC_{50}$, as determined by flow cytometry, of no more than 5 µg/ml, optionally no more than 3 µg/ml, no more than 1 µg/ml, no more than 0.5 µg/ml or no more than 0.1 µg/ml, for binding to cells that express at their surface a human CD73 polypeptide. In one embodiment the cells are cells that are made to express CD73 at their surface. In one embodiment the cells are cells that endogenously express CD73 at their surface, e.g. T cells, cancer cells, leukemia cells, bladder cancer cells, glioma cells, glioblastoma cells, ovarian cancer cells, melanoma cells, prostate cancer cells, thyroid cancer cells, esophageal cancer cells or breast cancer cells.

Binding by the neutralizing antibodies disclosed herein to their epitope on CD73 results in the down-modulation of CD73 expression on cells (e.g., causes internalization of the antibody-CD73 complex). In one embodiment, the epitope comprises 1, 2, 3, 4 or 5 residues selected from the group consisting of Q70, R73, A74, A107 and R109 (with reference to SEQ ID NO: 1). In one embodiment, the epitope does not comprise 1, 2, 3, 4 or 5 residues selected from the group consisting of P165, D168, N211, E296 and R297 (with reference to SEQ ID NO: 1).

In one embodiment, the antibody is capable of causing intracellular internalization of CD73, optionally of the antibody-CD73 complex. In one embodiment, the antibody is capable of increasing T cell proliferation (compared, for example, to isotype control), when the antibody is brought into contact with T cells co-cultured with CD39-expressing B cells, when the T cells are induced to proliferate in vitro by TCR co-stimulation, in the presence of ATP.

In one embodiment, provided is an antibody that specifically binds human CD73 expressed by a cell and that induces the down-modulation of CD73 cell surface expression, wherein the antibody is capable of increasing the proliferation of CD73-expressing T cells in the presence of CD39-expressing B cells and ATP. In one embodiment, the antibody is capable of causing intracellular internalization of CD73, optionally of the antibody-CD73 complex. In one embodiment, the antibody is capable of increasing T cell proliferation, when the antibody is brought into contact with T cells co-cultured with CD39-expressing B cells, wherein the T cells are induced to proliferate in vitro by TCR co-stimulation (stimulation of CD3 and CD28 signalling, e.g., using beads), in the presence of ATP. While the T cell populations may comprise CD73 expressing T cells, it can also comprise CD73-negative T cells. In addition, at least some B cells may express CD73. In one embodiment, ATP is provided at a concentration of about, or at least about, 60 µM when T cells are induced to proliferate, and proliferation is assessed at about 3 days following induction of proliferation. In one embodiment, the T cells are induced to proliferate using by agonizing CD3 and CD28 polypeptides on T cells (e.g. by bringing T cells into contact with beads functionalized with a CD3 agonist and a CD38 agonist). Optionally, no exogenous AMP is added during cell culture. Advantageously, while the T cell population will include CD73-expressing cells that are the directly targeted by the anti-CD73 antibody, the anti-CD73 antibody will permit the in vitro (and in vivo) enhancement of proliferation of a wider population of cells that express adenosine receptors. Notably, all T cells express adenosine receptors, and B cells may also express adenosine receptors.

In one aspect of any embodiment herein, the anti-CD73 antibody is capable of causing an increase in in vitro T cell proliferation of more than 50%, optionally at least 100%, optionally at least 200% (compared, for example, to isotype control).

While the antibodies block the enzymatic activity of soluble dimeric CD73, they do not block the enzymatic activity of soluble dimeric CD73 when provided at high excess of antibody to soluble CD73 polypeptide dimers. This may suggest that the antibodies may be binding CD73 polypeptides (as a CD73 dimer) in monovalent manner (an antibody binds to a single CD73 polypeptide chain with the CD73 homodimer). The anti-CD73 antibodies may however be capable of bivalent binding, where two antigen binding domains of an antibody each bind to a CD73 polypeptide chain within a different CD73 homodimer. Such binding may cause, e.g. via induction of receptor clustering and internalization, the down-modulation of CD73 on the surface of a cell.

In one embodiment, the anti-CD73 antibodies do not inhibit the enzymatic activity of soluble human dimeric CD73 polypeptide when the antibodies are provided at a substantial molar excess (e.g. at least 10-fold, 20-fold, 100-fold, etc.) to the CD73 polypeptide dimers. It has been found that most antibodies which inhibit the enzymatic activity of soluble human dimeric CD73 polypeptide as bivalent antibodies (when antibodies are not in substantial molar excess) will not inhibit the activity of cellular CD73 polypeptide (CD73 polypeptide expressed at the surface of a cell); these antibodies may be functioning by causing oligomerization of soluble CD73 dimers and. Such antibodies can be identified by their failure to inhibit soluble CD73 when the antibodies provided at a substantial molar excess to the CD73 polypeptide dimers.

In one embodiment, the anti-CD73 antibodies binds CD73 polypeptides in bivalent manner (e.g. the anti-CD73 antibody is an antibody having two antigen binding domains, for example two antigen binding domains each of which comprises and heavy chain variable region and a light chain variable region).

In one embodiment, the antibody is characterized by an EC50, as determined by flow cytometry, of no more than 10 µg/ml, optionally no more than 5 µg/ml, no more than 1 µg/ml, no more than 0.5 µg/ml or no more than 0.1 µg/ml, for binding to cells made to express at their surface a human CD73 polypeptide comprising an amino acid sequence of SEQ ID NO: 1.

In another aspect, the inventors have discovered antibodies that bind an epitope present on CD73 expressed at the surface of cells with high affinity and enhance T cell proliferation without a requirement for causing down-modulation of cell surface CD73 polypeptide (by internalization of the CD73-antibody complex), e.g. the antibodies do not induce and/or increase internalization of the CD73-antibody complex. Epitopes on CD73 bound by these exemplary antibodies are provided. Binding by the neutralizing antibodies disclosed herein to their epitope on CD73 (e.g. as dimer as expressed by a cell) does not result in the down-modulation of CD73 expression on the surface of cells. The binding of the antibodies does not cause internalization of the antibody-CD73 complex. In one embodiment, the epitope comprises 1, 2, 3, 4 or 5 or more residues selected from the group consisting of K145, K147, S152, S155, Y161, E203, K206 (with reference to SEQ ID NO: 1). In one embodiment, the epitope comprises 1, 2, 3, 4 or 5 residues selected from the group consisting of P165, D168, N211, E296, R297 (with reference to SEQ ID NO: 1). In one embodiment, provided is an antibody that specifically binds human CD73 expressed by a cell and that does not induce the down-modulation and/or internalization of the antibody-CD73 complex, wherein the antibody is capable of increasing the proliferation of T cells (compared, for example, to isotype control) in the presence of CD39-expressing B cells and ATP, when the T cells are induced to proliferate in vitro by TCR co-stimulation.

In one embodiment, provided is an antibody that specifically binds CD73 does not induce and/or increase internalization of the CD73-antibody complex and which is capable of increasing T cell proliferation, when the antibody is brought into contact with T cells co-cultured with CD39-expressing B cells, wherein the T cells are induced to proliferate in vitro by TCR co-stimulation (stimulation of CD3 and CD28 signalling, e.g., using beads) in the presence of ATP. The T cells may comprise CD73 expressing T cells, but may also comprise CD73-negative T cells. In one embodiment, ATP is provided at a concentration of about, or at least about, 60 µM when T cell are induced to proliferate, and proliferation is assessed at about 3 days following induction of proliferation. In one embodiment, the T cells are induced to proliferate by agonizing CD3 and CD28 polypeptides on T cells (e.g. by contacting T cells with beads functionalized with CD3 agonists and CD28 agonists). Optionally, no exogenous AMP is added during cell culture. Advantageously, while the T cell population will include CD73-expressing cells that are the directly targeted by the anti-CD73 antibody, the anti-CD73 antibody will permit the in vitro (and in vivo) enhancement of proliferation of a wider population of cells that express adenosine receptors. Notably, all T cells express adenosine receptors, and B cells may also express adenosine receptors. In one aspect of any embodiment herein, the anti-CD73 antibody is capable of causing an increase in in vitro T cell proliferation of more than 50%, optionally at least 100%, optionally at least 200% (compared, for example, to isotype control).

In one embodiment, the antibody that does not induce and/or increase internalization of the CD73-antibody complex also does not neutralize the 5'-ectonucletidase activity of a soluble human CD73 polypeptide (e.g., a CD73 dimer as in the Examples herein). In one embodiment, the anti-CD73 antibodies do not inhibit the enzymatic activity of soluble human dimeric CD73 polypeptide when the antibodies are provided at a substantial molar excess (e.g. at least 10-fold, 20-fold, 100-fold, etc.) to the CD73 polypeptide dimers. It has been found that most antibodies which inhibit the enzymatic activity of soluble human dimeric CD73 polypeptide as bivalent will not inhibit the activity of cellular CD73 polypeptide (CD73 polypeptide expressed at the surface of a cell); such antibodies may be functioning by causing oligomerization of soluble CD73 dimers. Such antibodies can be identified by their failure to inhibit soluble CD73 when the antibodies provided at a substantial molar excess to the CD73 polypeptide dimers.

In one embodiment, the antibody substantially lacks binding, via an Fc domain, to the CD16 human Fcγ receptor.

In one embodiment, provided is an antibody (e.g. as an isolated, monoclonal antibody) characterized by:
  a) specifically binding with high affinity, optionally bivalently, to human CD73 polypeptides expressed at the surface of a cell;
  b) increasing the proliferation of T cells when said T cells are induced to proliferate in vitro (e.g. via TCR co-stimulation) in the presence of CD39-expressing B cells and ATP;
  c) optionally, (i) inducing the down-modulation of cell surface CD73 (e.g. intracellular internalization of the antibody-CD73 complex) or (ii) not substantially increasing or inducing the down-modulation of cell surface CD73; and
  d) not specifically binding to the CD16 human Fcγ receptor, optionally not specifically binding, via an Fc domain, to human CD16, CD32A, CD32B and/or CD64 polypeptides.

Optionally, the antibody is capable of increasing T cell proliferation, when the antibody is brought into contact with CD73-expressing T cells co-cultured with CD39-expressing B cells and induced to proliferate in vitro (e.g. via TCR co-stimulation) in the presence of ATP. Optionally, ATP is provided at a concentration of at least 60 μM when T cells are induced to proliferate, and proliferation is assessed at about 3 days following induction of proliferation. Optionally, the CD73-expressing T cells are induced to proliferate by agonizing CD3 and CD28 polypeptides on T cells.

In one aspect of any embodiment, the anti-CD73 antibody binds to a single CD73 polypeptide chain within a CD73 homodimer. In one embodiment, the anti-CD73 antibody comprises a first and a second antigen binding domain, wherein each antigen binding domain binds to a CD73 polypeptide chain within a different CD73 homodimer.

In one aspect, provided is an antibody that neutralizes the enzymatic activity of CD73, wherein the antibody binds a (single) CD73 polypeptide dimer in monovalent manner (e.g. the anti-CD73 antibody binds to a single CD73 polypeptide chain within a CD73 homodimer).

In one embodiment, the anti-CD73 antibody comprises a first and a second antigen binding domain, wherein each antigen binding domain binds to a CD73 polypeptide chain within a different CD73 homodimer.

In one embodiment, the antibody competes for binding to a CD73 polypeptide comprising the amino acid sequence of SEQ ID NO 1 with antibody 7H10, 12F9, 15D7, 4B11, 11D9 or 9D2.

In one embodiment, the antibody (i) has reduced binding to a mutant CD73 polypeptide comprising a mutation at 1, 2, 3, 4 or 5 residues selected from the group consisting of Q70, R73, A74, A107 and R109 (with reference to SEQ ID NO: 1), and (ii) does not have reduced binding to a mutant CD73 polypeptide comprising a mutation at 1, 2, 3, 4 or 5 residues selected from the group consisting of P165, D168, N211, E296 and R297 (with reference to SEQ ID NO: 1), in each case relative to binding between the antibody and a wild-type CD73 polypeptide comprising the amino acid sequence of SEQ ID NO: 1.

In one embodiment, the antibody has reduced binding to a mutant CD73 polypeptide comprising a mutation at 1, 2, 3, 4, 5 or more residues selected from the group consisting of K145, K147, S152, S155, Y161, E203 and K206, (with reference to SEQ ID NO: 1), relative to binding between the antibody and a wild-type CD73 polypeptide comprising the amino acid sequence of SEQ ID NO: 1. In one embodiment, the antibody additionally has reduced binding to a mutant CD73 polypeptide comprising a mutation at 1, 2, 3, 4 or 5 residues selected from the group consisting of P165, D168, N211, E296 and R297, (with reference to SEQ ID NO: 1), relative to binding between the antibody and a wild-type CD73 polypeptide comprising the amino acid sequence of SEQ ID NO: 1.

In one embodiment, provided is an antibody that binds CD73, wherein the antibody (i) has reduced binding to a mutant CD73 polypeptide comprising a mutation at 1, 2, 3, 4 or 5 or more residues selected from the group consisting of K145, K147, S152, S155, Y161, E203, K206 (with reference to SEQ ID NO: 1), and/or (ii) has reduced binding to a mutant CD73 polypeptide comprising a mutation at 1, 2, 3, 4 or 5 residues selected from the group consisting of P165, D168, N211, E296, E297 (with reference to SEQ ID NO: 1), in each case relative to binding between the antibody and a wild-type CD73 polypeptide comprising the amino acid sequence of SEQ ID NO: 1.

In one embodiment, provided is an antibody that competes for binding to a CD73 polypeptide of SEQ ID NO: 1 with an antibody 7H10, 12F9, 15D7, 4B11, 11D9 or 9D2, and which increases, optionally substantially restores in vitro proliferation of T cells in the presence of ATP.

In one embodiment, provided is an antibody that binds CD73, wherein the antibody (i) has reduced binding to a mutant CD73 polypeptide comprising a mutation at 1, 2, 3, 4 or 5 residues selected from the group consisting of Q70, R73, A74, A107 and R109 (with reference to SEQ ID NO: 1), and (ii) does not have reduced binding to a mutant CD73 polypeptide comprising a mutation at 1, 2, 3, 4 or 5 residues selected from the group consisting of P165, D168, N211, E296 and R297 (with reference to SEQ ID NO: 1), in each case relative to binding between the antibody and a wild-type CD73 polypeptide comprising the amino acid sequence of SEQ ID NO: 1.

In one aspect of any of the embodiments of the invention, the antibody may have a heavy and/or light chain having one, two or three CDRs (e.g. the heavy and/or light chain CDR1, 2, and 3 according to Kabat, IMGT or Chotia numbering) of the respective heavy and/or light chain of antibody 7H10, 12F9, 15D7, 4B11, 11D9 or 9D2.

In one aspect of any of the embodiments therein, the anti-CD73 antibody is a tetrameric antibody comprising two heavy and two light chains, the heavy chains comprising Fc regions of human isotype and which have low or substantially lack binding to human Fcγ receptors (e.g., CD16A, CD16B, CD32A, CD32B and/or CD64).

In one embodiment, the antibodies are administered to an individual having a cancer in an amount and frequency sufficient to enhance the proliferation of T cells in an individual. In one embodiment, the antibodies are administered to an individual having a cancer in an amount and frequency sufficient to neutralize the activity of CD73 expressed by tumor cells, B cells, dendritic cells and/or T cells, e.g. cells in the tumor microenvironment. In one embodiment, the antibodies are administered in an amount and frequency sufficient to decrease the generation and/or concentration of adenosine in the tumor microenvironment. In one embodiment, the antibodies are administered in an amount and frequency sufficient to increase the generation and/or concentration of ATP in the tumor microenvironment. In one embodiment, the antibodies are administered in an amount and frequency sufficient to neutralize the activity of CD73 expressed by tumor cells. In one embodiment, the antibodies are administered in an amount and frequency sufficient to neutralize the activity of CD73 expressed by T cells, e.g., CD8 T cells and/or CD4 T cells, dendritic cells and/or B cells.

The antibodies will be useful in inhibiting CD73-mediated catabolism of AMP to adenosine, e.g. decreasing the concentration of adenosine in the tumor microenvironment. These antibodies will therefore be useful in reversing the immunosuppressive effect of CD73-mediated generation of adenosine by T cells, on B cells and/or on dendritic cells, for example in the treatment of cancer. In one embodiment, the anti-CD73 antibody neutralizes adenosine-mediated inhibition of proliferation, cytokine production, cytotoxicity and/or NFκB activity in T cells. In one embodiment, the anti-CD73 antibody neutralizes adenosine-mediated inhibition of immunoglobulin production by B cells. In one embodiment, the anti-CD73 antibody neutralizes adenosine-mediated inhibition of maturation of dendritic cells.

In one aspect, the antibodies will be useful in inhibiting (e.g. are administered in an amount effective to inhibit) the production, amounts and/or concentrations of adenosine into the tumor microenvironment.

In one aspect, by inhibiting the production of adenosine, the antibodies will be useful in inhibiting (e.g. are administered in an amount effective to inhibit) the migration of tumor cells via their adenosine receptors (A1 and A3 receptors).

In one aspect, the antibodies will be useful in inhibiting (e.g. are administered in an amount effective to inhibit) the metastasis of cancer.

Provided is a method for treating an individual, the method comprising, consisting essentially of or consisting of: administering to an individual a therapeutically active amount of any of the anti-CD73 antigen binding compounds described herein. Optionally, the compound is a non-depleting antibody (an antibody that does not deplete cells to which it binds). Optionally, the antibody is a full-length antibody. Optionally, the antibody is a chimeric, humanized or human antibody. Optionally, the antibody lacks an Fc domain or comprises a heavy chain constant region of IgG4 isotype or an IgG1, IgG2, IgG3 or IgG4 isotype comprising amino acid modifications, e.g., deletions or substitution(s), in the Fc domain to decrease or abolish binding to human CD16 and/or other human Fcγ receptors (e.g., e.g. CD16A, CD16B, CD32A, CD32B and/or CD64).

Optionally the individual is human having or who is susceptible to having a cancer.

In one embodiment, the anti-CD73 antibody is administered to an individual in combination with an antibody that neutralizes the inhibitory activity of human PD-1, optionally an anti-PD-1 antibody, optionally an anti-PD-L1 antibody. In one embodiment, the anti-CD73 antibody is administered to an individual having a cancer and who has a poor response, or prognostic for response, to treatment with an agent that neutralizes the inhibitory activity of human PD-1.

The antibodies are optionally characterized by binding affinity ($K_D$) for a human CD73 polypeptide (e.g., as shown in the Examples) of less than (better than) $10^{-9}$ M, preferably less than $10^{-10}$ M, or preferably less than $10^{-11}$M, and/or by binding human CD73 with an $EC_{50}$ lower than (better binding than) 1 µg/ml, preferably wherein the antibody has an $EC_{50}$ of no more than 0.5 µg/ml, optionally no more than 0.2 µg/ml, optionally no more than 0.1 µg/ml, for binding to cells (e.g. tumor cells) expressing human CD73 at the cell surface. The antibodies are preferably chimeric, human or humanized antibodies. In one embodiment, the antibody binds human and cynomolgus CD73. Optionally, the antibody does not bind to murine CD73.

In one embodiment, the antibody is a monoclonal antibody or a fragment thereof that retains binding specificity and ability to neutralize the enzymatic activity of CD73. In one embodiment, the antibody is an IgG1, IgG2, IgG3, or IgG4 antibody. For example, the antibody may be an antibody comprising an Fc domain of human IgG4 isotype, or an antibody comprising an Fc domain of any human IgG isotype (e.g. IgG1, IgG2, IgG3, or IgG4) modified to reduce or abolish binding between the Fc domain and an Fcγ receptor (e.g. CD16, CD32A, CD32B and/or CD64). Preferably, the antigen-binding compound does not comprise an Fc domain capable of inducing antibody mediated cellular cytotoxicity (ADCC) and/or CDC; optionally the antigen-binding compound does not comprise an Fc domain capable of substantially binding to a FcγRIIIA (CD16) polypeptide (e.g., comprises an Fc domain not capable of substantially binding to a FcγRIIIA (CD16) polypeptide; lacks an Fc domain (e.g. lacks a CH2 and/or CH3 domain; comprises an Fc domain of IgG2 or IgG4 isotype). Optionally if an Fc domain of IgG4 isotype is present, such Fc domain may comprise a stabilizing mutation to decrease formation of half-antibodies such as a mutation in the hinge, e.g. a S241P mutation. Optionally the antigen-binding compound consists of or comprises a Fab, Fab', Fab'-SH, F (ab') 2, Fv, a diabody, single-chain antibody fragment, or a multispecific antibody comprising multiple different antibody fragments. In one embodiment, the antigen-binding compound is not linked to a toxic moiety.

The invention also provides a nucleic acid encoding the human or humanized antibody or antibody fragment having any of the foregoing properties, a vector comprising such a nucleic acid, a cell comprising such a vector, and a method of producing a human anti-CD73 antibody, comprising culturing such a cell under conditions suitable for expression of the anti-CD73 antibody. The invention also relates to compositions, such as pharmaceutically acceptable compositions and kits, comprising such proteins, nucleic acids, vectors, and/or cells and typically one or more additional ingredients that can be active ingredients or inactive ingredients that promote formulation, delivery, stability, or other characteristics of the composition (e.g., various carriers). The invention further relates various new and useful methods making and using such antibodies, nucleic acids, vectors, cells, organisms, and/or compositions, such as in the modulation of CD73-mediated biological activities, for example in the treatment of diseases related thereto, notably cancers.

The invention also provides a method of potentiating the proliferation and/or activity of lymphocytes (e.g., B cells, T cells, dendritic cells) in a subject in need thereof, or for restoring the activity of lymphocytes (e.g., B cells, T cells, dendritic cells), or a method of relieving the adenosine-mediated inhibition of lymphocytes (e.g., B cells, T cells, dendritic cells), which method comprises administering to the subject an effective amount of any of the foregoing compositions. In one embodiment, the subject is a patient suffering from cancer. For example, the patient may be suffering from a solid tumor, e.g. colorectal cancer, renal cancer, ovarian cancer, lung cancer, breast cancer, pancreatic cancer or malignant melanoma, or other solid and non-solid tumors. In one embodiment, the patient may be suffering from a hematopietic cancer, e.g., acute myeloid leukaemia, chronic myeloid leukaemia, multiple myeloma, or non-Hodgkin's lymphoma.

The invention also provides methods for testing and/or producing an antibody, said method comprising the steps of:
 (a) providing an antibody (e.g. a batch of antibody) that binds a CD73 polypeptide,
 (b) assessing whether the antibody increases the proliferation of CD73-expressing T cells when said T cells are induced to proliferate in vitro by TCR co-stimulation, in the presence of CD39-expressing B cells and ATP, and
 (c) selecting the antibody (e.g. for production, development, use in therapy, etc.) if it increases the proliferation of CD73-expressing T cells, and optionally further producing and/or formulating for administration to a mammal a quantity of said antibody.

The invention also provides methods method of testing and/or producing an antibody, optionally for use in the treatment of cancer, said method comprising the steps of:
 (a) providing a plurality of antibodies that bind a CD73 polypeptide,
 (b) assessing whether antibodies among said plurality increase the proliferation of T cells when said T cells are induced to proliferate in vitro by TCR co-stimulation, in the presence of CD39-expressing B cells and ATP, and
 (c) optionally, selecting antibodies among said plurality that increase the proliferation of CD73-expressing T cells, optionally for use in the treatment of cancer.

In one embodiment of the methods, ATP is provided at a concentration of about, or at least about, 60 µM when T cells are induced to proliferate, and proliferation is assessed at about 3 days following induction of proliferation. In one embodiment, the T cells are induced to proliferate using by agonizing CD3 and CD28 polypeptides on T cells (e.g. by bringing T cells into contact with beads containing a CD3 agonist and a CD28 agonist). Optionally, no AMP is added during cell culture (the method is carried out with exogenous AMP).

In one embodiment of any of the methods of testing and/or producing, the method can further comprise (e.g., either before or after assessing whether antibodies among said plurality increase the proliferation of T cells) a step of assessing whether antibodies neutralizes the enzymatic activity of a soluble CD73 polypeptide. Optionally, the step comprises:
  (a) providing a plurality of antibodies that bind a CD73 polypeptide,
  (b) bringing each of said antibodies into contact (e.g., separately from one another) with a soluble CD73 polypeptide (e.g. in a cell-free assay, e.g. in the presence of AMP), and
  (c) selecting an antibody (e.g. those of step (b)) that neutralizes the enzymatic activity of said soluble CD73 polypeptide. Optionally, the CD73 polypeptide is a soluble CD73 dimer.

In one embodiment, the antibodies are capable of binding CD73 in bivalent manner, e.g. the antibodies are full length IgG antibodies. Optionally, step (b) comprises bringing each of said antibodies into contact with a soluble CD73 polypeptide in a cell-free assay, wherein antibodies are provided in a molar excess of antibody (compared to CD73 polypeptide). Optionally step (c) comprises selecting an antibody that neutralizes the enzymatic activity of said soluble CD73 polypeptide when antibodies are provided at a molar excess of antibody to CD73 dimers (e.g., an at least 2-fold, 5-fold, 10-fold, or 100-fold molar excess).

These aspects are more fully described in, and additional aspects, features, and advantages will be apparent from, the description of the invention provided herein.

BRIEF DESCRIPTION OF THE DRAWINGS

In FIG. 3A, antibody 7H10 binds to wild type CD73 (and other mutants, including mutant 5) but loses binding to mutant 2, while antibody AD2 binds to wild type CD73 and other mutants, but loses binding to mutant 2 and partially loses binding to mutant 5. In FIG. 3B, antibody 12F9 binds to wild type CD73 (and other mutants, including mutant 5) but loses binding to mutants 4 and 5.

FIGS. 8 and 9 show the ability of antibodies to cause reversion of inhibition of proliferation of TCR co-stimulated T cells in the presence of CD39-expressing B cells and exogenously added CD39 substrate ATP. FIGS. 8 and 9 shows antibody 7H10 and 12F9 were able to strongly increase T cell proliferation, and at a concentration of about 10 µg/ml were able to increase T cell proliferation by more than 100%. Antibody AD2 did not increase T cell proliferation.

DETAILED DESCRIPTION OF THE INVENTION

Definitions

Figure 1:
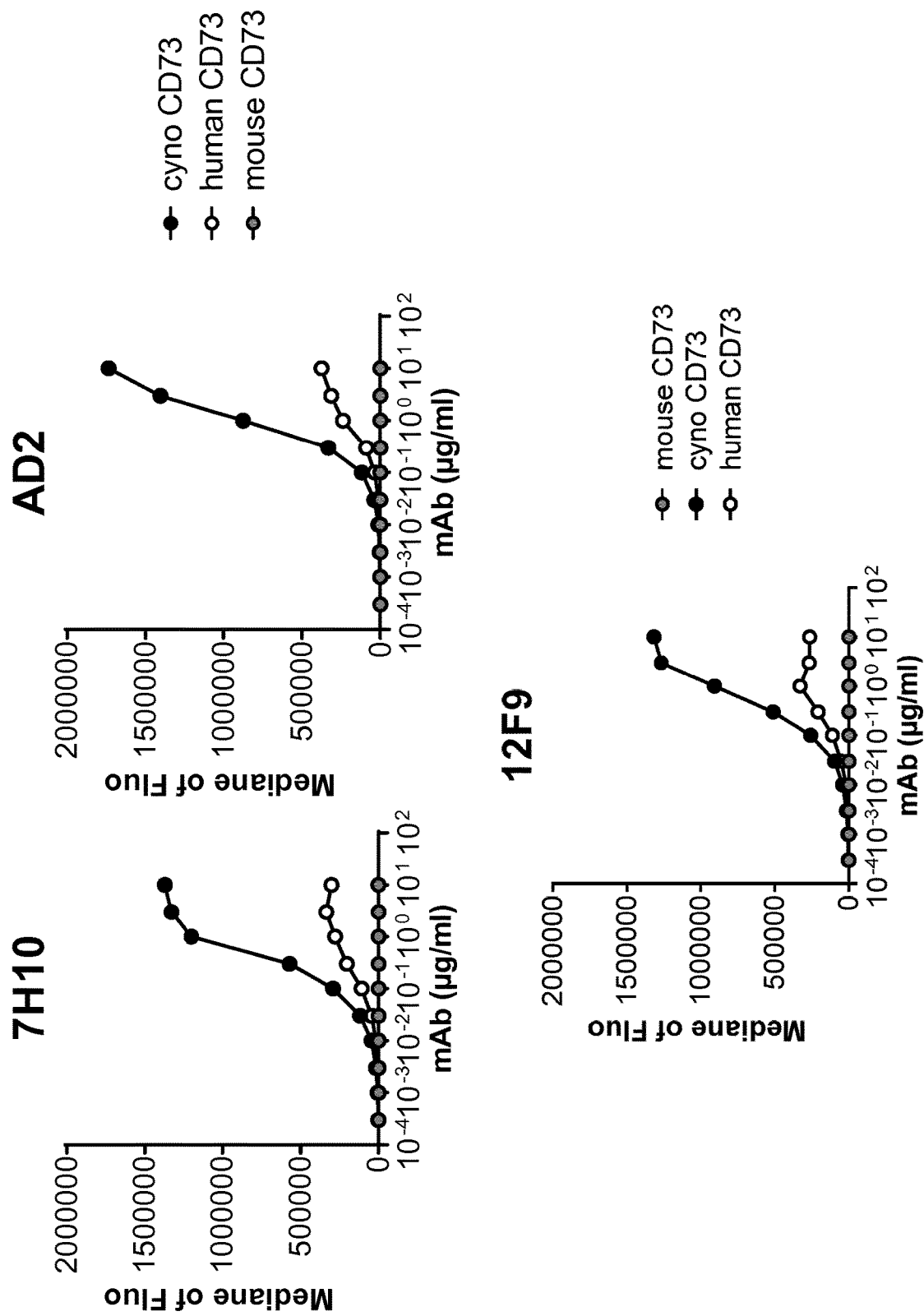
FIG. 1 shows results of titration of antibodies by flow cytometry on human CD73-expressing transfected cell lines. 7H10 and 12F9 bind to cells expressing human or cynomolgus (but not mouse) CD73 with excellent affinity. AD2 also binds to cells expressing human or cynomolgus CD73 but requires an approximately 4 fold higher concentration ($EC_{50}$).

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

Human CD73, also known as ecto-5'-nucleotidase and as 5-prime-ribonucleotide phospho-hydrolase, EC 3.1.3.5, encoded by the NT5E gene, exhibits 5'-nucleotidase, notably AMP-, NAD-, and NMN-nucleosidase, activities. CD73 catalyzes the conversion at neutral pH of purine 5-prime mononucleotides to nucleosides, the preferred substrate being AMP. The enzyme consists of a dimer of 2 identical 70-kD subunits bound by a glycosyl phosphatidyl inositol linkage to the external face of the plasma membrane The amino acid sequence of Human CD73 preprotein (monomer), including a signal sequence at amino acids 1-26, is shown in Genbank under accession number NP_002517, the entire disclosure of which is incorporated herein by reference, and as follows:

```
                                        (SEQ ID NO: 1)
MCPRAARAPA TLLLALGAVL WPAAGAWELT ILHTNDVHSR

LEQTSEDSSK CVNASRCMGG VARLFTKVQQ IRRAEPNVLL

LDAGDQYQGT IWFTVYKGAE VAHFMNALRY DAMALGNHEF

DNGVEGLIEP LLKEAKFPIL SANIKAKGPL ASQISGLYLP

YKVLPVGDEV VGIVGYTSKE TPFLSNPGTN LVFEDEITAL

QPEVDKLKTL NVNKIIALGH SGFEMDKLIA QKVRGVDVVV

GGHSNTFLYT GNPPSKEVPA GKYPFIVTSD DGRKVPVVQA

YAFGKYLGYL KIEFDERGNV ISSHGNPILL NSSIPEDPSI

KADINKWRIK LDNYSTQELG KTIVYLDGSS QSCRFRECNM

GNLICDAMIN NNLRHTDEMF WNHVSMCILN GGGIRSPIDE

RNNGTITWEN LAAVLPFGGT FDLVQLKGST LKKAFEHSVH

RYGQSTGEFL QVGGIHVVYD LSRKPGDRVV KLDVLCTKCR

VPSYDPLKMD EVYKVILPNF LANGGDGFQM IKDELLRHDS

GDQDINVVST YISKMKVIYP AVEGRIKFST GSHCHGSFSL

IFLSLWAVIF VLYQ
```

Whenever within this whole specification "treatment of cancer" or the like is mentioned with reference to anti-CD73 binding agent (e.g. antibody), there is meant: (a) method of treatment of cancer, said method comprising the step of administering (for at least one treatment) an anti-CD73 binding agent, (preferably in a pharmaceutically acceptable carrier material) to an individual, a mammal, especially a human, in need of such treatment, in a dose that allows for the treatment of cancer, (a therapeutically effective amount), preferably in a dose (amount) as specified herein; (b) the use of an anti-CD73 binding agent for the treatment of cancer, or an anti-CD73 binding agent, for use in said treatment (especially in a human); (c) the use of an anti-CD73 binding agent for the manufacture of a pharmaceutical preparation for the treatment of cancer, a method of using an anti-CD73 binding agent for the manufacture of a pharmaceutical preparation for the treatment of cancer, comprising admixing an anti-CD73 binding agent with a pharmaceutically acceptable carrier, or a pharmaceutical preparation comprising an effective dose of an anti-CD73 binding agent that is appropriate for the treatment of cancer; or (d) any combination of a), b), and c), in accordance with the subject matter allowable for patenting in a country where this application is filed.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG are the exemplary classes of antibodies employed herein because they are the most common antibodies in the physiological situation and because they are most easily made in a laboratory setting. Optionally the antibody is a monoclonal antibody. Particular examples of antibodies are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. CD73, as assessed using either recombinant forms of the proteins, epitopes therein, or native proteins present on the surface of isolated target cells. Competitive binding assays and other methods for determining specific binding are further described below and are well known in the art.

When an antibody is said to "compete with" a particular monoclonal antibody, it means that the antibody competes with the monoclonal antibody in a binding assay using either recombinant CD73 molecules or surface expressed CD73 molecules. For example, if a test antibody reduces the binding of a reference antibody to a CD73 polypeptide or CD73-expressing cell in a binding assay, the antibody is said to "compete" respectively with the reference antibody.

The term "affinity", as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

Within the context herein a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "deplete" or "depleting", with respect to CD73-expressing cells, means a process, method, or compound that results in killing, elimination, lysis or induction of such killing, elimination or lysis, so as to negatively affect the number of such CD73-expressing cells present in a sample or in a subject.

The term "internalization", used interchangeably with "intracellular internalization", refers to the molecular, biochemical and cellular events associated with the process of translocating a molecule from the extracellular surface of a cell to the intracellular surface of a cell. The processes responsible for intracellular internalization of molecules are well-known and can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing internalization" comprises events wherein intracellular internalization is initiated and/or the rate and/or extent of intracellular internalization is increased.

The term "agent" is used herein to denote a chemical compound, a mixture of chemical compounds, a biological macromolecule, or an extract made from biological materials. The term "therapeutic agent" refers to an agent that has biological activity.

For the purposes herein, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "hypervariable region" when used herein refers to the amino acid residues of an antibody that are responsible for antigen binding. The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917), or a similar system for determining essential amino acids responsible for antigen binding. Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Ws.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Production of Antibodies

The anti-CD73 agent that can be used for the treatment of cancers binds an extra-cellular portion of human CD73 polypeptide and neutralizes the activity of CD73, e.g. in a reporter cell, tumor cell, a T cell, a B cell, by causing the induction of internalization of CD73, or by acting as an allosteric or non-competitive inhibitor of CD73 without inducing intracellular internalization of CD73. The agent can inhibit the 5'-ectonucleotidase activity of CD73. In one embodiment, the antibody inhibits CD73-mediated generation of adenosine by a CD73-expressing cell. In one embodiment, the antibody inhibits CD73-mediated catabolism of AMP to adenosine by a CD73-expressing cell. In one embodiment, the antibody inhibits adenosine-mediated inhibition of lymphocyte activity (e.g. T cell, B cells, dendritic cells). In one aspect of the invention, the agent is an antibody selected from a full-length antibody, an antibody fragment, and a synthetic or semi-synthetic antibody-derived molecule.

An antibody that can "neutralize the enzymatic activity of CD73" can refer to a process in which the 5'-nucleotidase (5'-ectonucleotidase) activity of CD73 is inhibited in a CD73-expressing cell. This comprises, notably the inhibition of CD73-mediated generation of adenosine, i.e. the inhibition of CD73-mediated catabolism of AMP to adenosine. This can be measured for example in a cellular assay that measures the capacity of a test compound to inhibit the conversion of AMP to adenosine, either directly or indirectly. In one embodiment, an antibody preparation causes at least a 50% decrease in the conversion of AMP to adenosine, at least a 70% decrease in the conversion of AMP to adenosine, or at least a 80% decrease in the conversion of AMP to adenosine, referring, for example, to the assays described herein.

In one aspect of the invention, the agent is an antibody selected from a fully human antibody, a humanized antibody, and a chimeric antibody.

In one aspect of the invention, the agent is a fragment of an antibody comprising a constant domain selected from IgG1, IgG2, IgG3 and IgG4.

In one aspect of the invention, the agent is an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment.

In one aspect of the invention, the agent is a synthetic or semisynthetic antibody-derived molecule selected from a scFV, a dsFV, a minibody, a diabody, a triabody, a kappa body, an IgNAR; and a multispecific antibody.

In one aspect of the invention, the antibody is in at least partially purified form.

In one aspect of the invention, the antibody is in essentially isolated form.

The antibodies may be produced by a variety of techniques known in the art. Typically, they are produced by immunization of a non-human animal, preferably a mouse, with an immunogen comprising a CD73 polypeptide, preferably a human CD73 polypeptide. The CD73 polypeptide may comprise the full length sequence of a human CD73 polypeptide, or a fragment or derivative thereof, typically an immunogenic fragment, i.e., a portion of the polypeptide comprising an epitope exposed on the surface of cells expressing a CD73 polypeptide. Such fragments typically contain at least about 7 consecutive amino acids of the mature polypeptide sequence, even more preferably at least about 10 consecutive amino acids thereof. Fragments typically are essentially derived from the extra-cellular domain of the receptor. In one embodiment, the immunogen comprises a wild-type human CD73 polypeptide in a lipid membrane, typically at the surface of a cell. In a specific embodiment, the immunogen comprises intact cells, particularly intact human cells, optionally treated or lysed. In another embodiment, the polypeptide is a recombinant CD73 polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). The immunogen is suspended or dissolved in a buffer, optionally with an adjuvant, such as complete or incomplete Freund's adjuvant. Methods for determining the amount of immunogen, types of buffers and amounts of adjuvant are well known to those of skill in the art and are not limiting in any way. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with CD73 polypeptides.

In an alternate embodiment, lymphocytes from a non-immunized non-human mammal are isolated, grown in vitro, and then exposed to the immunogen in cell culture. The lymphocytes are then harvested and the fusion step described below is carried out.

For monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Murine myeloma lines include, but are not limited to, those derived from MOPC-21 and MPC-11 mouse tumors available from the Salk Institute Cell Distribution Center, San Diego, U.S.A, X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to CD73 polypeptide gene products. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. Typically, the antibodies will also be tested for the ability to bind to CD73 polypeptides, e.g., CD73-expressing cells.

Hybridomas that are confirmed to produce a monoclonal antibody can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that bind(s) to CD73, particularly substantially or essentially the same epitope as monoclonal antibody 7H10, 12F9, 15D7, 4B11, 11D9 or 9D2, can be readily determined using any one of a variety of immunological screening assays in which antibody competition can be assessed. Many such assays are routinely practiced and are well known in the art (see, e. g., U.S. Pat. No. 5,660,827, issued Aug. 26, 1997, which is specifically incorporated herein by reference).

For example, where the test antibodies to be examined are obtained from different source animals, or are even of a different Ig isotype, a simple competition assay may be employed in which the control (7H10, 12F9, 15D7, 4B11, 11D9 or 9D2, for example) and test antibodies are admixed (or pre-adsorbed) and applied to a sample containing CD73 polypeptides. Protocols based upon western blotting and the use of BIACORE analysis are suitable for use in such competition studies.

In certain embodiments, one pre-mixes the control antibodies (7H10, 12F9, 15D7, 4B11, 11D9 or 9D2, for example) with varying amounts of the test antibodies (e.g., about 1:10 or about 1:100) for a period of time prior to applying to the CD73 antigen sample. In other embodiments, the control and varying amounts of test antibodies can simply be admixed during exposure to the CD73 antigen sample. As long as one can distinguish bound from free antibodies (e. g., by using separation or washing techniques to eliminate unbound antibodies) and 7H10, 12F9, 15D7, 4B11, 11D9 or 9D2) from the test antibodies (e. g., by using species-specific or isotype-specific secondary antibodies or by specifically labeling 7H10, 12F9, 15D7, 4B11, 11D9 or 9D2 with a detectable label) one can determine if the test antibodies reduce the binding of 7H10, 12F9, 15D7, 4B11, 11D9 or 9D2 to the antigens. The binding of the (labeled) control antibodies in the absence of a completely irrelevant antibody can serve as the control high value. The control low value can be obtained by incubating the labeled (e.g., 7H10) antibodies with unlabelled antibodies of exactly the same type (e.g., 7H10), where competition would occur and reduce binding of the labeled antibodies. In a test assay, a significant reduction in labeled antibody reactivity in the presence of a test antibody is indicative of a test antibody that may recognize substantially the same epitope, i.e., one that "cross-reacts" or competes with the labeled (e.g., 7H10) antibody. Any test antibody that reduces the binding of 7H10 (or, e.g., 12F9, 15D7, 4B11, 11D9 or 9D2) to CD73 antigens by at least about 50%, such as at least about 60%, or more preferably at least about 80% or 90% (e. g., about 65-100%), at any ratio of anti-CD73 antibody:test antibody between about 1:10 and about 1:100 is considered to be an antibody that competes with 7H10 (or the respective 12F9, 15D7, 4B11, 11D9 or 9D2). Preferably, such test antibody will reduce the binding of 7H10 (or, e.g., 12F9, 15D7, 4B11, 11D9 or 9D2) to the CD73 antigen by at least about 90% (e.g., about 95%).

Competition can also be assessed by, for example, a flow cytometry test. In such a test, cells bearing a given CD73 polypeptide can be incubated first with 7H10, for example, and then with the test antibody labeled with a fluorochrome or biotin. The antibody is said to compete with 7H10 if the binding obtained upon preincubation with a saturating amount of 7H10 is about 80%, preferably about 50%, about 40% or less (e.g., about 30%, 20% or 10%) of the binding (as measured by mean of fluorescence) obtained by the antibody without preincubation with 7H10. Alternatively, an antibody is said to compete with 7H10 if the binding obtained with a labeled 7H10 antibody (by a fluorochrome or biotin) on cells preincubated with a saturating amount of test antibody is about 80%, preferably about 50%, about 40%, or less (e. g., about 30%, 20% or 10%) of the binding obtained without preincubation with the test antibody.

A simple competition assay in which a test antibody is pre-adsorbed and applied at saturating concentration to a surface onto which a CD73 antigen is immobilized may also be employed. The surface in the simple competition assay is preferably a BIACORE chip (or other media suitable for surface plasmon resonance (SPR Biacore) analysis). The control antibody (e.g., 7H10) is then brought into contact with the surface at a CD73-saturating concentration and the CD73 and surface binding of the control antibody is measured. This binding of the control antibody is compared with the binding of the control antibody to the CD73-containing surface in the absence of test antibody. In a test assay, a significant reduction in binding of the CD73-containing surface by the control antibody in the presence of a test antibody can be indicative that the test antibody will recognize substantially the same epitope as the control antibody. Any test antibody that reduces the binding of control (such as 7H10) antibody to a CD73 antigen by at least about 30% or more, preferably about 40%, can be considered to be an antibody that competes for binding to CD73 with a control (e.g., 7H10). Preferably, such a test antibody will reduce the binding of the control antibody (e.g., 7H10) to the CD73 antigen by at least about 50% (e. g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the CD73 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

The antibodies will bind to CD73-expressing cells from an individual or individuals with a disease characterized by expression of CD73-positive cells, i.e. an individual that is a candidate for treatment with one of the herein-described methods using an anti-CD73 antibody of the invention. Accordingly, once an antibody that specifically recognizes CD73 on cells is obtained, it can optionally be tested for its ability to bind to CD73-positive cells (e.g. cancer cells). In particular, prior to treating a patient with one of the present antibodies, one may optionally test the ability of the antibody to bind malignant cells taken from the patient, e.g. in a blood sample or tumor biopsy, to maximize the likelihood that the therapy will be beneficial in the patient.

In one embodiment, the antibodies of the invention are validated in an immunoassay to test their ability to bind to CD73-expressing cells, e.g. malignant cells. For example, a blood sample or tumor biopsy is performed and tumor cells are collected. The ability of a given antibody to bind to the cells is then assessed using standard methods well known to those in the art. Antibodies may bind for example to a substantial proportion (e.g., 20%, 30%, 40%, 50%, 60%, 70%, 80% or more) of cells known to express CD73, e.g. tumor cells, from a significant percentage of individuals or patients (e.g., 10%, 20%, 30%, 40%, 50% or more). Antibodies can be used for diagnostic purposes to determine the presence or level of malignant cells in a patient, for example as a biomarker to assess whether a patient is suitable for treatment with an anti-CD73 agent, or for use in the herein-described therapeutic methods. To assess the binding of the antibodies to the cells, the antibodies can either be directly or indirectly labeled. When indirectly labeled, a secondary, labeled antibody is typically added.

Determination of whether an antibody binds within an epitope region can be carried out in ways known to the person skilled in the art. As one example of such mapping/characterization methods, an epitope region for an anti-CD73 antibody may be determined by epitope "foot-printing" using chemical modification of the exposed amines/carboxyls in the CD73 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e. g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e. g., Ernst Schering Res Found Workshop. 2004; (44): 149-67; Huang et al., Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downard, J Mass Spectrom. 2000 April; 35 (4): 493-503 and Kiselar and Downard, Anal Chem. 1999 May 1; 71 (9): 1792-1801. Protease digestion techniques also can be useful in the context of epitope mapping and identification. Antigenic determinant-relevant regions/sequences can be determined by protease digestion, e.g. by using trypsin in a ratio of about 1:50 to CD73 or o/n digestion at and pH 7-8, followed by mass spectrometry (MS) analysis for peptide identification. The peptides protected from trypsin cleavage by the anti-CD73 binder can subsequently be identified by comparison of samples subjected to trypsin digestion and samples incubated with antibody and then subjected to digestion by e.g. trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the CD73 polypeptide that is not surface exposed and, accordingly, most likely not relevant in terms of immunogenicity/antigenicity.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence overall fold of the protein. See, e.g., Clackson and Wells, Science 1995; 267:383-386; and Wells, Proc Natl Acad Sci USA 1996; 93:1-6.

Electron microscopy can also be used for epitope "foot-printing". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fägerstam et al., Journal Of Molecular Recognition 1990; 3:208-14; Nice et al., J. Chroma-togr. 1993; 646:159-168; Leipert et al., Angew. Chem. Int. Ed. 1998; 37:3308-3311; Kröger et al., Biosensors and Bioelectronics 2002; 17:937-944.

It should also be noted that an antibody binding the same or substantially the same epitope as an antibody of the invention can be identified in one or more of the exemplary competition assays described herein.

Upon immunization and production of antibodies in a vertebrate or cell, particular selection steps may be performed to isolate antibodies as claimed. In this regard, in a specific embodiment, the invention also relates to methods of producing such antibodies, comprising: (a) immunizing a non-human mammal with an immunogen comprising a CD73 polypeptide; and (b) preparing antibodies from said immunized animal; and (c) selecting antibodies from step (b) that are capable of binding CD73.

Typically, an anti-CD73 antibody provided herein has an affinity for a CD73 polypeptide (e.g. as CD73 homodimers) in the range of about $10^7$ to about $10^{11}$ $M^{-1}$ (e.g., about $10^8$ to about $10^{11}$ $M^{-1}$). For example, in a particular aspect the invention provides Anti-CD73 antibody that have an average disassociation constant ($K_D$) of less than $1 \times 10^{-9}$ M with respect to CD73, as determined by, e.g., surface plasmon resonance (SPR) screening (such as by analysis with a BIAcore™ SPR analytical device). In a more particular exemplary aspect, the invention provides anti-CD73 antibodies that have a KD of about $1 \times 10^{-8}$ M to about $1 \times 10^{-10}$ M, or about $1 \times 10^{-9}$ M to about $1 \times 10^{-11}$ M, for CD73.

Antibodies can be characterized for example by a mean $K_D$ of no more than about (i.e. better affinity than) 100, 60, 10, 5, or 1 nanomolar, preferably sub-nanomolar or optionally no more than about 500, 200, 100 or 10 picomolar. $K_D$ can be determined for example for example by immobilizing recombinantly produced human CD73 proteins on a chip surface, followed by application of the antibody to be tested in solution. In one embodiment, the method further comprises a step (d), selecting antibodies from (b) that are capable of competing for binding to CD73 with antibody 7H10.

In one aspect of any of the embodiments, the antibodies prepared according to the present methods are monoclonal antibodies. In another aspect, the non-human animal used to produce antibodies according to the methods of the invention is a mammal, such as a rodent, bovine, porcine, fowl, horse, rabbit, goat, or sheep.

DNA encoding an antibody that binds an epitope present on CD73 polypeptides is isolated from a hybridoma and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding the monoclonal antibodies of the invention, e.g., antibody 7H10, 12F9, 15D7, 4B11, 11D9 or 9D2, can be readily isolated and sequenced using conventional procedures (e.g., by using oligonucleotide probes that are capable of binding specifically to genes encoding the heavy and light chains of murine antibodies). In one aspect, provided is a nucleic acid encoding a heavy chain or a light chain of an anti-CD73 antibody of any embodiment herein. Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody. In one embodiment, the invention comprises an isolated nucleic acid sequence encoding a light chain and/or a heavy chain of an antibody (e.g. 7H10, 12F9, 15D7, 4B11, 11D9 or 9D2), as well as a recombinant host cell comprising (e.g. in its genome) such nucleic acid. Recombinant expression in bacteria of DNA encoding the antibody is well known in the art (see, for example, Skerra et al., Curr. Opinion in Immunol., 5, pp. 256 (1993); and Pluckthun, Immunol. 130, p. 151 (1992).

Optionally, antibodies of the disclosure can be specified to be antibodies other than any one or more of antibodies 11E1, 8C7, 3C12 and 6E1 disclosed in PCT application no. WO2016/055609 (Innate Pharma), antibody 7G2 (Life Technologies Corp.), antibody 4G4 (Abcam, product ref. ab81720), antibody AD2 (Biolegend Corp, product ref. 344004), antibody 1E9 (Santa Cruz Biotechnology Corp., product sc-32299), 067-213 antibody described in US patent publication no. 2014/0235833, the anti-CD73 antibody referenced in Sachsenmeier et al. ((2012) J. Biomed. Screening 17:993-998 and/or in Rust et al. (2013) Mol. Cancer 12:11, or antibodies such as MEDI9447 (Medimmune Corp, Gaithersburg Md.) referenced in Huang et al. (2015) AACR Annual meeting; Abstract 1538, PCT publication no. WO2016/075099 and/or mAbs 11F11, 4C3, 4D4, 10D2, 11A6, 24H2, 5F8, 6E11, 7A11 or others referenced in PCT publication no. WO2016/081748, or related mAbs such as derivatives or parental and other mAbs of any the foregoing, for example mAbs Phen0203 CD730010 or CD730002 to CD730069, CD73.3 to CD73.11 e.g. mAbs that comprise the antigen binding region or heavy and/or light chain CDRs, in whole or in part. In other embodiments, the above-mentioned antibodies may, depending on the nature of the antibody, be modified so as to have the characteristics of the antibodies of the present disclosure.

Once antibodies are identified that are capable of binding CD73 and/or having other desired properties, they will also typically be assessed, using standard methods including those described herein, for their ability to bind to other polypeptides, including unrelated polypeptides. Ideally, the antibodies only bind with substantial affinity to CD73, and do not bind at a significant level to unrelated polypeptides, or other polypeptides of the 5'-nucleotidase family. However, it will be appreciated that, as long as the affinity for CD73 is substantially greater (e.g., 10×, 100×, 500×, 1000×, 10,000×, or more) than it is for other, unrelated polypeptides), then the antibodies are suitable for use in the present methods.

In one embodiment, the anti-CD73 antibodies can be prepared such that they do not have substantial specific binding to human Fcγ receptors, e.g., CD16. Such antibodies may comprise constant regions of various heavy chains that are known not to bind Fcγ receptors. One such example is a wild type human IgG4 constant region (IgG4 have minimal Fcγ receptor binding). A human IgG4 constant region can further comprise a stabilizing S228P (S241P) substitution) to retain bivalent binding ability in vivo by preventing Fab arm exchange. Alternatively, antibody fragments that do not comprise (or comprise portions of) constant regions, such as Fab or F(ab')2 fragments, can be used to avoid Fc receptor binding. Fc receptor binding can be assessed according to methods known in the art, including for example testing binding of an antibody to Fc receptor protein in a BIACORE assay. Also, generally any antibody IgG isotype can be used in which the Fc portion is modified (e.g., by introducing 1, 2, 3, 4, 5 or more amino acid substitutions) to minimize or eliminate binding to Fc receptors (see, e.g., WO 03/101485, the disclosure of which is herein incorporated by reference). Assays such as cell based assays, to assess Fc receptor binding are well known in the art.

In one embodiment, the antibody can comprise one or more specific mutations in the Fc region that result in "Fc silent" antibodies that have minimal interaction with effector cells. Silenced effector functions can be obtained by mutation in the Fc region of the antibodies and have been described in the art: N297A mutation, the LALA mutations, (Strohl, W., 2009, Curr. Opin. Biotechnol. vol. 20(6):685-691); and D265A (Baudino et al., 2008, J. Immunol. 181: 6664-69) see also Heusser et al., WO2012/065950, the disclosures of which are incorporated herein by reference. In one embodiment, an antibody comprises one, two, three or more amino acid substitutions in the hinge region. In one embodiment, the antibody is an IgG1 or IgG2 and comprises one, two or three substitutions at residues 233-236, optionally 233-238 (EU numbering). In one embodiment, the antibody is an IgG4 and comprises one, two or three substitutions at residues 327, 330 and/or 331 (EU numbering). Examples of silent Fc IgG1 antibodies are the LALA mutant comprising L234A and L235A mutation in the IgG1 Fc amino acid sequence. Another example of an Fc silent mutation is a mutation at residue D265, or at D265 and P329 for example as used in an IgG1 antibody as the DAPA (D265A, P329A) mutation (U.S. Pat. No. 6,737,056). Another silent IgG1 antibody comprises a mutation at residue N297 (e.g. N297A, N297S mutation), which results in aglycosylated/non-glycosylated antibodies. Other silent mutations include: substitutions at residues L234 and G237 (L234A/G237A); substitutions at residues S228, L235 and R409 (S228P/L235E/R409K,T,M,L); substitutions at residues H268, V309, A330 and A331 (H268Q/V309L/A330S/A331S); substitutions at residues C220, C226, C229 and P238 (C220S/C226S/C229S/P238S); substitutions at residues C226, C229, E233, L234 and L235 (C226S/C229S/E233P/L234V/L235A; substitutions at residues K322, L235 and L235 (K322A/L234A/L235A); substitutions at residues L234, L235 and P331 (L234F/L235E/P331S); substitutions at residues 234, 235 and 297; substitutions at residues E318, K320 and K322 (L235E/E318A/K320A/K322A); substitutions at residues (V234A, G237A, P238S); substitutions at residues 243 and 264; substitutions at residues 297 and 299; substitutions such that residues 233, 234, 235, 237, and 238 defined by the EU numbering system, comprise a sequence selected from PAAAP, PAAAS and SAAAS (see WO2011/066501), optionally further in combination with a substitution at Kabat residues 330 and/or 331. In one embodiment, the antibody comprises an Fc domain comprising an amino acid substitution at residues 234, 235 and 331, for example the "TM" mutation having substitutions L234F, L235E and P331S. In one embodiment, the antibody comprises an Fc domain comprising an amino acid substitution at residues 234, 235 and 322, or at residues 234, 235 and 331, described in US Patent publication no. US2015/0125444, wherein residue 234 is F (phenylalanine); residue 235 is Alanine (A), Asparagine (N), Phenylalanine (F), Glutamine (Q), or Valine (V); residue 322 is Alanine (A), Aspartic acid (D), Glutamic acid (E), Histidine (H), Asparagine (N), or Glutamine (Q); and residue 331 is Alanine (A) or Glycine (G). Amino acid residues are indicated according to EU numbering according to Kabat.

In one embodiment, the antibody comprises an Fc domain, optionally of human IgG1 isotype, comprising: a L234$X_1$ substitution, a L235$X_2$ substitution, and a P331$X_3$ substitution, wherein $X_1$ is any amino acid residue other than leucine, $X_2$ is any amino acid residue other than leucine, and $X_3$ is any amino acid residue other than proline; optionally wherein $X_1$ is an alanine or phenylalanine or a conservative substitution thereof; optionally wherein $X_2$ is glutamic acid or a conservative substitution thereof; optionally wherein $X_3$ is a serine or a conservative substitution thereof. In another embodiment, the antibody comprises an Fc domain, optionally of human IgG1 isotype, comprising: a L234$X_1$ substitution, a L235$X_2$ substitution, a G237$X_4$ substitution and a P331$X_4$ substitution, wherein $X_1$ is any amino acid residue other than leucine, $X_2$ is any amino acid residue other than leucine, $X_3$ is any amino acid residue other than glycine, and $X_4$ is any amino acid residue other than proline; optionally wherein $X_1$ is an alanine or phenylalanine or a conservative substitution thereof; optionally wherein $X_2$ is glutamic acid or a conservative substitution thereof; optionally, $X_3$ is alanine or a conservative substitution thereof; optionally $X_4$ is a serine or a conservative substitution thereof. In another embodiment, the antibody comprises an Fc domain, optionally of human IgG1 isotype, comprising: a L234$X_1$ substitution, a L235$X_2$ substitution, a G237$X_4$ substitution, G330$X_4$ substitution, and a P331$X_5$ substitution, wherein $X_1$ is any amino acid residue other than leucine, $X_2$ is any amino acid residue other than leucine, $X_3$ is any amino acid residue other than glycine, $X_4$ is any amino acid residue other than alanine, and $X_5$ is any amino acid residue other than proline; optionally wherein $X_1$ is an alanine or phenylalanine or a conservative substitution thereof; optionally wherein $X_2$ is glutamic acid or a conservative substitution thereof; optionally, $X_3$ is alanine or a conservative substitution thereof; optionally, $X_4$ is serine or a conservative substitution thereof; optionally $X_5$ is a serine or a conservative substitution thereof. In the shorthand notation used here, the format is: Wild type residue: Position in polypeptide: Mutant residue, wherein residue positions are indicated according to EU numbering according to Kabat. In one embodiment an Fc domain comprises substitutions at Kabat residues L234, L235 and P331 (e.g., a L234A/L235E/P331S or L234F/L235E/P331S mutation). Another example of such an Fc domain comprises substitutions at Kabat residues L234, L235, G237 and P331 (e.g., a L234A/L235E/G237A/P331S mutation). Another example of such an Fc domain comprises substitutions at Kabat residues L234, L235, G237, A330 and P331 (e.g., a L234A/L235E/G237A/A330S/P331S mutation).

In one embodiment, an antibody comprises a heavy chain constant region comprising the amino acid sequence below, or an amino acid sequence at least 90%, 95% or 99% identical thereto but retaining the amino acid residues at Kabat positions 234, 235 and 331 (underlined):

(SEQ ID NO: 104)
A S T K G P S V F P L A P S S K S T S G G T A A
L G C L V K D Y F P E P V T V S W N S G A L T S
G V H T F P A V L Q S S G L Y S L S S V V T V P
S S S L G T Q T Y I C N V N H K P S N T K V D K
R V E P K S C D K T H T C P P C P A P E A E G G
P S V F L F P P K P K D T L M I S R T P E V T C
V V V D V S H E D P E V K F N W Y V D G V E V H
N A K T K P R E E Q Y N S T Y R V V S V L T V L
H Q D W L N G K E Y K C K V S N K A L P A S I E
K T I S K A K G Q P R E P Q V Y T L P P S R E E
M T K N Q V S L T C L V K G F Y P S D I A V E W
E S N G Q P E N N Y K T T P P V L D S D G S F F
L Y S K L T V D K S R W Q Q G N V F S C S V M H
E A L H N H Y T Q K S L S L S P G K

In one embodiment, an antibody comprises a heavy chain constant region comprising the amino acid sequence below, or an amino acid sequence at least 90%, 95% or 99% identical thereto but retaining the amino acid residues at Kabat positions 234, 235 and 331 (underlined):

(SEQ ID NO: 105)
A S T K G P S V F P L A P S S K S T S G G T A A
L G C L V K D Y F P E P V T V S W N S G A L T S
G V H T F P A V L Q S S G L Y S L S S V V T V P
S S S L G T Q T Y I C N V N H K P S N T K V D K
R V E P K S C D K T H T C P P C P A P E F E G G
P S V F L F P P K P K D T L M I S R T P E V T C
V V V D V S H E D P E V K F N W Y V D G V E V H
N A K T K P R E E Q Y N S T Y R V V S V L T V L
H Q D W L N G K E Y K C K V S N K A L P A S I E
K T I S K A K G Q P R E P Q V Y T L P P S R E E
M T K N Q V S L T C L V K G F Y P S D I A V E W
E S N G Q P E N N Y K T T P P V L D S D G S F F
L Y S K L T V D K S R W Q Q G N V F S C S V M H
E A L H N H Y T Q K S L S L S P G K

In one embodiment, an antibody comprises a heavy chain constant region comprising the amino acid sequence below, or an amino acid sequence at least 90%, 95% or 99% identical thereto but retaining the amino acid residues at Kabat positions 234, 235, 237, 330 and 331 (underlined):

(SEQ ID NO: 106)
ASTKGPSVFPLAPSSKSTSGGTAA

LGCLVKDYFPEPVTVSWNSGALTS

GVHTFPAVLQSSGLYSLSSVVTVP

SSSLGTQTYICNVNHKPSNTKVDK

RVEPKSCDKTHTCPPCPAPEAE GA

PSVFLFPPKPKDTLMISRTPEVTC

VVVDVSHEDPEVKFNWYVDGVEVH

NAKTKPREEQYNSTYRVVSVLTVL

HQDWLNGKEYKCKVSNKALPS_S_IE

KTISKAKGQPREPQVYTLPPSREE

MTKNQVSLTCLVKGFYPSDIAVEW

ESNGQPENNYKTTPPVLDSDGSFF

LYSKLTVDKSRWQQGNVFSCSVMH

EALHNHYTQKSLSLSPGK

In one embodiment, an antibody comprises a heavy chain constant region comprising the amino acid sequence below, or a sequence at least 90%, 95% or 99% identical thereto but retaining the amino acid residues at Kabat positions 234, 235, 237 and 331 (underlined):

(SEQ ID NO: 107)
ASTKGPSVFPLAPSSKSTSGGTAA

LGCLVKDYFPEPVTVSWNSGALTS

GVHTFPAVLQSSGLYSLSSVVTVP

SSSLGTQTYICNVNHKPSNTKVDK

RVEPKSCDKTHTCPPCPAPEAE GA

PSVFLFPPKPKDTLMISRTPEVTC

VVVDVSHEDPEVKFNWYVDGVEVH

NAKTKPREEQYNSTYRVVSVLTVL

HQDWLNGKEYKCKVSNKALPASIE

KTISKAKGQPREPQVYTLPPSREE

MTKNQVSLTCLVKGFYPSDIAVEW

ESNGQPENNYKTIPPVLDSDGSFF

LYSKLTVDKSRWQQGNVFSCSVMH

EALHNHYTQKSLSLSPGK

Fc silent antibodies result in no or low ADCC activity, meaning that an Fc silent antibody exhibits an ADCC activity that is below 50% specific cell lysis. Preferably an antibody substantially lacks ADCC activity, e.g., the Fc silent antibody exhibits an ADCC activity (specific cell lysis) that is below 5% or below 1%.

In one embodiment, the antibody has a substitution at any one, two, three, four, five or more of residues selected from the group consisting of: 220, 226, 229, 233, 234, 235, 236, 237, 238, 243, 264, 268, 297, 298, 299, 309, 310, 318, 320, 322, 327, 330, 331 and 409 (EU numbering).

In one embodiment, the antibody comprises an Fc domain comprising an amino acid substitution that increases binding to human FcRn polypeptides in order to increase the in vivo half-life of the antibody. Exemplary mutations are described in Strohl, W., 2009, Curr. Opin. Biotechnol. vol. 20(6):685-691, the disclosure of which is incorporated herein by reference. Examples of substitutions used in antibodies of human IgG1 isotype are substitutions at residues M252, S254 and T256; substitutions at residues T250 and M428; substitutions at residue N434; substitutions at residues H433 and N434; substitutions at residues T307, E380 and N434; substitutions at residues T307, E380, and N434; substitutions at residues M252, S254, T256, H433, N434 and 436; substitutions at residue I253; substitutions at residues P257, N434, D376 and N434.

In one embodiment, the antibody comprises an Fc domain comprising an amino acid substitution that has decreased sensitivity to cleavage by proteases. Matrix metalloproteinases (MMPs) represent the most prominent family of proteinases associated with tumorigenesis. While cancer cells can express MMPs, the bulk of the extracellular MMP is provided by different types of stromal cells that infiltrate the tumor and each produce a specific set of proteinases and proteinase inhibitors, which are released into the extracellular space and specifically alter the milieu around the tumor. The MMPs present in the tumor microenvironment can cleave antibodies within the hinge region and may thus lead to the inactivation of therapeutic antibodies that are designed to function within the tumor site. In one embodiment, the Fc domain comprising an amino acid substitution has decreased sensitivity to cleavage by any one, two, three or more (or all of) of the proteases selected from the group consisting of: GluV8, IdeS, gelatinase A (MMP2), gelatinase B (MMP-9), matrix metalloproteinase-7 (MMP-7), stromelysin (MMP-3), and macrophage elastase (MMP-12). In one embodiment, the antibody decreased sensitivity to cleavage comprises an Fc domain comprising an amino acid substitution at residues E233-L234 and/or L235. In one embodiment, the antibody comprises an Fc domain comprising an amino acid substitution at residues E233, L234, L235 and G236. In one embodiment, the antibody comprises an Fc domain comprising an amino acid substitution such that E233-L234-L235-G236 sequence is replaced by P233-V234-A235 (G236 is deleted). See, e.g., WO99/58572 and WO2012087746, the disclosures of which are incorporated herein by reference.

An anti-CD73 antibody can at any desired stage be assessed for its ability to enhance T cell proliferation, for example by evaluating T cell proliferation in vitro following stimulation of proliferation with agonists of CD3/CD28 molecules, in the presence of CD39-expressing cells and ATP. Antibodies can be selected that have the ability to potently enhance T cell proliferation when T cell proliferation is stimulated in vitro in the presence of ATP. For example, B and T lymphocytes can be purified from peripheral blood and cultured in presence of anti-CD3/anti-CD28-coated beads (to induce T cell proliferation) and in the presence of ATP (to inhibit T cell proliferation). At the end of the culture, photomicrographs can be captured for each condition and MTS substrate (Promega) is added for two hours to assess the enzymatic activity of cells able to transform MTS substrate into formazan that will be quantified at 490 nm by optical density. This enzymatic activity is correlated with number of living cells and allows cell proliferation to be assessed. Ability of anti-CD73 antibodies to restore T cell proliferation in presence of ATP can be assessed by pre-incubating anti-CD73 antibodies on cells before addition of CD3/CD28 beads and ATP.

In one embodiment, anti-CD73 antibodies cause an increase in T cell proliferation in the presence of ATP of at least 40%, 50%, 100% or 200% compared to control in which anti-CD73 antibodies are not present.

The ability of an antibody to inhibit the enzymatic activity of soluble recombinant CD73 can also be tested in a cellular assay using CD73-expressing cells and AMP, where conversion of AMP to adenosine (and/or inhibition thereof) is detected directly (e.g. by measurement of substrates and products, i.e. AMP, adenosine and/or phosphate), or indirectly. In one example, AMP and/or adenosine are detected via HPLC before and after incubation of the test compound with soluble recombinant CD73 dimer. The inhibitory activity of an antibody can also be assessed in any of a number of other ways. For example, in an indirect assay, a luciferase-based reagent is used (e.g. CellTiter-Glo® system available from Promega), to detect the disappearance of AMP. The luciferase reaction in the assay is inhibited by AMP. Adding the CD73 enzyme to the reaction degrades the AMP, and relieves the inhibition, producing a detectable signal. Assays using soluble CD73 polypeptide will be include testing at conditions where the antibodies are provided at a substantial molar excess (e.g. 10-fold, 20-fold, 50-fold, 100-fold, etc.) to the CD73 polypeptide dimers. When provided in molar excess to the enzyme, the anti-CD73 antibodies will no longer be capable of forming multimeric complexes of antibodies and CD73 dimers; inhibition of the enzymatic activity of CD73 can then be assessed.

Antibody Epitopes

In one aspect, the antibodies bind substantially the same epitope as antibody 7H10, 12F9, 15D7, 4B11, 11D9 or 9D2. In one embodiment, the antibodies bind to an epitope of CD73 that at least partially overlaps with, or includes at least one residue in, the epitope bound by antibody 7H10, 12F9, 15D7, 4B11, 11D9 or 9D2. The residues bound by the antibody can be specified as being present on the surface of the of the CD73 polypeptide, e.g. in a CD73 polypeptide expressed on the surface of a cell.

Binding of anti-CD73 antibody to cells transfected with CD73 mutants can be measured and compared to the ability of anti-CD73 antibody to bind wild-type CD73 polypeptide (e.g., SEQ ID NOS: 1 or 2). A reduction in binding between an anti-CD73 antibody and a mutant CD73 polypeptide (e.g. a polypeptide comprising the substitutions of mutant 2 in the Examples herein) means that there is a reduction in binding affinity (e.g., as measured by known methods such FACS testing of cells expressing a particular mutant, or by Biacore testing of binding to mutant polypeptides) and/or a reduction in the total binding capacity of the anti-CD73 antibody (e.g., as evidenced by a decrease in Bmax in a plot of anti-CD73 antibody concentration versus polypeptide concentration). A significant reduction in binding indicates that the mutated residue is directly involved in binding to the anti-CD73 antibody or is in close proximity to the binding protein when the anti-CD73 antibody is bound to CD73.

In some embodiments, a significant reduction in binding means that the binding affinity and/or capacity between an anti-CD73 antibody and a mutant CD73 polypeptide (e.g. mutant 2, 4 or 5 in the Examples herein) is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type CD73 polypeptide. In certain embodiments, binding is reduced below detectable limits. In some embodiments, a significant reduction in binding is evidenced when binding of an anti-CD73 antibody to a mutant CD73 polypeptide is less than 50% (e.g., less than 45%, 40%, 35%, 30%, 25%, 20%, 15% or 10%) of the binding observed between the anti-CD73 antibody and a wild-type CD73 polypeptide.

In some embodiments, anti-CD73 antibodies are provided that exhibit significantly lower binding for a mutant CD73 polypeptide in which a residue in a segment comprising an amino acid residue bound by antibody 7H10, 12F9, 15D7, 4B11, 11D9 or 9D2 is substituted with a different amino acid.

Antibody VH/VL and CDR Sequences

The amino acid sequence of the heavy chain variable region of antibody 7H10 is listed as SEQ ID NO: 3, the amino acid sequence of the light chain variable region is listed as SEQ ID NO: 4. In a specific embodiment, the invention provides an antibody that binds essentially the same epitope or determinant as monoclonal antibodies 7H10; optionally the antibody comprises the hypervariable region of antibody 7H10. In any of the embodiments herein, antibody 7H10 can be characterized by the amino acid sequences and/or nucleic acid sequences encoding it. In one embodiment, the monoclonal antibody comprises the Fab or F(ab')$_2$ portion of 7H10. Also provided is a monoclonal antibody that comprises the heavy chain variable region of 7H10. According to one embodiment, the monoclonal antibody comprises the three CDRs of the heavy chain variable region of 7H10. Also provided is a monoclonal antibody that further comprises the variable light chain variable region of 7H10 or one, two or three of the CDRs of the light chain variable region of 7H10. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 7H10 are fused to an immunoglobulin constant region of the human IgG type, optionally a human constant region.

In another aspect, the invention provides an antibody, wherein the antibody comprises: a HCDR1 region of 7H10 comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a HCDR2 region of 7H10 comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a HCDR3 region of 7H10 comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a LCDR1 region of 7H10 comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a LCDR2 region of 7H10 comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a LCDR3 region of 7H10 comprising an amino acid sequence as set forth in Table A-1, or a sequence of at least 4, 5, 6, 7, 8, 9 or 10 contiguous amino acids thereof, optionally wherein one or more of these amino acids may be deleted or substituted by a different amino acid. The HCDR1, 2, 3 and LCDR1, 2, 3 sequences can optionally be specified as all (or each, independently) being those of the Kabat numbering system (as indicated in Table A-1 for each CDR), those of the Chotia numbering system as indicated in Table A-1 for each CDR), those of the IMGT numbering system as indicated in Table A for each CDR), or any other suitable numbering system.

In another aspect, the invention provides an antibody that binds human CD73, comprising:

(a) the hypervariable regions of the heavy chain variable region of SEQ ID NO: 3, optionally wherein one, two, three or more amino acids are substituted by a different amino acid; and (b) the hypervariable regions of the light chain variable region of SEQ ID NO: 4, optionally wherein one, two, three or more amino acids are substituted by a different amino acid.

In another aspect, the invention provides an antibody that binds human CD73, comprising:

(a) a heavy chain CDR 1 amino acid sequence as shown in any one of SEQ ID NOS: 5-7, optionally wherein one, two, three or more amino acids in a CDR may be substituted by a different amino acid;

(b) a heavy chain CDR 2 amino acid sequence as shown in any one of SEQ ID NOS: 8-10, optionally wherein one, two, three or more amino acids in a CDR may be substituted by a different amino acid;

(c) a heavy chain CDR 3 amino acid sequence as shown in any one of SEQ ID NOS: 11-13, optionally wherein one, two, three or more amino acids in a CDR may be substituted by a different amino acid;

(d) a light chain CDR 1 amino acid sequence as shown in any one of SEQ ID NOS: 14, 15 or 16, optionally wherein one, two, three or more amino acids in a CDR may be substituted by a different amino acid;

(e) a light chain CDR 2 amino acid sequence as shown in any one of SEQ ID NOS: 17 or 18, optionally wherein one, two, three or more amino acids in a CDR may be substituted by a different amino acid; and/or (f) a light chain CDR 3 amino acid sequence as shown in any one of SEQ ID NOS: 19 or 20, optionally wherein one, two, three or more amino acids in a CDR may be substituted by a different amino acid.

In another aspect of any of the embodiments herein, any of the CDRs 1, 2 and 3 of the heavy and light chains of 7H10 may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

The amino acid sequence of the heavy chain variable region of antibody 12F9 is listed as SEQ ID NO: 21, the amino acid sequence of the light chain variable region is listed as SEQ ID NO: 22. In a specific embodiment, the invention provides an antibody that binds essentially the same epitope or determinant as monoclonal antibodies 12F9; optionally the antibody comprises the hypervariable region of antibody 12F9. In any of the embodiments herein, antibody 12F9 can be characterized by the amino acid sequences and/or nucleic acid sequences encoding it. In one embodiment, the monoclonal antibody comprises the Fab or F(ab')$_2$ portion of 12F9. Also provided is a monoclonal antibody that comprises the heavy chain variable region of 12F9. According to one embodiment, the monoclonal antibody comprises the three CDRs of the heavy chain variable region of 12F9. Also provided is a monoclonal antibody that further comprises the variable light chain variable region of 12F9 or one, two or three of the CDRs of the light chain variable region of 12F9. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 12F9 are fused to an immunoglobulin constant region of the human IgG type, optionally a human constant region.

In another aspect, the invention provides an antibody, wherein the antibody comprises: a HCDR1 region of 12F9 comprising an amino acid sequence as set forth in Table A-2, or a sequence of at least 4, 5, 6, 7, 8, 9 or 10 contiguous amino acids thereof, optionally wherein one or more of these amino acids may be substituted by a different amino acid; a HCDR2 region of 12F9 comprising an amino acid sequence as set forth in Table A-2, or a sequence of at least 4, 5, 6, 7, 8, 9 or 10 contiguous amino acids thereof, optionally wherein one or more of these amino acids may be substituted by a different amino acid; a HCDR3 region of 12F9 comprising an amino acid sequence as set forth in Table A-2, or a sequence of at least 4, 5, 6, 7, 8, 9 or 10 contiguous amino acids thereof, optionally wherein one or more of these amino acids may be substituted by a different amino acid; a LCDR1 region of 12F9 comprising an amino acid sequence as set forth in Table A-2, or a sequence of at least 4, 5, 6, 7, 8, 9 or 10 contiguous amino acids thereof, optionally wherein one or more of these amino acids may be substituted by a different amino acid; a LCDR2 region of 12F9 comprising an amino acid sequence as set forth in Table A-2, or a sequence of at least 4, 5, 6, 7, 8, 9 or 10 contiguous amino acids thereof, optionally wherein one or more of these amino acids may be substituted by a different amino acid; a LCDR3 region of 12F9 comprising an amino acid sequence as set forth in Table A-2, or a sequence of at least 4, 5, 6, 7, 8, 9 or 10 contiguous amino acids thereof, optionally wherein one or more of these amino acids may be deleted or substituted by a different amino acid. The HCDR1, 2, 3 and LCDR1, 2, 3 sequences can optionally be specified as all (or each, independently) being those of the Kabat numbering system (as indicated in Table A-2 for each CDR), those of the Chotia numbering system as indicated in Table A-2 for each CDR), those of the IMGT numbering system as indicated in Table A-2 for each CDR), or any other suitable numbering system.

In another aspect, the invention provides an antibody that binds human CD73, comprising:

(a) the hypervariable regions of the heavy chain variable region of SEQ ID NO: 21, optionally wherein one, two, three or more amino acids are substituted by a different amino acid; and (b) the hypervariable regions of the light chain variable region of SEQ ID NO: 22, optionally wherein one, two, three or more amino acids are substituted by a different amino acid.

In another aspect, the invention provides an antibody that binds human CD73, comprising:

(a) a heavy chain CDR 1 amino acid sequence as shown in any one of SEQ ID NOS: 23-25, optionally wherein one, two, three or more amino acids in a CDR may be substituted by a different amino acid;

(b) a heavy chain CDR 2 amino acid sequence as shown in any one of SEQ ID NOS: 26-28, optionally wherein one, two, three or more amino acids in a CDR may be substituted by a different amino acid;

(c) a heavy chain CDR 3 amino acid sequence as shown in any one of SEQ ID NOS: 29-31, optionally wherein one, two, three or more amino acids in a CDR may be substituted by a different amino acid;

(d) a light chain CDR 1 amino acid sequence as shown in any one of SEQ ID NOS: 32-34, optionally wherein one, two, three or more amino acids in a CDR may be substituted by a different amino acid;

(e) a light chain CDR 2 amino acid sequence as shown in any one of SEQ ID NOS: 35-36, optionally wherein one, two, three or more amino acids in a CDR may be substituted by a different amino acid; and/or (f) a light chain CDR 3 amino acid sequence as shown in any one of SEQ ID NOS: 37-39, optionally wherein one, two, three or more amino acids in a CDR may be substituted by a different amino acid.

In another aspect of any of the embodiments herein, any of the CDRs 1, 2 and 3 of the heavy and light chains of 12F9 may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

The amino acid sequence of the heavy chain variable regions of antibodies 15D7, 4B11, 11D9 or 9D2 are listed as SEQ ID NOS: 40, 42, 44 and 46, and the respective amino acid sequence of the light chain variable regions of these antibodies are listed as SEQ ID NOS; 41, 43, 45 and 47, and as shown in Table B. In a specific embodiment, the invention provides an antibody that binds essentially the same epitope or determinant as monoclonal antibody 15D7, 4B11, 11D9 or 9D2; optionally the antibody comprises the hypervariable region of antibody 15D7, 4B11, 11D9 or 9D2. In any of the embodiments herein, antibody 15D7, 4B11, 11D9 or 9D2 can be characterized by the amino acid sequences and/or nucleic acid sequences encoding it. In one embodiment, the monoclonal antibody comprises the Fab or F(ab')₂ portion of 15D7, 4B11, 11D9 or 9D2. Also provided is a monoclonal antibody that comprises the heavy chain variable region of 15D7, 4B11, 11D9 or 9D2. According to one embodiment, the monoclonal antibody comprises the three CDRs (e.g., the CDR1, CDR2 and CDR3) of the heavy chain variable region of 15D7, 4B11, 11D9 or 9D2. Also provided is a monoclonal antibody that further comprises the variable light chain variable region of 15D7, 4B11, 11D9 or 9D2 or one, two or three of the CDRs (e.g., the CDR1, CDR2 and CDR3) of the light chain variable region of 15D7, 4B11, 11D9 or 9D2. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 15D7, 4B11, 11D9 or 9D2 are fused to an immunoglobulin constant region of the human IgG type, optionally a human constant region. The heavy chain variable domain CDRs and light chain CDRs of the antibodies are also provided in Table A-3a and A-3b, respectively.

In any of the antibodies of the invention, e.g., 7H10, 12F9, 15D7, 4B11, 11D9 or 9D2, the specified variable region and CDR sequences may comprise sequence modifications, e.g. a substitution (1, 2, 3, 4, 5, 6, 7, 8 or more sequence modifications). In one embodiment, a CDRs 1, 2 and/or 3 of the heavy and light chains comprises one, two, three or more amino acid substitutions, where the residue substituted is a residue present in a sequence of human origin. In one embodiment the substitution is a conservative modification. A conservative sequence modification refers to an amino acid modification that does not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the properties set forth herein) using the assays described herein.

In one embodiment, a heavy chain Kabat CDR1 can have an amino acid sequence that differs by at least one, two, three, four or more amino acid residue from the amino acid sequences SYNMY (SEQ ID NO: 93) and/or SYNMN (SEQ ID NO: 94). In one embodiment, a heavy chain Kabat CDR2 can have an amino acid sequence that differs by at least one, two, three, four or more amino acid residue from the amino acid sequences YIDPYNGGTSYNQKFKG (SEQ ID NO: 95), YIDPYNGGSSYNQKFKG (SEQ ID NO: 96) and/or YIDPYNGGSSYNLTFKG (SEQ ID NO: 97). In one embodiment, a heavy chain Kabat CDR3 can have an amino acid sequence that differs by at least one, two, three, four or more amino acid residue from the amino acid sequences GYGNYKAWFAY (SEQ ID NO: 98) and/or GYNNYKAWFAY (SEQ ID NO: 99). In one embodiment, a light chain Kabat CDR1 can have an amino acid sequence that differs by at least one, two, three, four or more amino acid residue from the amino acid sequences KASQSVTNDVA (SEQ ID NO: 100) and/or KASQSVSNDVA (SEQ ID NO: 101). In one embodiment, a light chain Kabat CDR2 can have an amino acid sequence that differs by at least one, two, three, four or more amino acid residue from the amino acid sequence YASNRYT (SEQ ID NO: 102). In one embodiment, a light chain Kabat CDR3 can have an amino acid sequence that differs by at least one, two, three, four or more amino acid residue from the amino acid sequence QQDYSSLT (SEQ ID NO: 103).

The sequences of the CDRs, according to IMGT, Kabat and Chothia definitions systems, have been summarized in Table A-1, A-2 and A-3a and A-3b below. The sequences of the variable regions of the antibodies according to the invention are listed in Table B below (if leader sequences are present any antibody chain can be specified to start at the amino acid position immediately following the end of the leader sequence), and each CDRs underlined. In any embodiment herein, a VL or VH sequence can be specified or numbered so as to contain or lack a signal peptide or any part thereof.

TABLE A-1

| | Antibody 7H10 | | | | | |
|---|---|---|---|---|---|---|
| CDR | HCDR1 | | HCDR2 | | HCDR3 | |
| definition | SEQ ID | Sequence | SEQ ID | Sequence | SEQ ID | Sequence |
| Kabat | 5 | SDYAWN | 8 | YIIYSGSTSYNPSLNS | 11 | EAYLYFDY |
| Chotia | 6 | GYSITSDY | 9 | YSG | 12 | AYLYFD |
| IMGT | 7 | GYSITSDYA | 10 | IIYSGST | 13 | AREAYLYFDY |
| CDR | LCDR1 | | LCDR2 | | LCDR3 | |
| definition | SEQ | Sequence | SEQ | Sequence | SEQ ID | Sequence |
| Kabat | 14 | RASQDINNYLN | 17 | YTSRLHS | 19 | QQGNTLPWT |
| Chotia | 15 | SQDINNY | 18 | YTS | 20 | GNTLPW |
| IMGT | 16 | QDINNY | 18 | YTS | 19 | QQGNTLPWT |

TABLE A-2

| | Antibody 12F9 | | | | | |
|---|---|---|---|---|---|---|
| CDR | HCDR1 | | HCDR2 | | HCDR3 | |
| definition | SEQ ID | Sequence | SEQ ID | Sequence | SEQ ID | Sequence |
| Kabat | 23 | NYYIH | 26 | WIYPGNVNTKYNEKFKG | 29 | EGGYDRYALDY |
| Chotia | 24 | GYTFTNY | 27 | PGNV | 30 | GGYDRYALD |
| IMGT | 25 | GYTFTNYY | 28 | IYPGNVNT | 31 | AREGGYDRYALDY |
| CDR | LCDR1 | | LCDR2 | | LCDR3 | |
| definition | SEQ | Sequence | SEQ | Sequence | SEQ ID | Sequence |
| Kabat | 32 | SASSSVSYMY | 35 | LTSNLAS | 37 | QQWSSNPLT |
| Chotia | 33 | SSSVSY | 36 | LTS | 38 | LTSWSSNPL |
| IMGT | 34 | SSVSY | 36 | LTS | 39 | QQWSSNPLT |

TABLE A-3a

| | | VH CDRS of antibodies 15D7, 1109 and 9D2 | | | | | |
|---|---|---|---|---|---|---|---|
| | CDR | HCDR1 | | HCDR2 | | HCDR3 | |
| mAb | definition | SEQ ID | Sequence | SEQ ID | Sequence | SEQ ID | Sequence |
| 15D7 | Kabat | 48 | SYWMH | 51 | EINPSNGRTNYNEKFKS | 52 | RGGYGNWFAY |
| | Chotia | 49 | GYTFTSY | 56 | PSNG | 53 | GGYGNWFA |
| | IMGT | 50 | GYTFTSYW | 92 | INPSNGRT | 54 | ARRGGYGNWFAY |
| 11D9 | Kabat | 55 | SYVMH | 58 | YINPYNDGTKYNEKFKG | 61 | WGYDEGYYYAMDY |
| | Chotia | 49 | GYTFTSY | 59 | PYND | 62 | GYDEGYYYAMD |
| | IMGT | 57 | GYTFTSYV | 60 | INPYNDGT | 63 | ARWGYDEGYYYAMDY |
| 9D2 | Kabat | 64 | SSYIS | 67 | WIYAGTGTTRYNQKFTG | 70 | HVNWDHFEY |
| | Chotia | 65 | GFTFSSS | 68 | AGTG | 71 | VNWDHFE |
| | IMGT | 66 | GFTFSSSY | 69 | IYAGTGTT | 72 | ARHVNWDHFEY |

TABLE A-3b

VL CDRS of antibodies 15D7, 11D9 and 9D2

| mAb | CDR definition | LCDR1 SEQ ID | Sequence | LCDR2 SEQ ID | Sequence | LCDR3 SEQ ID | Sequence |
|---|---|---|---|---|---|---|---|
| 15D7 | Kabat | 73 | KASQDINTYLS | 76 | RANRLVD | 78 | LQYDEFPYT |
| | Chotia | 74 | SQDINTY | 77 | RAN | 79 | YDEFPY |
| | IMGT | 75 | QDINTY | 77 | RAN | 78 | LQYDEFPYT |
| 11D9 | Kabat | 80 | KASQDINSYLS | 76 | RANRLVD | 83 | LQYDEFPLT |
| | Chotia | 81 | SQDINSY | 77 | RAN | 84 | YDEFPL |
| | IMGT | 82 | QDINSY | 77 | RAN | 83 | LQYDEFPLT |
| 9D2 | Kabat | 85 | KASQDVSTAVA | 88 | WASTRQT | 90 | QQYYRTPWT |
| | Chotia | 86 | SQDVSTA | 89 | WAS | 91 | YYRTPW |
| | IMGT | 87 | QDVSTA | 89 | WAS | 90 | QQYYRTPWT |

TABLE B

| | SEQ ID NO: | Amino Acid Sequence |
|---|---|---|
| 7H10 VH | 3 | DVQLQESGPGLVKPSQSLSLTCTVTGYSITSDYAWNWIRQFPGNKLEWMGYI IYSGSTSYNPSLNSRISITRDTSKNQFFLQLNSVTTEDTATYYCAREAYLYF DYWGQGTTLTVSS |
| 7H10 VL | 4 | DIQMTQTTSSLSASLGDRVTISCRASQDINNYLNWYQQKPDG TVKLLIYYTSRLHSGVPSRFSGSGSGTDYSLTISNLEREDVATYFCQQGNTL PWTFGGGTKLEIK |
| 12F9 VH | 21 | QVQLQQSGPELVKPGASVRISCKASGYTFTNYYIHWVKQRPGQGLEWIGWIY PGNVNTKYNEKFKGKATLTADKSSNTAYMQLSSLTSEDSAVYFCAREGGYDR YALDYWGQGTSVTVSS |
| 12F9 VL | 22 | QIVLTQSPALMSASPGEKVTMTCSASSSVSYMYWYQQKPRSSPKPWIYLTSN LASGVPARFSGSGSGTSYSLTISSMEAEDAATYYCQQWSSNPLTFGAGTKLE LK |
| 15D7 VH | 40 | QVQLQQPGAEVVKPGASVKLSCKASGYTFTSYWMHWVKQRPGQGLEWIGEIN PSNGRTNYNEKFKSKATLTVDKSSSTAYMQLSNLTSEDSAVYYCARRGGYGN WFAYWGQGTLVTVSA |
| 15D7 VL | 41 | DIKMTQSPSSMYASLGERVTITCKASQDINTYLSWFQQKPGKSPKTLIYRAN RLVDGVPSRFSGSGSGQDYSLTISSLEYEDMGIYYCLQYDEFPYTFGGGTKL EIK |
| 4B11 VH | 42 | QVQLQQSGPELVKPGASVRISCKASGYTFTNYYIHWVKQRPGQGLEWIGWIY PGNVNTKYNEKFKGKATLTADKSSNTAYMQLSSLTSEDSAVYFCAREGGYDR YALDYWGQGTSVTVSS |
| 4B11 VL | 43 | QIVLTQSPALMSASPGEKVTMTCSASSSVSYMYWYQQKPRSSPKPWIYLTSN LASGVPARFSGSGSGTSYSLTISSMEAEDAATYYCQQWSSNPLTFGAGTKLE LK |
| 11D9 VH | 44 | EVQLQQSGPELVKPGASVKMSCKASGYTFTSYVMHWVKQKPGQGLEWIGYIN PYNDGTKYNEKFKGKATLTSDKSSSTAYMELSSLTSEDSAVYYCARWGYDEG YYYAMDYWGQGTSVTVSS |
| 11D9 VL | 45 | DIVMTQSPSSMYASLGERVTITCKASQDINSYLSWFQQKPGKSPKTLIYRAN RLVDGVPSRFSGSGSGQDYSLTISSLEYEDMGIYYCLQYDEFPLTFGAGTKL ELK |
| 9D2 VH | 46 | QIQLQQSGAELVKPGASVNLSCKTSGFTFSSSYISWLKQKPGQSLEWIAWIY AGTGTTRYNQKFTGKAQLTVDTSSRTAYMQFSSLTTEDSAIYYCARHVNWDH FEYWGQGTTLTVSS |
| 9D2 VL | 47 | DIVMTQSHKFMATSVGDRVNITCKASQDVSTAVAWYQQKPGQSPKLLLYWAS TRQTGVPDHFTGSGSGTDYTLTINSVQADDLALYYCQQYYRTPWTFGGGTKL EIK |

Fragments and derivatives of antibodies (which are encompassed by the term "antibody" or "antibodies" as used in this application, unless otherwise stated or clearly contradicted by context) can be produced by techniques that are known in the art. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific (e.g. bispecific) antibodies formed from antibody fragments. Included, inter alia, are a nanobody, domain antibody, single domain antibody or a "dAb".

In certain embodiments, the DNA of a hybridoma producing an antibody, can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody.

Optionally an antibody is humanized. "Humanized" forms of antibodies are specific chimeric immunoglobulins, immunoglobulin chains or fragments thereof (such as Fv, Fab, Fab', F (ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.) Methods for humanizing the antibodies are well known in the art.

The choice of human variable domains, both light and heavy, to be used in making the humanized antibodies is very important to reduce antigenicity. According to the so-called "best-fit" method, the sequence of the variable domain of an antibody is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

In one embodiment, an antibody of the disclosure comprises a VH comprising a human framework region from a gene of a human V gene group selected from the group consisting of IGHV1-18, IGHV1-2, IGHV1-24, IGHV1-3, IGHV1-45, IGHV1-46, IGHV1-58, IGHV1-69, IGHV1-8, IGHV2-26, IGHV2-5, IGHV2-70, IGHV2-70D, IGHV3-11, IGHV3-13, IGHV3-15, IGHV3-20, IGHV3-21, IGHV3-23, IGHV3-23D, IGHV3-30, IGHV3-30-3, IGHV3-30-5, IGHV3-33, IGHV3-43, IGHV3-43D, IGHV3-48, IGHV3-49, IGHV3-54, IGHV3-64, IGHV3-64D, IGHV3-66, IGHV3-7, IGHV3-72, IGHV3-73, IGHV3-74, IGHV3-9, IGHV3-NL1, IGHV4-28, IGHV4-30-1, IGHV4-30-2, IGHV4-30-4, IGHV4-31, IGHV4-34, IGHV4-38-2, IGHV 4-39, IGHV4-4, IGHV4-59, IGHV4-61, IGHV5-10-1, IGHV5-51, IGHV6-1, and IGHV7-4-1.

In one embodiment, an antibody of the disclosure comprises a VL comprising a human framework region from a gene of a human V gene group selected from the group consisting of IGKV1-12, IGKV1-13, IGKV1-16, IGKV1-27, IGKV1-33, IGKV1-39, IGKV1-5, IGKV1-6, IGKV1-8, IGKV1-9, IGKV1-NL1, IGKV1D-12, IGKV1D-13, IGKV1D-16, IGKV1D-17, IGKV1D-33, IGKV1D-39, IGKV1D43, IGKV1D8, IGKV2-24, IGKV2-28, IGKV2-29, IGKV2-30, IGKV2-40, IGKV2D-26, IGKV2D-28, IGKV2D-29, IGKV2D-30, IGKV2D-40, IGKV3-11, IGKV3-15, IGKV3-20, IGKV3D-11, IGKV3D-15, IGKV3D-20, IGKV3D-7, IGKV4-1, IGKV5-2, IGKV6-21 and IGKV6D-21.

It is further important that antibodies be humanized with retention of high affinity for CD73 and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (5), is achieved. In general, the CDR residues are directly and most substantially involved in influencing antigen binding.

Another method of making "humanized" monoclonal antibodies is to use a XenoMouse (Abgenix, Fremont, Calif.) as the mouse used for immunization. A XenoMouse is a murine host according that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed in the present application.

Antibody Formulations

An anti-CD73 antibody can be incorporated in a pharmaceutical formulation comprising in a concentration from 1 mg/ml to 500 mg/ml, wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In a another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment, the formulation further comprises a pharmaceutically acceptable preservative. In a further embodiment, the formulation further comprises an isotonic agent. In a further embodiment, the formulation also comprises a chelating agent. In a further embodiment of the invention the formulation further comprises a stabilizer. In a further embodiment, the formulation further comprises a surfactant. For convenience reference is made to Remington: The Science and Practice of Pharmacy, 19$^{th}$ edition, 1995.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing an antibody according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen. Administration of pharmaceutical compositions according to the invention may be through several routes of administration, for example, subcutaneous, intramuscular, intraperitoneal, intravenous, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Suitable antibody formulations can also be determined by examining experiences with other already developed therapeutic monoclonal antibodies. Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym and similar formulations may be used with the antibodies of this invention. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. In another embodiment, the antibody is supplied in a formulation comprising about 20 mM Na-Citrate, about 150 mM NaCl, at pH of about 6.0.

Diagnosis and Treatment of Malignancies

Methods of treating an individual, notably a human patient, using an anti-CD73 antibody as described herein are also provided for. In one embodiment, the invention provides for the use of an antibody as described herein in the preparation of a pharmaceutical composition for administration to a human patient. Typically, the patient suffers from, or is at risk for, cancer.

For example, in one aspect, the invention provides a method of restoring or potentiating the activity of lymphocytes in a patient in need thereof, comprising the step of administering a neutralizing anti-CD73 antibody to said patient. The antibody can be for example a human or humanized anti-CD73 antibody, which antibody reduces or abrogates the 5'-nucleotidase activity of human CD73. In one embodiment, the method directed at increasing the activity of such lymphocytes in patients having a disease in which increased lymphocyte (e.g. T cell) activity is beneficial or which is caused or characterized by insufficient T cell activity, such as a cancer. The methods will be particularly useful for example patients having a solid tumor in which it is suspected the tumor microenvironment (and CD73-mediated adenosine production therein) may contribute to lack of recognition by the immune system (immune escape). The tumor may, for example, be characterized by CD73-expressing T cells and/or B cells.

More specifically, the methods and compositions of the present invention are utilized for the treatment of a variety of cancers and other proliferative diseases. Because these methods operate by reducing adenosine that inhibits the anti-tumor activity of lymphocytes, they are applicable to a very broad range of cancers, including in particular solid tumors in which adenosine in the tumor microenvironment may play a strong role in suppressing the anti-tumor immune response. In one embodiment, a human patient treated with an anti-CD73 antibody of the invention has liver cancer, bone cancer, pancreatic cancer, skin cancer, cancer of the head or neck, breast cancer, lung cancer, non-small cell lung cancer (NSCLC), castrate resistant prostate cancer (CRPC), melanoma, uterine cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. The present invention is also applicable to treatment of metastatic cancers. Patients can be tested or selected for one or more of the above described clinical attributes prior to, during or after treatment.

The anti-CD73 antibodies can be used to treat individuals who are predicted or observed to be poor responders to (not sufficiently sensitive to) treatment with an agent that neutralizes the inhibitory activity of human PD-1. The terms "reduces the inhibitory activity of human PD-1", "neutralizes PD-1" or "neutralizes the inhibitory activity of human PD-1" refers to a process in which PD-1 is inhibited in its signal transduction capacity resulting from the interaction of PD-1 with one or more of its binding partners, such as PD-L1 or PD-L2. An agent that neutralizes the inhibitory activity of PD-1 decreases, blocks, inhibits, abrogates or interferes with signal transduction resulting from the interaction of PD-1 with one or more of its binding partners, such as PD-L1, PD-L2. Such an agent can thereby reduce the negative co-stimulatory signal mediated by or through cell surface proteins expressed on T lymphocytes, so as to enhance T-cell effector functions such as proliferation, cytokine production and/or cytotoxicity. In one embodiment, a poor responder to treatment with an agent that neutralizes the inhibitory activity of human PD-1 is an individual having a cancer (e.g. cancer type or profile) that is known to be non-responsive, minimally response, or not sufficiently responsive to treatment with an agent that neutralizes the inhibitory activity of human PD-1. In one embodiment, a poor responder to treatment with an agent that neutralizes the inhibitory activity of human PD-1 is an individual whose cancer tissue or cancer-adjacent tissue is characterized by insufficient or low levels of inflammation (e.g. compared to a reference). In one embodiment, a poor responder to treatment with an agent that neutralizes the inhibitory activity of human PD-1 is an individual who has received treatment an agent that neutralizes the inhibitory activity of human PD-1 and whose cancer has progressed. In one embodiment, an individual who is a poor responder or who has a cancer that is poorly responsive is an individual having a poor disease prognosis for treatment with an agent that neutralizes the inhibitory activity of PD-1. An individual having a poor response to treatment with an agent that neutralizes the inhibitory activity of PD-1 can, for example, be identified by a high or higher risk of cancer progression (e.g. compared to individuals having a good disease prognostic), based on one or more predictive factors. In one embodiment, a predictive factor(s) comprises presence of elevated numbers of CD73 expressing T cells and/or elevated levels of CD73-expressing cells or adenosine levels in the tumor microenvironment (in tumor or tumor adjacent tissues). In one embodiment, a predictive factor(s) comprises presence or absence of a mutation in one or more genes. In one embodiment, the mutation defines a neo-epitope recognized by a T cell. In one embodiment, the predictive factor(s) comprises level(s) of expression of one or more genes or proteins in tumor cells, e.g. PD-L1, decreased or elevated levels of PD-L1 on tumor cells. In one embodiment, the predictive factor(s) comprises level(s) of expression of one or more genes or proteins in effector T cells in circulation or in the tumor environment, e.g., PD-1. In one embodiment, the predictive factor(s) comprises mutational load in tumor cells, e.g. number of non-synonymous mutations per exome.

In one embodiment, the active amount of an anti-CD73 antibody is an amount effective to achieve and/or maintain (e.g. for 1, 2, 3, or 4 weeks, and/or until the subsequent administration of anti-CD73 antibody) a blood concentration of at least the $EC_{50}$, optionally the $EC_{70}$, optionally substantially the $EC_{100}$, for inhibition of CD73-mediated catabolism of AMP to adenosine in an individual (e.g., as determined by assessing neutralization of 5' ectonucleotidase activity in MDA-MB-231 cells by quantifying hydrolysis of AMP to adenosine). In one embodiment, the active amount of an anti-CD73 antibody is an amount effective to achieve the $EC_{50}$, optionally the $EC_{70}$, optionally substantially the $EC_{100}$, for inhibition of CD73-mediated catabolism of AMP to adenosine in an extravascular tissue of an individual. In one embodiment, the active amount an anti-CD73 antibody is an amount effective to achieve the $EC_{50}$, optionally the $EC_{70}$, optionally substantially the $EC_{100}$, for inhibition of CD73-mediated catabolism of AMP to adenosine in an individual.

In some embodiments, an amount of anti-CD73 antibody is administered so as to obtain a concentration in blood (serum) or an extravascular tissue (e.g. tumor environment) that corresponds to at least the $EC_{70}$ or the $EC_{100}$ for neutralization of the enzymatic activity of CD73. The antibody can for example be administered in an amount to achieve and/or maintained a blood concentration or an extravascular tissue (e.g. tumor environment) of at least about 1 µg/ml, 2 µg/ml, 10 µg/ml, or 20 µg/ml.

In some embodiments, an amount of anti-CD73 antibody is administered so as to obtain a concentration in blood (serum) or an extravascular tissue (e.g. tumor environment) that corresponds to at least the $EC_{50}$, the $EC_{70}$ or the $EC_{100}$ for reversion of inhibition of proliferation of TCR co-stimulated T cells. In one embodiment, the $EC_{50}$, $EC_{70}$ or the $EC_{100}$ can be assessed for example in a cellular assay for reversion of inhibition of proliferation of TCR co-stimulated T cells, where the anti-CD73 antibody is brought into contact with T cells co-cultured with CD39-expressing B cells, wherein the T cells are induced to proliferate in vitro by TCR co-stimulation in the presence of ATP (e.g. at least 60 µM), and T cell proliferation is assessed at about 3 days following induction of proliferation.

"$EC_{50}$" with respect to neutralization of the enzymatic activity of CD73 or reversion of inhibition of proliferation, refers to the efficient concentration of anti-CD73 antibody which produces 50% of its maximum response or effect with respect to neutralization of the enzymatic activity or reversion of inhibition of proliferation, respectively). "$EC_{70}$" with respect to neutralization of the enzymatic activity of CD73 or reversion of inhibition of proliferation, refers to the efficient concentration of anti-CD73 antibody which produces 70% of its maximum response or effect. "$EC_{100}$" with respect to neutralization of the enzymatic activity of CD73 or reversion of inhibition of proliferation, refers to the efficient concentration of anti-CD73 antibody which produces its substantially maximum response or effect with respect to such respective neutralization of the enzymatic activity or reversion of inhibition of proliferation.

In one embodiment, the active amount of anti-CD73 antibody is between 1 and 20 mg/kg body weight. In one embodiment, the active amount is administered to an individual weekly, every two weeks, monthly or every two months.

In one embodiment provided is a method of treating a human individual having a cancer, comprising administering to the individual an effective amount of an anti-CD73 antibody of the disclosure for at least one administration cycle (optionally at least 2, 3, 4 or more administration cycles), wherein the cycle is a period of eight weeks or less, wherein for each of the at least one cycles, one, two, three or four doses of the anti-CD73 antibody are administered at a dose of 1-20 mg/kg body weight. In one embodiment, the anti-CD73 antibody is administered by intravenous infusion.

Prior to or during a course of treatment with an anti-CD73 antibody of the disclosure, the presence of CD73-expressing cells, and/or adenosine, ADP and/or AMP levels can be assessed within and/or adjacent to a patient's tumor to assess whether the patient is suitable for treatment (e.g. to predict whether the patient is likely to respond to treatment). The presence of CD73-expressing cells, and/or Increased levels of adenosine, ADP and/or AMP may indicate an individual is suitable for treatment with (e.g. likely to benefit from) an anti-CD73 antibody of the disclosure (including but not limited to an antibody that inhibits substrate-bound CD73).

Prior to or during a course of treatment with an anti-CD73 antibody of the disclosure, adenosine, ADP and/or AMP levels can be assessed within and/or adjacent to a patient's tumor to assess whether the patient is benefiting from treatment with an anti-CD73 antibody. Decreased levels of adenosine, ADP and/or AMP compared following an administration (or dosing of antibody) compared to levels prior to treatment (or dosing of antibody) may indicate an individual is benefiting from treatment with an anti-CD73 antibody of the disclosure (including but not limited to an antibody that inhibits substrate-bound CD73). Optionally, if a patient is benefiting from treatment with the anti-CD73 antibody, methods can further comprise administering a further dose of the anti-CD73 antibody to the patient (e.g., continuing treatment).

In one embodiment, assessing the presence of CD73-expressing cells, and/or adenosine, ADP and/or AMP levels within and/or adjacent to a patient's tumor the tissue sample comprises obtaining from the patient a biological sample of a human tissue selected from the group consisting of tissue from a cancer patient, e.g., cancer tissue, tissue proximal to or at the periphery of a cancer, cancer adjacent tissue, adjacent non-tumorous tissue or normal adjacent tissue, and detecting the presence of CD73-expressing cells, and/or adenosine, ADP and/or AMP levels within the tissue. The number of cells and/or levels from the patient can be comparing the level to a reference level, e.g. corresponding to a healthy individual.

In one embodiment, the disclosure provides a method for the treatment or prevention of a cancer in an individual in need thereof, the method comprising:

a) detecting CD73-expressing cells (or adenosine, ADP and/or AMP) the tumor environment, optionally within the tumor and/or within adjacent tissue, and b) upon a determination that tumor environment comprises CD73-expressing cells (or adenosine, ADP and/or AMP), optionally at a level that is increased compared to a reference level, administering to the individual an anti-CD73 antibody. Optionally, detecting CD73-expressing cells (or adenosine, ADP and/or AMP) within the tumor environment comprises obtaining from the individual a biological sample that comprises cancer tissue and/or tissue proximal to or at the periphery of a cancer (e.g., cancer adjacent tissue, adjacent non-tumorous tissue or normal adjacent tissue), and detecting levels of CD73-expressing cells (or adenosine, ADP and/or AMP). CD73-expressing cells may comprise, for example, tumor cells, T cells, B cells.

A patient having a cancer can be treated with the anti-CD73 antibody with our without a prior detection step to assess expression of CD73 on cells in the tumor microenvironment (e.g. on tumor cells, T cells, B cells, dendritic cells). Optionally, the treatment methods can comprises a step of detecting a CD73 nucleic acid or polypeptide in a biological sample of a tumor from an individual (e.g., in cancer tissue, tissue proximal to or at the periphery of a cancer, cancer adjacent tissue, adjacent non-tumorous tissue normal adjacent tissue). A determination that a biological sample comprises cells expressing CD73 (e.g. prominently expressing; expressing CD73 at a high level, high intensity of staining with an anti-CD73 antibody, compared to a reference) indicates that the patient has a cancer that may have a strong benefit from treatment with an agent that inhibits CD73. In one embodiment, the method comprises determining the level of expression of a CD73 nucleic acid or polypeptide in a biological sample and comparing the level to a reference level corresponding to a healthy individual. A determination that a biological sample comprises cells expressing CD73 nucleic acid or polypeptide at a level that is increased compared to the reference level indicates that the patient has a cancer that can be treated with an anti-CD73 antibody of the disclosure. Optionally, detecting a CD73 polypeptide in a biological sample comprises detecting CD73 polypeptide expressed on the surface of a malignant cell, a T cell, a B cell, and/or a dendritic cell. In one embodiment, a determination that a biological sample comprises cells that prominently expresses CD73 nucleic acid or polypeptide indicates that the patients has a cancer that can be treated with an anti-CD73 antibody of the disclosure. "Prominently expressed", when referring to a CD73 polypeptide, means that the CD73 polypeptide is expressed in a substantial number of cells taken from a given patient. While the definition of the term "prominently expressed" is not bound by a precise percentage value, in some examples a receptor said to be "prominently expressed" will be present on at least 10%, 20% 30%, 40%, 50° %, 60%, 70%, 80%, or more of the tumor cells taken from a patient.

Determining whether an individual has a cancer characterized by cells that express a CD73 polypeptide can for example comprise obtaining a biological sample (e.g. by performing a biopsy) from the individual that comprises cells from the cancer environment (e.g. tumor or tumor adjacent tissue), bringing said cells into contact with an antibody that binds an CD73 polypeptide, and detecting whether the cells express CD73 on their surface. Optionally, determining whether an individual has cells that express CD73 comprises conducting an immunohistochemistry assay.

In one embodiment, the disclosure provides a method for the treatment or prevention of a cancer in an individual in need thereof, the method comprising:

a) determining the CD73 polypeptide status of cells within the tumor environment, optionally within the tumor and/or within adjacent tissue, and b) upon a determination that tumor environment comprises cells that express CD73 polypeptide, optionally at a level that is increased compared to a reference level, administering to the individual an anti-CD73 antibody. In one embodiment, the cells are tumor cells. In another embodiment, the cells within the tumor environment, tumor and/or adjacent tissue are non-malignant immune cells, e.g., T cells, B cells, dendritic cells. Optionally, determining the CD73 polypeptide status within the tumor environment comprises obtaining from the individual a biological sample that comprises cancer tissue and/or tissue proximal to or at the periphery of a cancer (e.g., cancer adjacent tissue, adjacent non-tumorous tissue or normal adjacent tissue), bringing said cells into contact with an antibody that binds a CD73 polypeptide, and detecting cells that express CD73.

The antibody compositions may be used in as monotherapy or combined treatments with one or more other therapeutic agents, including agents normally utilized for the particular therapeutic purpose for which the antibody is being administered. The additional therapeutic agent will normally be administered in amounts and treatment regimens typically used for that agent in a monotherapy for the particular disease or condition being treated. Such therapeutic agents include, but are not limited to anti-cancer agents and chemotherapeutic agents.

In one embodiment, the second or additional second therapeutic agent is an antibody or other Fc domain-containing protein capable of inducing ADCC toward a cell to which it is bound, e.g. via CD16 expressed by an NK cell. Typically, such protein will have an antigen binding domain that binds to an antigen of interest, e.g. an antigen expressed by a tumor cell (a tumor antigen) and an Fc domain or portion thereof and will exhibit binding to Fcγ receptors (e.g. CD16). In one embodiment, its ADCC activity will be mediated at least in part by CD16. In one embodiment, the additional therapeutic agent is an antibody having a native or modified human Fc domain, for example a Fc domain from a human IgG1 or IgG3 antibody. The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils. The term "ADCC-inducing antibody" refers to an antibody that demonstrates ADCC as measured by assay (s) known to those of skill in the art. Such activity is typically characterized by the binding of the Fc region with various FcRs. Without being limited by any particular mechanism, those of skill in the art will recognize that the ability of an antibody to demonstrate ADCC can be, for example, by virtue of it subclass (such as IgG1 or IgG3), by mutations introduced into the Fc region, or by virtue of modifications to the carbohydrate patterns in the Fc region of the antibody.

In one embodiment, the anti-CD73 neutralizing antibodies augment the efficacy of agents that neutralizes the inhibitory activity of human PD-1, e.g. that inhibits the interaction between PD-1 and PD-L1, notably in individuals who are poor responders to (or not sensitive to) treatment with agent that neutralizes the inhibitory activity of human PD-1. Accordingly, in one embodiment, the second or additional second therapeutic agent is an antibody or other agent that neutralizes the inhibitory activity of human PD-1.

In one embodiment, the second or additional second therapeutic agent is an agent that inhibits the CTLA-4 or PD-1 axis. PD-1 and CTLA-4 are inhibitory members of the CD28 family of receptors that also includes CD28, ICOS and BTLA. In one embodiment the second or additional second therapeutic agent is an antibody that binds and inhibits CTLA-4. In another embodiment, the second or additional second therapeutic agent is an agent (e.g., an antibody) that inhibits the PD-1 axis (i.e. inhibits PD-1 or PD-L1). Antibodies that bind CTLA-3, PD1 or PD-L1 can be used, for example, at the exemplary the doses and/or frequencies that such agents are used as monotherapy, e.g., as described below.

PD-1 is expressed on activated B cells, T cells, and myeloid cells Okazaki et al. (2002) Curr. Opin. Immunol. 14: 391779-82; Bennett et al. (2003) J Immunol 170:711-8). Two ligands for PD-1 have been identified, PD-L1 and PD-L2, that have been shown to downregulate T cell activation upon binding to PD-1 (Freeman et al. (2000) J Exp Med 192:1027-34; Latchman et al. (2001) Nat Immunol 2:261-8; Carter et al. (2002) Eur J Immunol 32:634-43). PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells. Immune suppression can be reversed by inhibiting the local interaction of PD-1 with PD-L1, and the effect is additive when the interaction of PD-1 with PD-L2 is blocked as well. Blockade of PD-1 can advantageously involve use of an antibody that prevents PD-L1-induced PD-1 signalling, e.g. by blocking the interaction with its natural ligand PD-L1. In one aspect the antibody binds PD-1 (an anti-PD-1 antibody); such antibody may block the interaction between PD-1 and PD-L1 and/or between PD-1 and PD-L2. In another aspect the antibody binds PD-L1 (an anti-PD-L1 antibody) and blocks the interaction between PD-1 and PD-L1.

There are currently at least six agents blocking the PD-1/PD-L1 pathway that are marketed or in clinical evaluation, any of these may be useful in combination with the anti- CD73 antibodies of the disclosure. One agent is BMS-936558 (Nivolumab/ONO-4538, Bristol-Myers Squibb; formerly MDX-1106). Nivolumab, (Trade name Opdivo®) is an FDA-approved fully human IgG4 anti-PD-L1 mAb that inhibits the binding of the PD-L1 ligand to both PD-1 and CD80 and is described as antibody 5C4 in WO 2006/121168, the disclosure of which is incorporated herein by reference. For melanoma patients, the most significant OR was observed at a dose of 3 mg/kg, while for other cancer types it was at 10 mg/kg. Nivolumab is generally dosed at 10 mg/kg every 3 weeks until cancer progression.

MK-3475 (human IgG4 anti-PD1 mAb from Merck), also referred to as lambrolizumab or pembrolizumab (Trade name Keytruda®) has been approved by the FDA for the treatment of melanoma and is being tested in other cancers. Pembrolizumab was tested at 2 mg/kg or 10 mg/kg every 2 or 3 weeks until disease progression. DNA constructs encoding the variable regions of the heavy and light chains of the humanized antibodies h409AII have been deposited with the American Type Culture Collection Patent Depository (10801 University Blvd., Manassas, Va.). The plasmid containing the DNA encoding the heavy chain of h409A-I 1 was deposited on Jun. 9, 2008 and identified as 081469_SPD-H and the plasmid containing the DNA encoding the light chain of h409AI 1 was deposited on Jun. 9, 2008 and identified as 0801470_SPD-L-I 1.

MPDL3280A/RG7446 (anti-PD-L1 from Roche/Genentech) is a human anti-PD-L1 mAb that contains an engineered Fc domain designed to optimize efficacy and safety by minimizing FcγR binding and consequential antibody-dependent cellular cytotoxicity (ADCC). Doses of ≤10, 15, and 25 mg/kg MPDL3280A were administered every 3 weeks for up to 1 year. In phase 3 trial, MPDL3280A is administered at 1200 mg by intravenous infusion every three weeks in NSCLC.

AMP-224 (Amplimmune and GSK) is an immunoadhesin comprising a PD-L2 extracellular domain fused to an Fc domain.

Pidlizumab (CT-011; CureTech) (humanized IgG1 anti-PD1 mAb from CureTech/Teva), Pidlizumab (CT-011; CureTech) (see e.g., WO2009/101611) Thirty patients with rituximab-sensitive relapsed FL were treated with 3 mg/kg intravenous CT-011 every 4 weeks for 4 infusions in combination with rituximab dosed at 375 mg/m2 weekly for 4 weeks, starting 2 weeks after the first infusion of CT-011.

Further known PD-1 antibodies and other PD-1 inhibitors include AMP-224 (a B7-DC/IgG1 fusion protein licensed to GSK), AMP-514 described in WO 2012/145493, antibody MEDI-4736 (an anti-PD-L1 developed by AstraZeneca/Medimmune) described in WO2011/066389 and US2013/034559, antibody YW243.55.570 (an anti-PD-L1) described in WO2010/077634, MDX-1105, also known as BMS-936559, is an anti-PD-L1 antibody developed by Bristol-Myers Squibb described in WO2007/005874, and antibodies and inhibitors described in WO2006/121168, WO2009/014708, WO2009/114335 and WO2013/019906, the disclosures of which are hereby incorporated by reference. Further examples of anti-PD1 antibodies are disclosed in WO2015/085847 (Shanghai Hengrui Pharmaceutical Co. Ltd.), for example antibodies having light chain variable domain CDR1, 2 and 3 of SEQ ID NO: 6, SEQ ID NO: 7 and/or SEQ ID NO: 8, respectively, and antibody heavy chain variable domain CDR1, 2 and 3 of SEQ ID NO: 3, SEQ ID NO: 4 or SEQ ID NO: 5, respectively, wherein the SEQ ID NO references are the numbering according to WO2015/085847, the disclosure of which is incorporated herein by reference. Antibodies that compete with any of these antibodies for binding to PD-1 or PD-L1 also can be used.

CTLA-4 (cytotoxic T-lymphocyte-associated protein 4), also known as CD152 is another inhibitory member of the CD28 family of receptors, and is expressed on T cells. Antibodies that bind and inhibit CTLA-4 are known in the art. In one example, the antibody is ipilimumab (trade name Yervoy®, Bristol-Myers Squibb), a human IgG antibody. An exemplary administration regimen for Yervoy is 3 mg/kg intravenously over 90 minutes every three weeks. In one example, the antibody used in combination with the anti-CD73 antibodies of the disclosure is an antibody that competes with ipilimumab for binding to CTLA-4.

In one embodiment, the second or additional second therapeutic agent is an agent that inhibits the CTLA-4 or PD-1 axis (e.g., an antibody that binds CTLA-4 or PD-L1) and additionally is capable of mediating ADCC, notably of cells that express CTLA-4 or PD-L1. See, e.g. Yervoy™ (anti-CTLA-4, Bristol-Myers Squibb Inc.), MPDL3280 (anti-PD-L1, Roche). In one embodiment, the antibody that binds human CTLA-4 or PD-L1 comprises a human Fc domain that binds CD16, optionally an Fc domain of human IgG1, IgG2 or IgG3 isotype that retains ability to bind human CD16. The anti-CD73 antibodies of the disclosure that enhance ADCC may enhance the activity of such antibodies by enhancing their ability to deplete cells that express CTLA-4 (e.g. TReg cell) or PD-L1 (e.g. tumor cells), respectively.

In another embodiment, the second or additional second therapeutic agent is an agent that binds and/or inhibits the GITR or OX-40 (e.g., an antibody that binds human GITR or human OX-40 and additionally is capable of mediating ADCC, notably of cells that express GITR or OX-40, respectively. ADCC-mediated effects have described for an anti-GITR antibody (GITR: glucocorticoid-induced TNFR-related protein) (Bulliard et al. (2013). J Exp Med 210:1685-93 and for anti-OX40 antibodies (Bulliard et al. (2014) Immunol Cell Biol. 92:475-80).

In the treatment methods, the CD73-binding compound and the second therapeutic agent can be administered separately, together or sequentially, or in a cocktail. In some embodiments, the antigen-binding compound is administered prior to the administration of the second therapeutic agent. For example, the CD73-binding compound can be administered approximately 0 to 30 days prior to the administration of the second therapeutic agent. In some embodiments, an CD73-binding compound is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the second therapeutic agent. In some embodiments, a CD73-binding compound is administered concurrently with the administration of the therapeutic agents. In some embodiments, a CD73-binding compound is administered after the administration of the second therapeutic agent. For example, a CD73-binding compound can be administered approximately 0 to 30 days after the administration of the second therapeutic agent. In some embodiments, a CD73-binding compound is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the second therapeutic agent.

EXAMPLES

Example 1: Generation of New Anti-huCD73 Antibodies

To obtain anti-human CD73 antibodies, Balb/c mice were immunized with a recombinant human CD73-His extracellular domain recombinant protein (cloned and produced at Innate Pharma as described below). Mice received one primo-immunization with an emulsion of 50 μg CD73 protein and Complete Freund Adjuvant, intraperitoneally, a 2nd immunization with an emulsion of 50 μg CD73 protein and Incomplete Freund Adjuvant, intraperitoneally, and finally a boost with 10 μg CD73 protein, intravenously. Immune spleen cells were fused 3 days after the boost with X63.Ag8.653 immortalized B cells, and cultured in the presence of irradiated spleen cells. Hybridomas were plated in semi-solid methylcellulose-containing medium and growing clones were picked using a clonepix 2 apparatus (Molecular Devices).

Primary screen: Supernatant (SN) of growing clones were tested in a primary screen by flow cytometry using parental and huCD73-, cynoCD73- or moCD73-expressing recombinant host cell lines. HuCD73- and cynoCD73-expressing cells were stained with 0.35 μM and 0.035 μM CFSE, respectively. For the flow cytometry screening, all cells were equally mixed and the presence of reacting antibodies in supernatants was revealed by Goat anti-mouse polyclonal antibody (pAb) labeled with PE. 47 antibodies were found to bind both human and cynomolgus CD73. All antibodies that bound huCD73 and cynoCD73 were produced as chimeric human IgG1 antibodies with a heavy chain N297Q (Kabat EU numbering) mutation which results in lack of N-linked glycosylation and lack of binding to Fcγ receptors.

Secondary screen: this informative screen (see Example 2) was done on recombinant CD73 protein to evaluate the CD73 enzymatic activity blockade properties of the 47-selected antibodies. 35/47 antibodies appear to completely or partially block CD73 activity.

Cloning, production and purification of recombinant huCD73

Molecular Biology

The huCD73 protein was cloned from MIAPACA-2 cDNA using the following primers TACGACT-CACAAGCTTGCCGCCAC-CATGTGTCCCCGAGCCGCGCG_For and CCGCCCCGACTCTAGAtcaGTGATGGTGAT-GATGGTGcttgatccgaccttcaactg_Rev. The purified PCR product was then cloned into an expression vector using the InFusion cloning system. A 6×His tag was added in the C-terminal part of the protein for the purification step.

Amino Acid Sequence of the Cloned huCD73:

(SEQ ID NO: 2)
MCPRAARAPATLLLALGAVLWPAA

GAWELTILHTNDVHSRLEQTSEDS

SKCVNASRCMGGVARLFTKVQQIR

RAEPNVLLLDAGDQYQGTIWFTVY

KGAEVAHFMNALRYDAMALGNHEF

DNGVEGLIEPLLKEAKFPILSANI

KAKGPLASQISGLYLPYKVLPVGD

-continued
EVVGIVGYTSKETPFLSNPGTNLV

FEDEITALQPEVDKLKTLNVNKII

ALGHSGFEMDKLIAQKVRGVDVVV

GGHSNTFLYTGNPPSKEVPAGKYP

FIVTSDDGRKVPVVQAYAFGKYLG

YLKIEFDERGNVISSHGNPILLNS

SIPEDPSIKADINKWRIKLDNYST

QELGKTIVYLDGSSQSCRFRECNM

GNLICDAMINNNLRHTDEMFWNHV

SMCILNGGGIRSPIDERNNGTITW

ENLAAVLPFGGTFDLVQLKGSTLK

KAFEHSVHRYGQSTGEFLQVGGIH

VVYDLSRKPGDRVVKLDVLCTKCR

VPSYDPLKMDEVYKVILPNFLANG

GDGFQMIKDELLRHDSGDQDINVV

STYISKMKVIYPAVEGRIKHHHHH

H

Expression and Purification of the huCD73 Proteins

After validation of the sequence cloned, recombinant host cells were nucleofected and the producing pool was then sub-cloned to obtain a cell clone producing the huCD73 protein. Supernatant from the huCD73 clone grown in roller was harvested and purified using Ni-NTA column and eluted using 250 mM imidazole. The purified proteins were then loaded onto a S200 size exclusion chromatography column. The purified protein corresponding to a dimer was formulated in a Tris 20 mM pH 7.5, NaCl 120 mM and $CaCl_2$) 4 mM buffer for enzyme activity assays, while formulation buffer is supplemented with 20% glycerol.

Example 2: Evaluation of Soluble CD73 Blockade

The ability of anti-CD73 antibodies to block enzymatic activity of CD73 was evaluated as described in Sachsenmeier et al. (J Biomol Screening, 2012). Briefly, 500 ng/ml of recombinant human CD73-his were incubated in white 96W flat bottom microplates in presence of dose-range of anti-CD73 or isotype control Abs. Plates were incubated for 1 h at 37° C. 12.5 μM ATP and 125 μM AMP were added to each well and plates are incubated at 37° C. for 30 supplemental minutes. Luciferase/luciferin-containing Cell Titer Glo (Promega) is added into wells, plates were incubated for 5 minutes at RT in the dark and emitted light is measured using an Enspire apparatus (Perkin Elmer).

Excess of AMP is known to block ATP-dependent luciferase activity. Addition of CD73 that cleaves AMP into adenosine+inorganic phosphate restores luciferase activity and light emission. Thus, antibodies that block enzymatic activity of CD73 will diminish light emission.

The percentage of enzyme inhibition is evaluated as described below:

Conditions:
ATP+AMP: maximal luciferase inhibition (100%)
ATP+AMP+CD73: no luciferase inhibition (0%)

Formula:
Residual CD73 activity:

$$\frac{(CD73 + Ab + ATP + AMP) - (ATP + AMP)}{(CD73 + ATP + AMP) - (ATP + AMP)} * 100$$

35 antibodies obtained in Example 1, as well as reference mAbs 7G2, 4G4 and 1E9, were all found to inhibit CD73 activity using this assay.

Considering the mixed results reported with reference antibodies, we considered whether CD73 blockade may arise from cross-linking of CD73 dimers by bivalent antibodies rather than true blockade of the enzymatic site. That is, antibodies may be causing oligomeric complexes of the CD73 dimers since bivalently binding mAbs may bind to two different CD73 homodimers, in turn leading to larger protein complexes). We then tested this possibility by performing blocking assays at high ratios of antibody:CD73 dimers. In this setting the mAbs are in large excess and induction of oligomeric complexes, permitting true CD73 functional blockade to be observed. In this setting antibodies no longer inhibit the enzymatic activity of CD73.

Figure 4A:
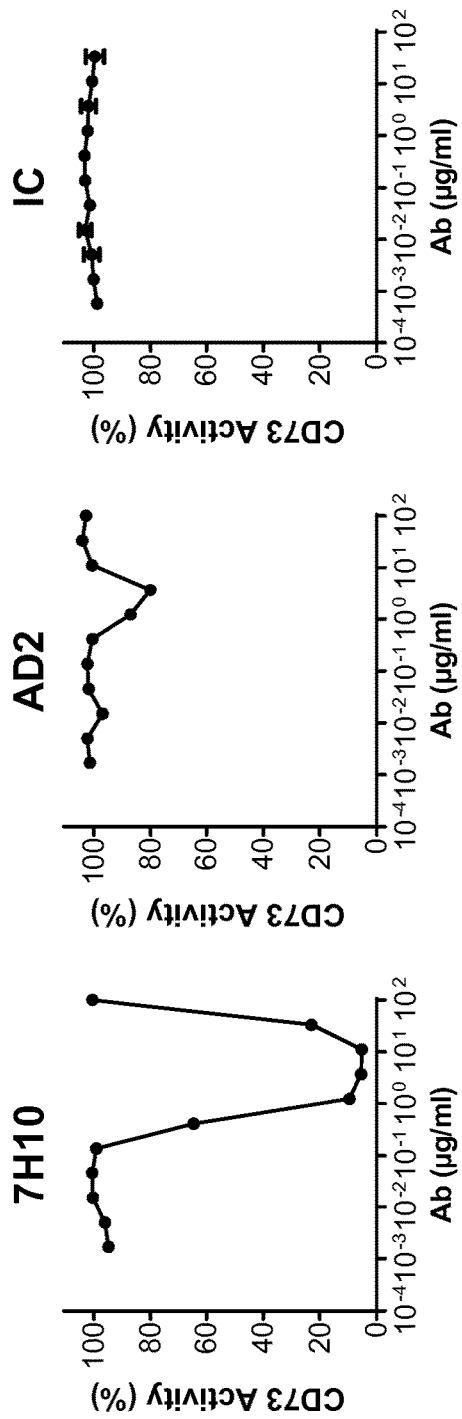
FIGS. 4A and 4B shows the ability of anti-CD73 antibodies to block enzymatic activity of CD73, assessed by measuring ability of test mAbs to affect CD73's ability to cleave AMP into adenosine+inorganic phosphate that restores luciferase activity and light emission. Results are expressed as residual enzyme activity (%). While antibodies 7H10 (FIG. 4A) and 12F9 (FIG. 4B) cause a strong decrease in enzyme activity, it no longer reduces enzyme activity when provided at excess (an immune-complex-independent setting). Antibody AD2 does not significantly reduce enzyme activity in any setting.
Figure 4B:
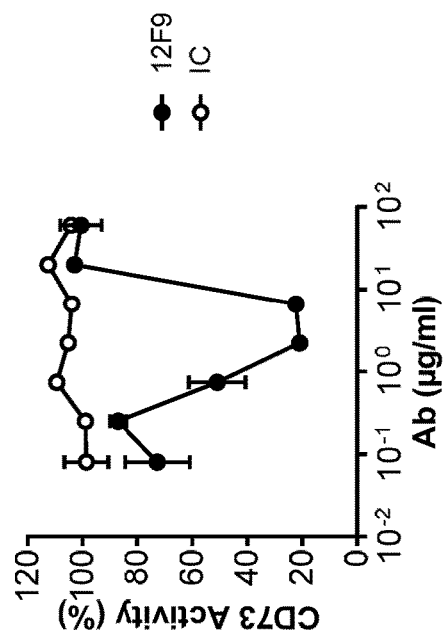

FIGS. 4A and 4B shows the ability of anti-CD73 antibodies to block enzymatic activity of CD73, assessed by measuring ability of test mAbs to affect CD73's ability to cleaves AMP into adenosine+inorganic phosphate that restores luciferase activity and light emission. Results are expressed as residual enzyme activity (%). As shown in FIG. 4A, while antibody 7H10 causes a strong decrease in enzyme activity, it no longer reduces enzyme activity when provided at excess (an immune-complex-independent setting). Antibody AD2 does not significantly reduce enzyme activity in any setting.

Shown in FIG. 4B, while antibody 12F9 initially causes a strong decrease in enzyme activity, it no longer reduced enzymatic activity when provided at excess over the CD73 enzyme (an immune-complex-independent setting). Other commercially available anti-CD73 reference antibodies reported in recent publications were also tested: AD2, 7G2, 4G4 and 1E9 were evaluated for CD73 blockade. Results showed that 7G2 blocked CD73 whereas AD2, 4G4 and 1E9 did not block CD73 activity, as residual enzyme activity rebounded to about the starting level or the negative control for the latter mAbs.

Example 3: Flow Cytometry Titration

Human-, cynomolgus- and mouse-CD73-expressing cell lines or human MDA-MB-231 breast adenocarcinoma that endogenously expresses CD73 were used to evaluate ability of anti-CD73 antibodies to bind human CD73 and to cross-react on cynomolgus and/or mouse CD73. $10^5$ cells resuspended in PBS/0.2% BSA/0.02% NaN3 (named "staining buffer") are distributed into round bottom 96W-microplates. Dose-range of anti-CD73 antibodies was added to the plates and cells are incubated for 45 min at 4° C. Cells were washed three times in staining buffer by spinning plates at 400 g for 3 min at 4° C. PE-coupled goat anti-mouse or goat anti-human IgG Fc fragment secondary antibodies (Beckman Coulter) diluted in staining buffer were added to the cells and plates and incubated for 30 additional minutes at 4° C. Cells were washed three times as described above and analyzed on an Accury C6 flow cytometer equipped with an HTFC plate reader.

Median of fluorescence vs. antibodies concentration was plotted on graphs and EC50 is calculated using GraphPad Prism program.

FIG. 1 shows results of titration of antibodies by flow cytometry on human CD73-expressing cell lines. As shown in FIG. 1, 7H10, bind to cells expressing human or cynomolgus (but not mouse) CD73 with excellent affinity. AD2 also bind to cells expressing human or cynomolgus CD73 but that requires an approximately 4 fold higher concentration ($EC_{50}$). The $EC_{50}$ for antibody 7H10 was 0.187 µg/ml for binding to cells expressing human CD73 and 0.335 µg/ml for binding to cells expressing cynomolgus CD73. The $EC_{50}$ for antibody AD2 was 0.743 µg/ml for binding to cells expressing human CD73 and 1.146 µg/ml for binding to cells expressing cynomolgus CD73. As shown in FIG. 1, 12F9 binds to cells expressing human or cynomolgus (but not mouse) CD73 with excellent affinity. The $EC_{50}$ for antibody 12F9 was 0.137 µg/ml for binding to cells expressing human CD73 and 0.527 µg/ml for binding to cells expressing cynomolgus CD73.

Figure 2:
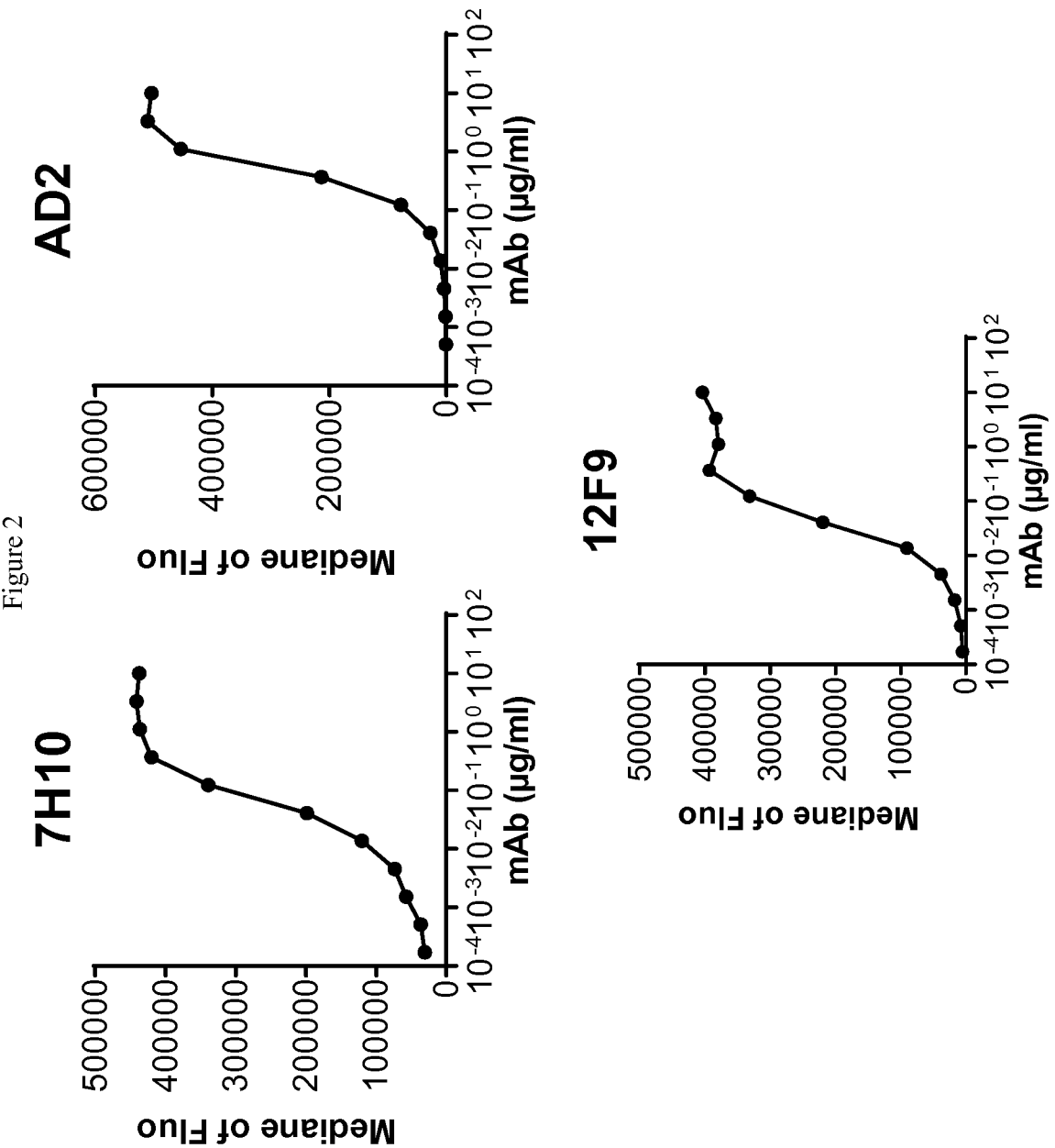
FIG. 2 shows results of titration of antibodies by flow cytometry human MDA-MB-231 breast adenocarcinoma cells that endogenously expresses CD73. 7H10 binds to MDA-MB-231 with an $EC_{50}$ that is about 8-fold lower than that of AD2.

FIG. 2 shows results of titration of antibodies by flow cytometry human MDA-MB-231 breast adenocarcinoma cells that endogenously expresses CD73. 7H10 binds to MDA-MB-231 with an $EC_{50}$ that is about 8-fold lower than that of AD2. The $EC_{50}$ for antibody 7H10 for binding to MDA-MB-231 cells was 0.054 µg/ml, while the $EC_{50}$ for antibody AD2 was 0.431 µg/ml. FIG. 2 also shows results of titration of antibodies by flow cytometry human MDA-MB-231 breast adenocarcinoma cells, where the $EC_{50}$ for antibody 12F9 for binding to MDA-MB-231 cells was 0.036 µg/ml.

Example 4: CD73 Down-Modulation

Human MDA-MB-231 breast adenocarcinoma cell line that endogenously expresses CD73 was used to evaluate the capacity of anti-CD73 antibodies to down regulate CD73 expression. MDA-MB-231 cells are available from ATCC (reference HTB-26). $10^5$ cells resuspended in staining buffer were distributed into flat bottom 96W-microplates. 10 µg/ml of anti-CD73 antibodies were added to the cells and plates are incubated at 4° C. or 37° C. for a time course. At T=10 min, 30 min, 1 h, 2 h, 3 h and 4 h, cells were recovered using PSB/2 mM EDTA, washed three times in staining buffer as prior described and incubated at 4° C. until end of the time course. 10 µg/ml of a AlexaFLuor 647-coupled non-competing anti-CD73 antibody were added to the cells and plates are incubated for 30 min at 4° C. Cells were washed three times and analyzed on an Accury C6 flow cytometer equipped with an HTFC plate reader.

Percentage of Expression Vs. Incubation Time is Plotted on Graphs.

Figure 5A:
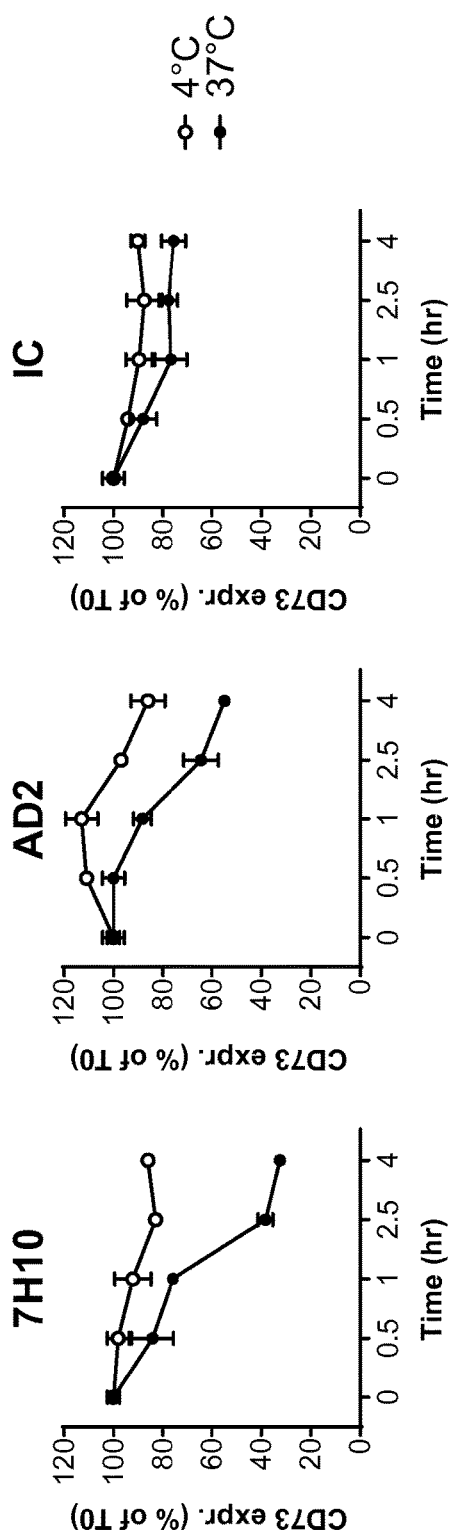
FIGS. 5A and 5B shows the ability of various antibodies to cause down-modulation of CD73 expression on the surface of cells. Both 7H10 and AD2 caused down-modulation of CD73, although 7H10 caused a stronger down-modulation of CD73 after 2.5 or 4 hours (FIG. 5A). Antibody 12F9 does not substantially increase or induce down-modulation of CD73 (FIG. 5B).
Figure 5B:
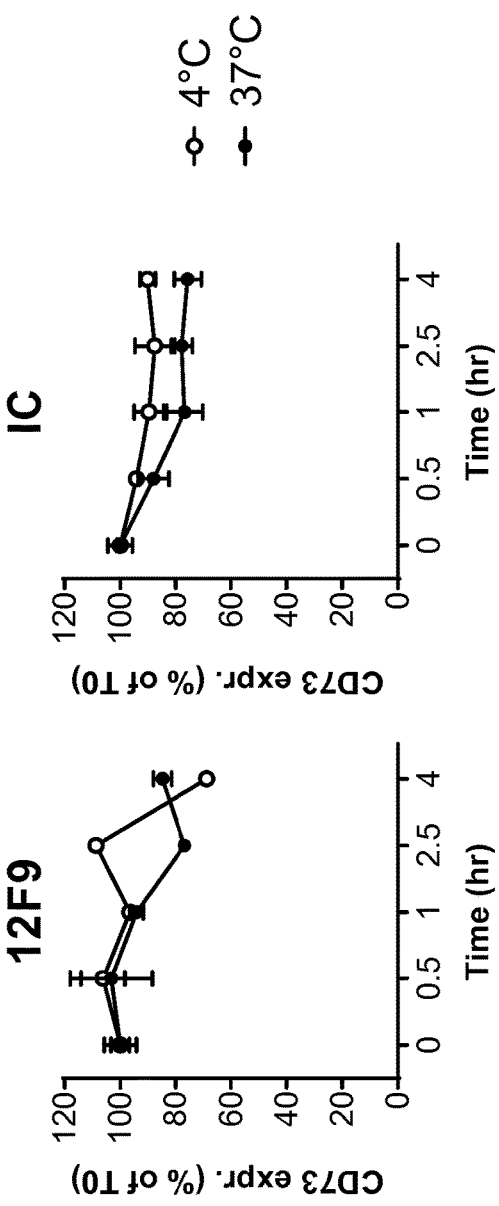

Antibody 7H10 was evaluated for its ability to cause downmodulation of CD73 expression on cells, and compared to reference mAb AD2. AD2 caused a decrease of well over 20% while 7H10 each caused a decrease in over 50% of receptor at the cell surface. Results are shown in FIG. 5A. Antibody 12F9 did not significantly reduce CD73 at the cell surface. Results are shown in FIG. 5B.

Example 5: Cellular CD73 Activity Blockade

The ability of anti-CD73 antibodies to neutralize the 5'-ectonucletidase enzymatic activity of cell-surface expressed CD73 was evaluated. The MDA-MB-231 tumor cell line was used a model tumor cell line that expresses CD73.

All reagents used in the experiment detailed below were diluted in TBS pH7.5 (Tris 20 mM pH7.5, NaCl 150 mM). MDA-MB-231 cell line is recovered in PBS-EDTA and washed twice in TBS pH7.5. 0.5 to $1 \times 10^5$ cells were plated in flat-bottom 96 well plates in presence of dose-range of anti-CD73 antibodies and incubated for 2 hours at 4° C. 200 mM AMP was added to the cells for a 30 minutes incubation period at 4° C. (to avoid CD73 down-modulation). Plates were then centrifuged and 50 µl supernatant are transferred in flat bottom 96 well culture plate. Free phosphate produced by the hydrolysis of AMP into adenosine was quantified using the Malachite Green Phosphate Detection Kit (R&D Systems) and following TDS provided by the manufacturer. Phosphate concentration vs. anti-CD73 Ab concentration was plotted in graphs and EC50 is calculated using Graph-Pad Prism software.

Figure 10:
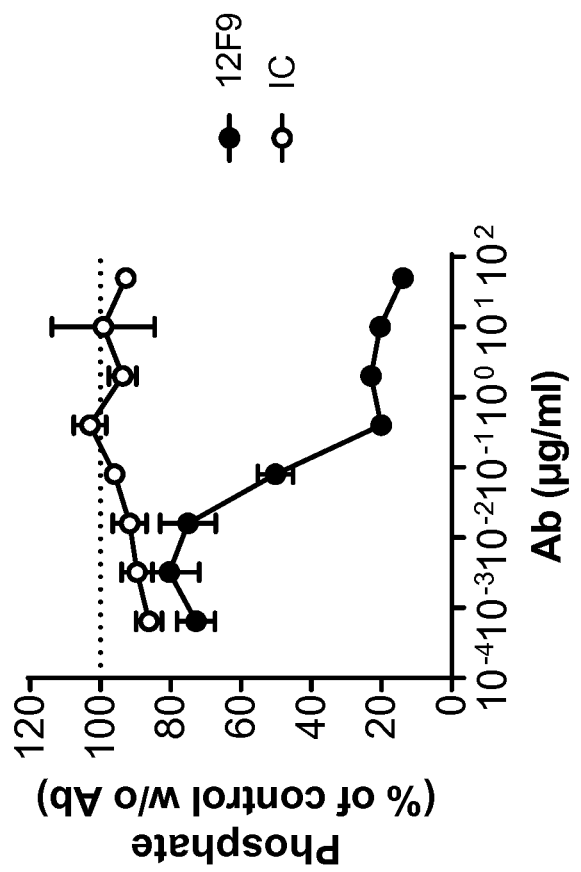
FIG. 10 shows antibody 12F9 neutralizes the enzymatic activity of cellular CD73 as determined by assessing neutralization of 5' ectonucleotidase activity in MDA-MB-231 cells by quantifying hydrolysis of AMP to adenosine.

Representative results are shown in FIG. 10, illustrating neutralized the enzymatic activity of cellular CD73 by for antibody 12F9, as determined by assessing neutralization of 5' ectonucleotidase activity in MDA-MB-231 cells by quantifying hydrolysis of AMP to adenosine.

Example 6: Reversion of T Cell Proliferation Inhibition by Antibodies 7H10, 12F9, 15D7, 4611, 11D9 and 9D2

Figure 6:
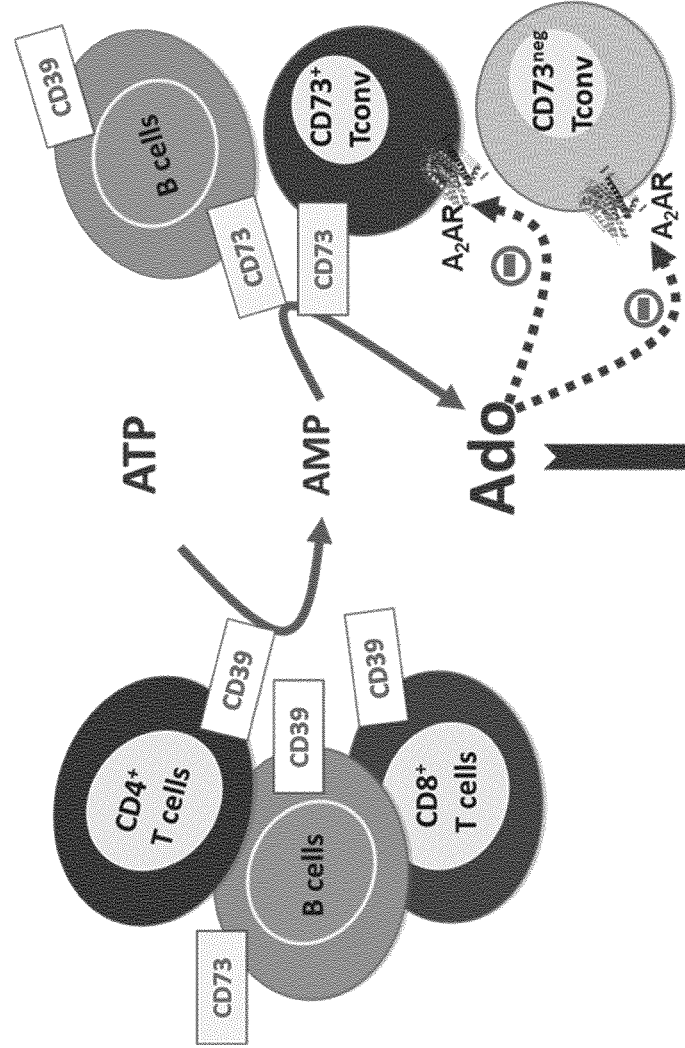
FIG. 6 shows T and B cell interactions (Tconv indicates conventional T cells) underlying the assay for reversion of inhibition of proliferation of TCR co-stimulated T cells.

Based on the study of the expression of CD39 and CD73 in human immune cells (in particular high CD39 expression on Treg and monocytes and CD73 expressed on minor CD4 T cell subset but high on B cell population) an assay was developed associating different immune cells and not only T cells (percoll gradient enriched in lymphocytes). The assay was performed both in ATP or AMP allowing the observation of a window to visualize CD73 activity much robustly in presence of ATP than AMP when the CD39/CD73 cooperation was needed. The read-out of the proliferation was based on three complementary methods: i) visual evaluation and quantification through photograph allowing kinetic evaluation of the proliferation, ii) revelation through MTS in the same well at the end of the culture, iii) in other independent assays using CTV dilution. For confirmation specific co-cultures between T reg and CD4 or CD8 effectors were performed (CTV revelation). The T and B cell interactions on which the assay is based in depicted in FIG. 6.

Figure 7A:
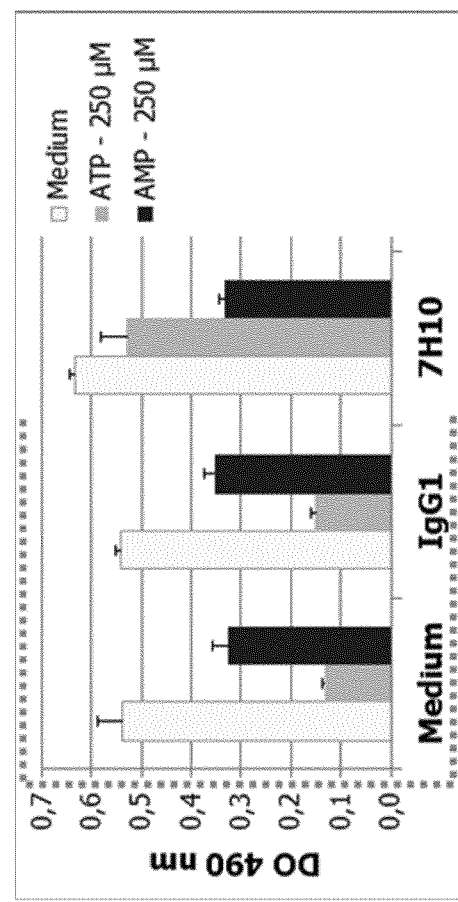
FIGS. 7A and 7B shows the effects on antibodies on reversion of inhibition of proliferation of TCR co-stimulated T cells in the presence of the exogenously added CD73 substrate AMP, or the exogenously added CD39 substrate ATP; shown on the left are photomicrographs for each condition and on the right, bar chart showing optical density (DO) for each condition. IC indicates isotype control. Antibodies 7H10 (FIG. 7A) and 12F9 (FIG. 7B) did not significantly increase T cell proliferation in the setting of exogenously added CD73 substrate AMP, but did increase T cell proliferation is the setting of exogenously added CD39 substrate ATP (without exogenously added CD73).
Figure 7A:
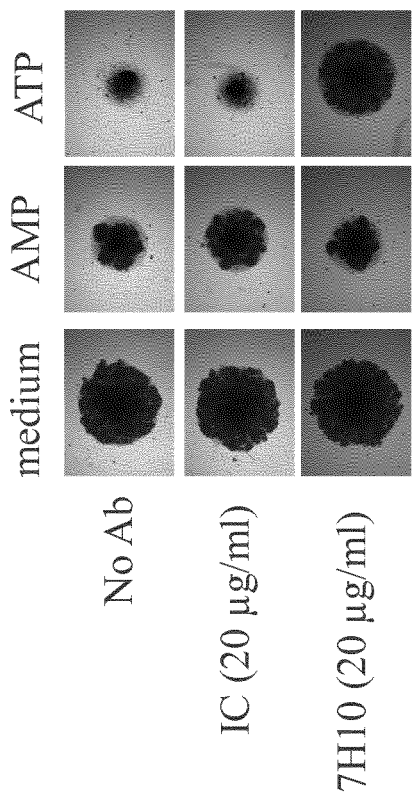
Figure 7B:
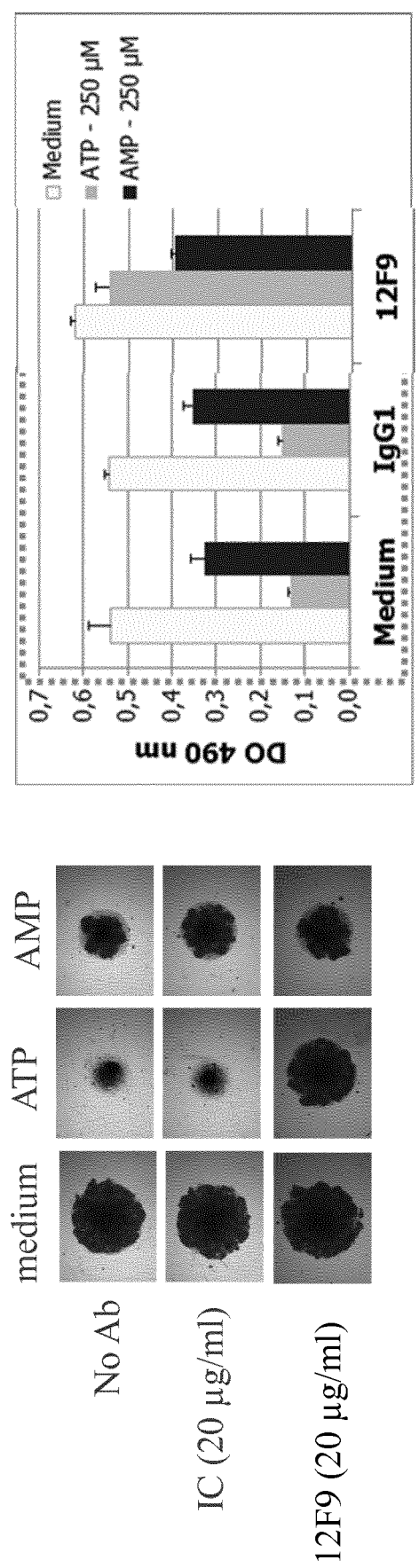

As an illustration of the improvement of the assay, antibodies were initially tested for effect on T cell proliferation in the presence of exogenously added CD73 substrate AMP. However, as shown in FIG. 7A, antibody 7H10 did not enhance T cell proliferation, showing that it does not reverse T cell proliferation inhibition in this setting. The same was observed for antibody 12F9, shown in FIG. 7B. However, as can be seen in FIGS. 7A and 7B, when exogenous ATP but not AMP is added in this co-culture setting, the T cell proliferation enhancement by the antibody can be revealed. It is possible that while processing of exogenously added AMP by CD73 occurs too rapidly for an effect on T cell proliferation to be observed, the constitutive generation of lower/physiological levels of AMP by CD39-expressing B cells (when supplied with exogenously added CD39 substrate ATP) could permit antibody-mediated inhibition of CD73 to be observed.

Peripheral blood from healthy donors was obtained and mononuclear cells were isolated using Ficoll centrifugation. B and T lymphocytes were further purified on a Percoll gradient. After collection of the percoll pellet containing the cells of interest, flow cytometry with specific antibodies (anti CD3, anti CD4, anti CD8, anti CD19 was performed to assess percentage of T (CD3, CD4 and CD8) and B (CD19) lymphocytes as well as their percentage and expression level of CD39 and CD73.

$5.10^4$ cells from "percoll pellet" were cultured in 96 round bottomed plates for 3 days in presence of antiCD3/antiCD28-coated beads (Life technologies) at a ratio 1 bead for 4 cells in triplicates to induce T cell proliferation. Inhibition of T cell proliferation was obtained by adding 62.5 µM ATP. At the end of the culture, photomicrographs were captured for each condition and MTS substrate (Promega) was added for two hours to assess the enzymatic activity of cells able to transform MTS substrate into formazan that will be quantified at 490 nm by optical density on a Tecan. This enzymatic activity is correlated with living cells number and allows to assess cell proliferation.

Ability of anti-CD73 antibodies to restore T cell proliferation in presence of ATP was assessed by pre-incubating Abs for 1 hour on cells before addition of CD3/CD28 beads activator as well as ATP.

Figure 8A:
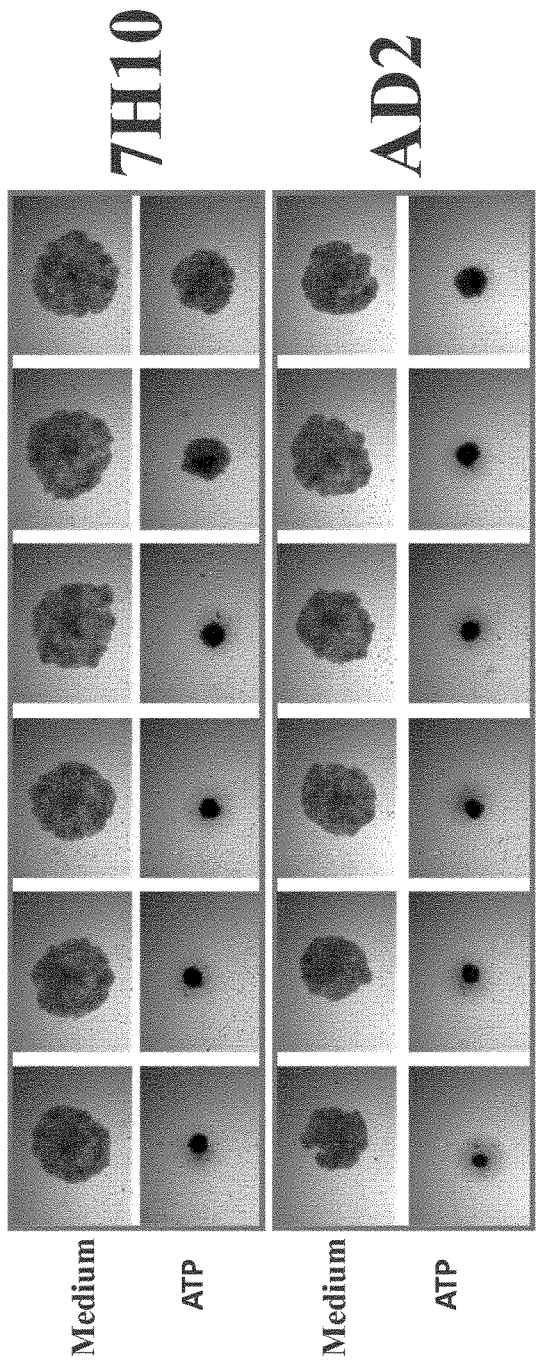
FIGS. 8A and 8B shows photomicrographs with increasing concentrations of antibodies 7H10 and 12F9 respectively, from left to right for each mAb.
Figure 8B:
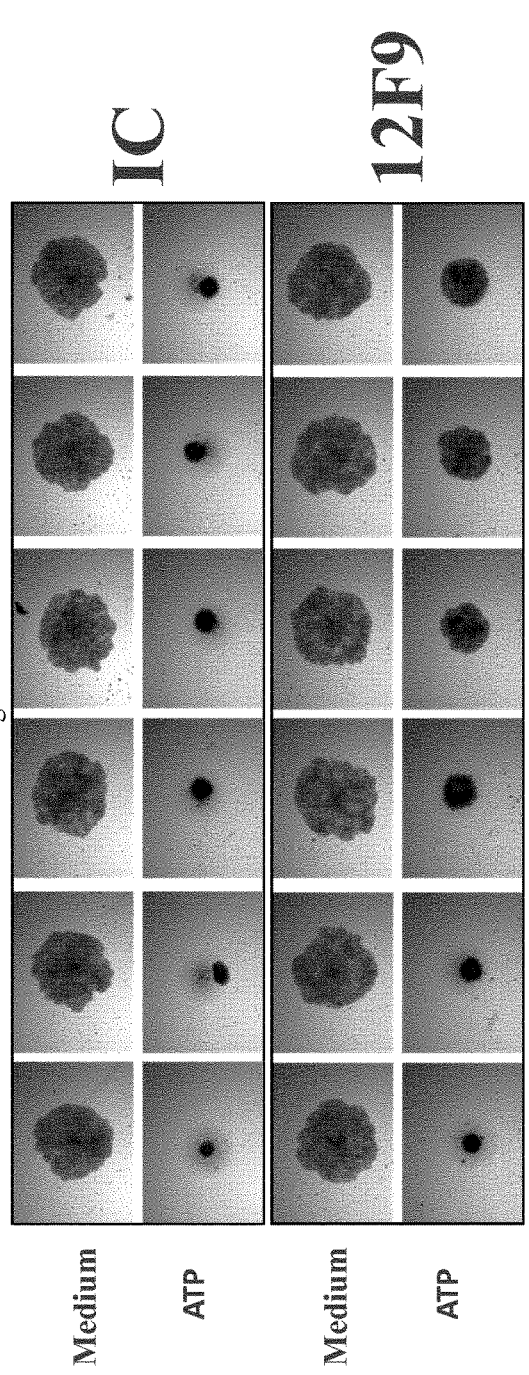
Figure 9A:
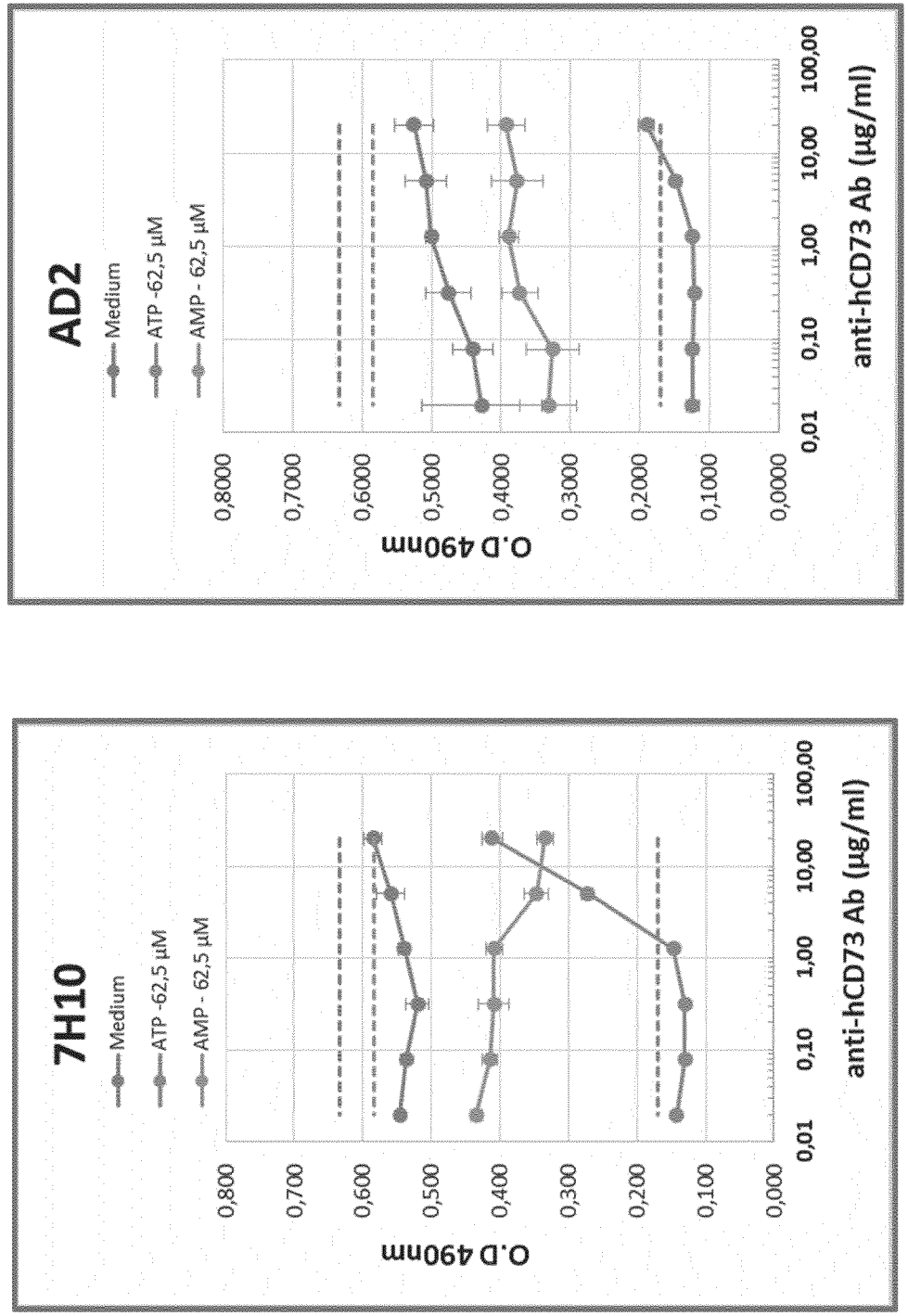
FIGS. 9A and 9B shows titration of antibodies 7H10 and 12F9 respectively for reversion of inhibition of proliferation, with optical density (DO) for each condition.
Figure 9B:
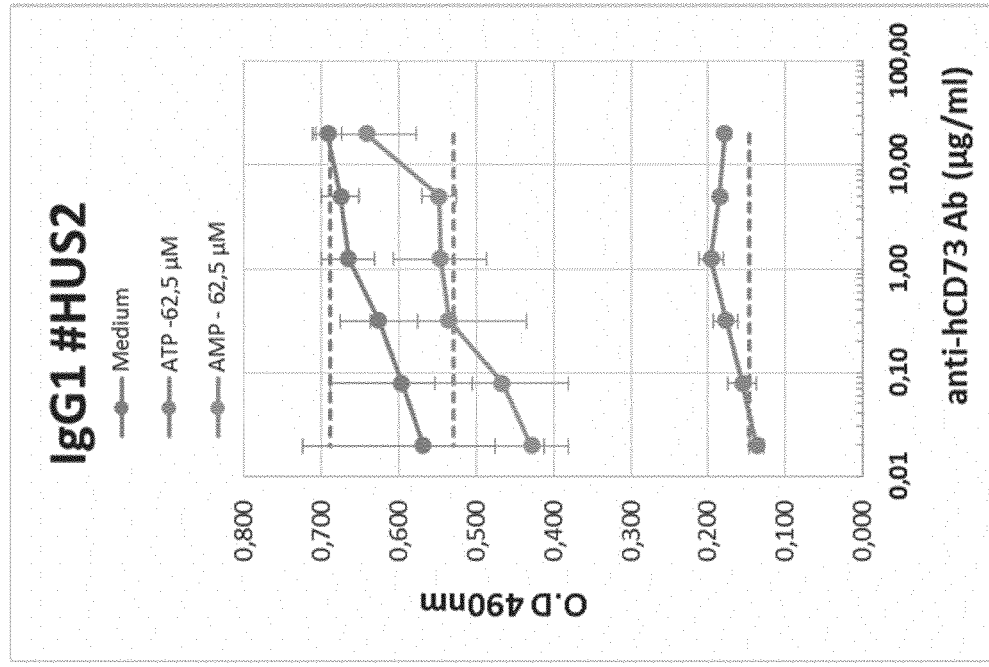
Figure 9B:
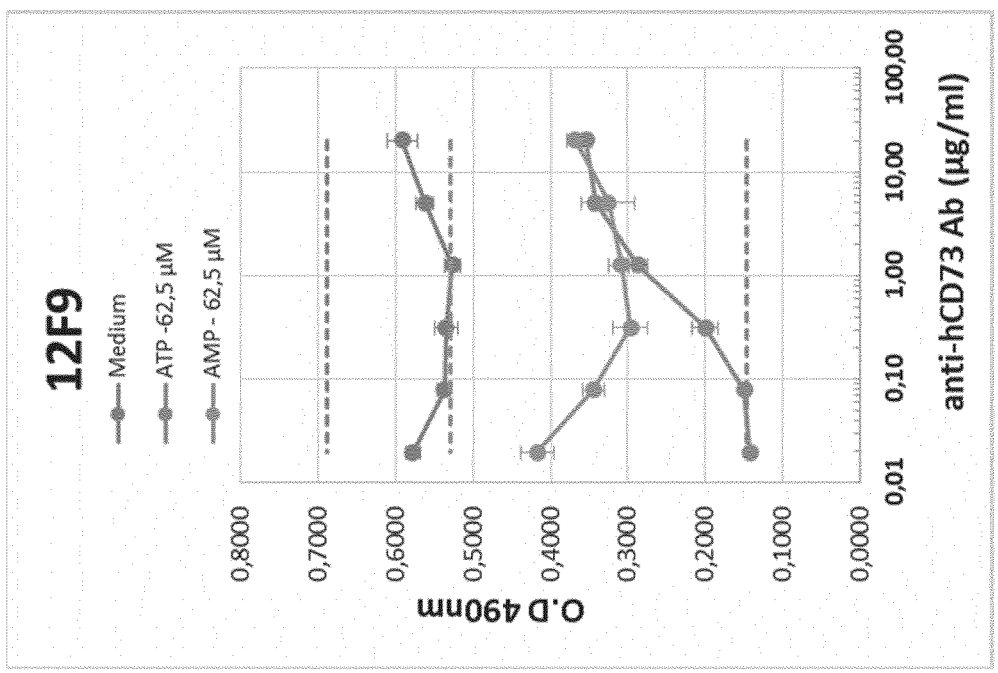

Results are shown in FIGS. 7A, 8A and 9A for antibody 7H10, and in 7B, 8B and 9B for antibody 12F9. Both antibodies 7H10 and 12F9 cause reversion of T cell proliferation inhibition in the presence of CD39-expressing B cells and ATP. Antibodies 7H10 and 12F9 were able to strongly increase T cell proliferation, notably at concentrations 20 µg/ml, at a concentration of above about 5 µg/ml was able to increase T cell proliferation by at least 2-fold and at a concentration of above about 10 µg/ml (e.g. 20 µg/ml) was able to increase T cell proliferation by more than 3-fold. In contrast, antibody AD2 did not significantly increase T cell proliferation.

Further to these findings, several additional anti-CD73 antibodies obtained in Example 1 were tested in this assay for ability of anti-CD73 antibodies to restore T cell proliferation in presence of ATP. Antibodies 15D7, 4B11, 11D9, 9D2 each also were able to increase T cell proliferation, although 12F9 and 7H10 were the most potent. The antibodies inhibit the activity of the human CD73 polypeptide without binding to the enzymatic active site of the CD73 polypeptide, and thus are believed to be capable of acting as allosteric inhibitors of CD73 expressed by cells. They are believed to be non-competitive inhibitors of CD73, e.g., they inhibit the activity of the human CD73 polypeptide without detectably reducing binding between the CD73 polypeptide and a natural substrate thereof. Antibodies 4B11, 11D9 and 9D2 did not cause down-modulation of CD73 expression on cells when tested in the assays of Example 4, while antibody 15D7 did induce down-modulation of CD73 expression on cells when tested in the assays of Example 4.

Consequently, the setting involving addition of exogenous ATP does not appear to permit the observation of any effect for a pure blocking antibody candidate. However, the addition of exogenous AMP in CD39-expressing B cell co-culture permits the observation of reversal of T cell proliferation inhibition. Antibodies 7H10, 12F9, 15D7, 4B11, 11D9 and 9D2, were able to reverse T cell proliferation inhibition in the presence of CD39-expressing B cells and ATP.

Example 7: Epitope Mapping

In order to define the epitopes of anti-CD73 antibodies, we designed CD73 mutants defined by substitutions of amino acids exposed at the molecular surface over the surface of CD73. Mutants were transfected in Hek-293T cells, as shown in the table below. The targeted amino acid mutations in the table 1 below are shown using numbering of SEQ ID NO: 1.

TABLE 1

| Mutant | Substitutions | | | | | |
|---|---|---|---|---|---|---|
| 1 | E46A | S49A | V52A | N53A | R56L | M58V |
| 2 | Q70S | R73A | A74E | A107I | R109G | |
| 3 | A99S | E129A | K133A | E134N | A135S | |
| 4 | K145A | K147A | S152H | S155A | Y161S | E203A K206A |
| 5 | P165S | D168G | N211A | E296A | R297A | |
| 6 | K179A | E196A | I197S | T198A | E224A | M225S Q231A |
| 7 | K262A | F265S | I266A | K274Q | I292A | S302A H304Y |
| 8 | P318A | S319A | K321A | N325A | K326Q | |
| 9 | Y345A | D347A | S349A | S352A | D399A | R401A |
| 10 | D460A | L461S | S462A | R463A | G466W | D467N K471A |
| 11 | D473A | K478A | R480A | S483A | D485A | K488E E491K |
| 12 | N503A | Q509A | K512S | D513A | | |
| 13 | R354A | R395A | Q444A | T446A | | |
| 14 | D332A | N333A | T336A | E409A | | |
| 15 | H375A | E378A | R517A | S520A | D522A | |

Generation of Mutants

CD73 mutants are generated by PCR. The sequences amplified are run on agarose gel and purified using the Macherey Nagel PCR Clean-Up Gel Extraction kit (reference 740609). The purified PCR products generated for each mutant are then ligated into an expression vector, with the ClonTech InFusion system. The vectors containing the mutated sequences are prepared as Miniprep and sequenced. After sequencing, the vectors containing the mutated sequences are prepared as Midiprep using the Promega PureYield™ Plasmid Midiprep System. HEK293T cells are grown in DMEM medium (Invitrogen), transfected with vectors using Invitrogen's Lipofectamine 2000 and incubated at 37° C. in a CO2 incubator for 24 hours prior to testing for transgene expression.

Flow Cytometry Analysis of Anti-CD73 Binding to the HEK293T Transfected Cells

Anti-CD73 antibodies are tested for their binding to each mutant by flow cytometry. A first experiment is performed to determine antibodies that lose their binding to one or several mutants at one concentration. To confirm a loss of binding, titration of antibodies is done on antibodies for which binding seemed to be affected by the CD73 mutations (1-0.1-0.01-0.001 µg/ml).

Figure 3A:
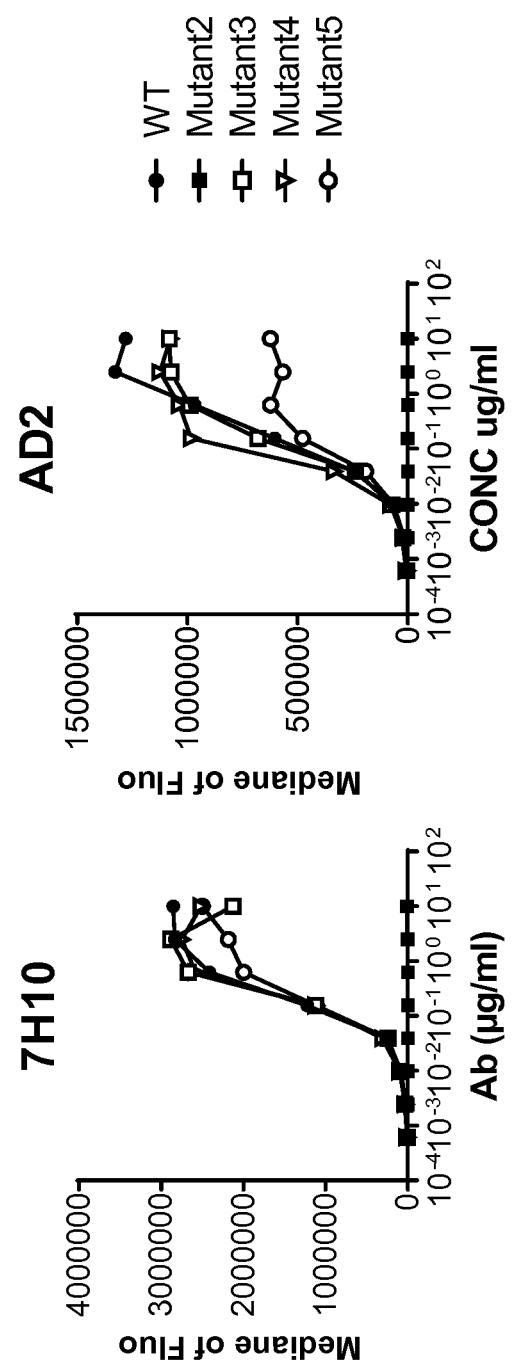
FIGS. 3A and 3B shows titration of antibodies by flow cytometry on cell expressing mutants of human CD73.

Antibody 7H10 lost binding to mutant 2 of CD73, but not to any other mutant. Mutant 2 contains amino acid substitutions at residues Q70, R73, A74, A107 and R109, indicating that one or more, or all of, the residues of the mutant are important to the core epitope of 7H10. Results for antibody 7H10 and AD2 are shown in FIG. 3A.

Figure 3B:
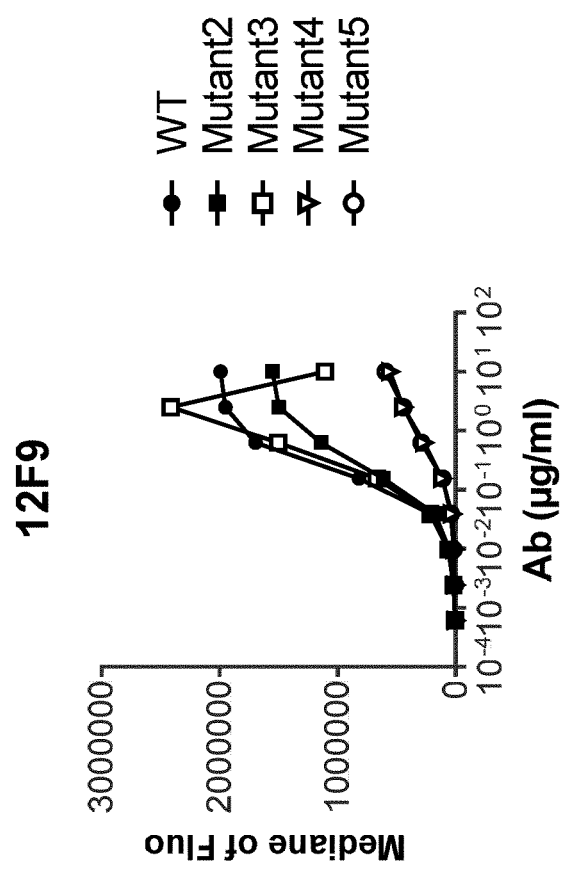
Figure 3C:
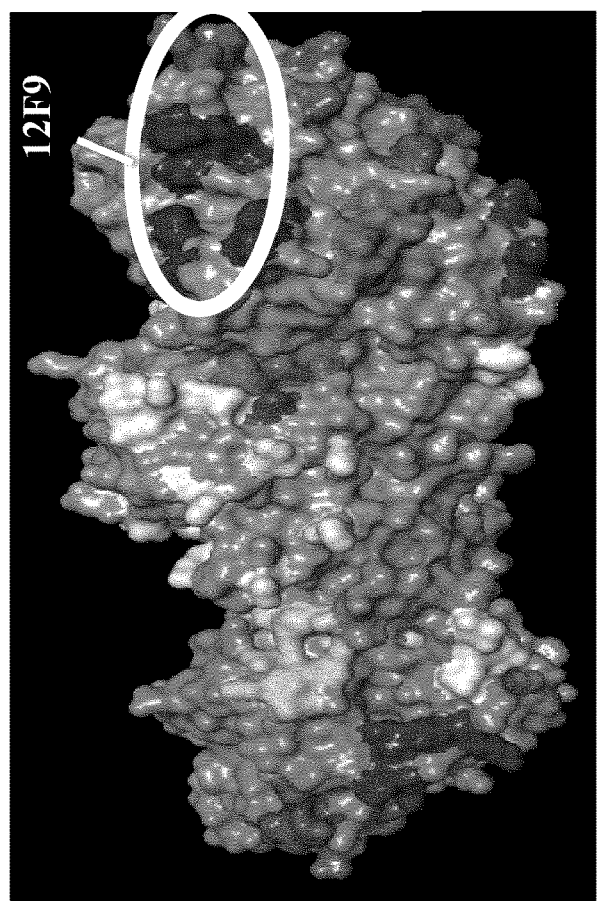
FIG. 3C shows the position of residues mutated in mutants 4 and 5 on the CD73 dimer, both in "open" (left hand panel) and "closed" (right hand panel) conformations.
Figure 3C:
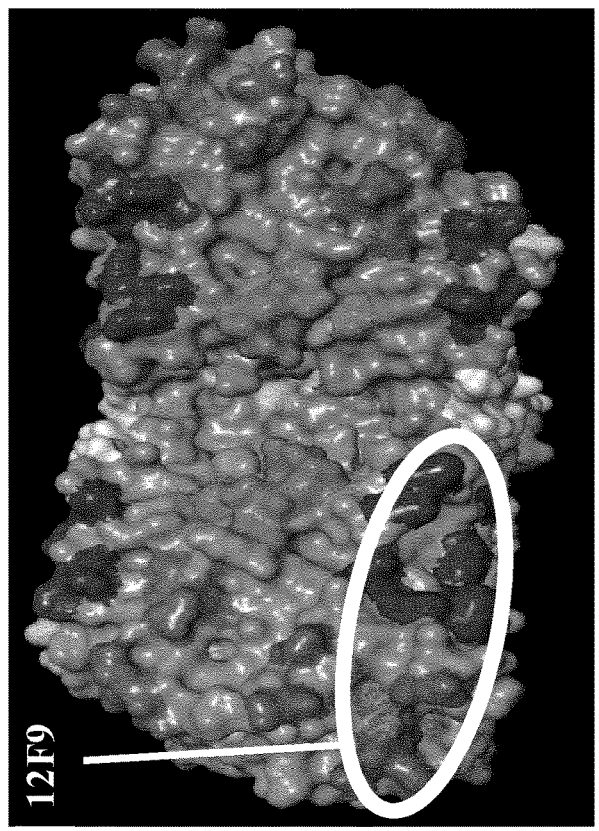

Antibody 12F9 lost binding to mutants 4 and 5 of CD73, but not to any other mutant. Mutant 4 contains amino acid substitutions at residues K145, K147, S152, S155, Y161, E203, K206, indicating that one or more, or all of, the residues of the mutant are important to the core epitope of 12F9. Mutant 5 contains amino acid substitutions at residues P165, D168, N211, E296, R297, indicating that one or more, or all of, the residues of the mutant are important to the core epitope of 12F9. Results for antibody 12F9 are shown in FIGS. 3B and 3C. FIG. 3B shows decrease in binding to mutants 4 and 5, while FIG. 3C shows the localization of the mutated residues, and hence the 12F9 binding zone, on dimeric human CD73, both in "open" (left hand panel) and "closed" (right hand panel) conformations. Antibody AD2 that causes clustering and internalization of CD73 did not lose binding to mutant 3; AD2 instead lost binding to mutant 2 having substitutions at residues Q70, R73, A74, A107 and R109. Antibody 7G2 lost binding to mutants 5, 6 and 7 (but not mutants 2 or 3).

Example 8: CD73 Binding Affinity by Surface Plasmon Resonance (SPR)

Biacore T100 General Procedure and Reagents

SPR measurements were performed on a Biacore T100 apparatus (Biacore GE Healthcare) at 25° C. In all Biacore experiments HBS-EP+(Biacore GE Healthcare) and NaOH 10 mM served as running buffer and regeneration buffer respectively. Sensorgrams were analyzed with Biacore T100 Evaluation software. Protein-A was purchase from (GE Healthcare). Human soluble dimeric CD73 proteins were cloned, produced and purified at Innate Pharma.

Immobilization of Protein-A

Protein-A proteins were immobilized covalently to carboxyl groups in the dextran layer on a Sensor Chip CM5. The chip surface was activated with EDC/NHS (N-ethyl-N'-(3-dimethylaminopropyl) carbodiimide hydrochloride and N-hydroxysuccinimide (Biacore GE Healthcare). Protein-A was diluted to 10 µg/ml in coupling buffer (10 mM acetate, pH 5.6) and injected until the appropriate immobilization level was reached (i.e. 2000 RU). Deactivation of the remaining activated groups was performed using 100 mM ethanolamine pH 8 (Biacore GE Healthcare).

Affinity Study

Affinity study was carried out according to a standard Capture-Kinetic protocol recommended by the manufacturer (Biacore GE Healthcare kinetic wizard). Serial dilutions of human recombinant soluble dimeric CD73 proteins, ranging from 1.23 to 300 nM were sequentially injected over the captured anti-CD73 antibodies and allowed to dissociate for 10 min before regeneration. The entire sensorgram sets were fitted using the 1:1 kinetic binding model. Bivalent affinities and kinetic association and dissociation rate constants for 7H10 was 0.527 nM (KD). Bivalent affinities and kinetic association and dissociation rate constants for 12F9 was 0.938 nM (KD).

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

---

The invention claimed is:

1. An isolated monoclonal antibody or antigen binding fragment comprising:

(a) a heavy chain variable domain comprising CDR 1, 2 and 3 of the heavy chain variable region of SEQ ID NO: 3 and (ii) a light chain variable domain comprising CDR 1, 2 and 3 of the light chain variable region of SEQ ID NO: 4;

(b) a heavy chain variable domain comprising CDR 1, 2 and 3 of the heavy chain variable region of SEQ ID NO: 21 and (ii) a light chain variable domain comprising CDR 1, 2 and 3 of the light chain variable region of SEQ ID NO: 22;

(c) a heavy chain variable domain comprising CDR 1, 2 and 3 of the heavy chain variable region of SEQ ID NO: 40 and (ii) a light chain variable domain comprising CDR 1, 2 and 3 of the light chain variable region of SEQ ID NO: 41;

(d) a heavy chain variable domain comprising CDR 1, 2 and 3 of the heavy chain variable region of SEQ ID NO: 42 and (ii) a light chain variable domain comprising CDR 1, 2 and 3 of the light chain variable region of SEQ ID NO: 43;

(e) a heavy chain variable domain comprising CDR 1, 2 and 3 of the heavy chain variable region of SEQ ID NO: 44 and (ii) a light chain variable domain comprising CDR 1, 2 and 3 of the light chain variable region of SEQ ID NO: 45; or (f) a heavy chain variable domain comprising CDR 1, 2 and 3 of the heavy chain variable region of SEQ ID NO: 46 and (ii) a light chain variable domain comprising CDR 1, 2 and 3 of the light chain variable region of SEQ ID NO: 47.

2. The isolated antibody of claim 1, wherein the antibody is IgG4 antibody, an antibody lacking an Fc domain, or an antibody having an Fc domain that is modified to reduce binding between the Fc domain and an Fcγ receptor.

3. The isolated antibody of claim 2, wherein the antibody comprises a modified human IgG1 Fc domain comprising N-linked glycosylation at Kabat residue N297 and comprising an amino acid substitution at Kabat residue(s) 234 and 235, optionally further at Kabat residue 331, optionally at Kabat residues 234, 235, 237 and at Kabat residues 330 and/or 331, optionally wherein the Fc domain comprises L234A/L235E/P331S substitutions, L234F/L235E/P331S substitutions, L234A/L235E/G237A/P331S substitutions, or L234A/L235E/G237A/A330S/P331S substitutions.

4. The isolated antibody of claim 1, wherein the antibody comprises a VH domain comprising a human framework region from a gene of a human V gene group selected from the group consisting of: IGHV1-18, IGHV1-2, IGHV1-24, IGHV1-3, IGHV1-45, IGHV1-46, IGHV1-58, IGHV1-69, IGHV1-8, IGHV2-26, IGHV2-5, IGHV2-70, IGHV2-70D, IGHV3-11, IGHV3-13, IGHV3-15, IGHV3-20, IGHV3-21, IGHV3-23, IGHV3-23D, IGHV3-30, IGHV3-30-3, IGHV3-30-5, IGHV3-33, IGHV3-43, IGHV3-43D, IGHV3-48, IGHV3-49, IGHV3-54, IGHV3-64, IGHV3-64D, IGHV3-66, IGHV3-7, IGHV3-72, IGHV3-73, IGHV3-74, IGHV3-9, IGHV3-NL1, IGHV4-28, IGHV4-30-1, IGHV4-30-2, IGHV4-30-4, IGHV4-31, IGHV4-34, IGHV4-38-2, IGHV4-39, IGHV4-4, IGHV4-59, IGHV4-61, IGHV5-10-1, IGHV5-51, IGHV6-1 and IGHV7-4-1; and a VL domain comprising a human framework region from a gene of a human V gene group selected from the group consisting of: IGKV1-12, IGKV1-13, IGKV1-16, IGKV1-27, IGKV1-33, IGKV1-39, IGKV1-5, IGKV1-6, IGKV1-8, IGKV1-9, IGKV1-NL1, IGKV1D-12, IGKV1D-13, IGKV1D-16, IGKV1D-17, IGKV1D-33, IGKV1D-39, IGKV1D43, IGKV1D8, IGKV2-24, IGKV2-28, IGKV2-29, IGKV2-30, IGKV2-40, IGKV2D-26, IGKV2D-28, IGKV2D-29, IGKV2D-30, IGKV2D-40, IGKV3-11, IGKV3-15, IGKV3-20, IGKV3D-11, IGKV3D-15, IGKV3D-20, IGKV3D-7, IGKV4-1, IGKV5-2, IGKV6-21 and IGKV6D-21.

5. A pharmaceutical composition comprising the monoclonal antibody, or antigen binding fragment thereof according to claim 1 and one or more additional ingredient.

* * * * *

UNITED STATES PATENT AND TRADEMARK OFFICE
CERTIFICATE OF CORRECTION

PATENT NO. : 11,130,817 B2
APPLICATION NO. : 15/767661
DATED : September 28, 2021
INVENTOR(S) : Christophe Caux et al.

Page 1 of 1

It is certified that error appears in the above-identified patent and that said Letters Patent is hereby corrected as shown below:

In the Specification

Column 29,
Line 50, "ESNGQPENNYKTIPPVLDSDGSFF" should read --ESNGQPENNYKTTPPVLDSDGSFF--.

Columns 37-38,
Line 48, Table A – 3a, "1109" should read --11D9--.

Column 42,
Line 65, "antigen (5)," should read --antigen (s),--.

Column 51,
Line 32, "Doses of ≤ 10," should read --Doses of ≤ 1, 10,--.
Line 52, "YW243.55.570" should read --YW243.55.S70--.

Column 54,
Line 38, "CaCl$_2$) 4" should read --CaC12 4--.

Column 57,
Line 24, "4611," should read --4B11,--.

Column 60,
Line 18, "Chip CMS." should read --Chip CM5.--.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*